United States Patent [19]
Davis et al.

[11] Patent Number: 5,925,566
[45] Date of Patent: Jul. 20, 1999

[54] NON-ACTIVATED RECEPTOR COMPLEX PROTEINS AND USES THEREOF

[75] Inventors: Roger J. Davis, Princeton; Zoya Galcheva-Gargova, Worcester, both of Mass.

[73] Assignee: University of Massachusetts, Boston, Mass.

[21] Appl. No.: 08/870,518

[22] Filed: Jun. 6, 1997

Related U.S. Application Data

[60] Provisional application No. 60/019,219, Jun. 6, 1996.
[51] Int. Cl.$^6$ .................................................... C12N 15/00
[52] U.S. Cl. ........................... 435/325; 514/44; 424/93.2; 435/6; 435/69.1; 435/320.1; 435/325; 536/23.1; 536/23.5
[58] Field of Search .............................. 514/44; 424/93.2; 435/320.1, 325, 6, 69.1; 536/23.1, 23.5; 935/22, 33, 34, 52, 77

[56] References Cited

U.S. PATENT DOCUMENTS 5,708,142  1/1998  Goeddel et al. ......................... 530/350

FOREIGN PATENT DOCUMENTS

WO 95/19431  7/1995  WIPO .

OTHER PUBLICATIONS

Crystal, "Transfer of Genes to Humans: Early Lessons and Obstacles to Success" Science 270:404–410, 1995.
Bork et al., "A Phosphotyrosine Interaction Domain," Cell, 80:693–694, 1995.
Galcheva–Gargova et al., "Binding of Zinc Finger Protein ZPR1 to the Epidermal Growth Factor Receptor," Science, 272:1797–1802, 1996.
Kavanaugh et al., "An Alternative to SH2 Domains for Binding Tyrosine–Phosphorylated Proteins," Science, 266:1862–1865, 1994.
Kavanaugh et al., "PTB Domain Binding to Signaling Proteins Through a Sequence Motif Containing Phosphotyrosine," Science, 268:1177–1179, 1995.
Koch et al., "SH2 and SH3 Domains: Elements That Control Interactions of Cytoplasmic Signaling Proteins," Science, 252:668–674, 1991.
Pawson et al., From Structure to Function, Cell, 71:359–362, 1992.
Schlessinger et al., "Growth Factor Signaling by Receptor Tyrosine Kinase," Neuron, 9:383–391, 1992.
Song et al., "Association of a Ring Finger Protein with the Cytoplasmic Domain in the Human Type–2 Tumor Necrosis Factor Receptor," Biochem. J. 309:825–829, 1995.
Ullrich, et al., "Signal Transduction by Receptors with Tyrosine Kinase Activity," Cell, 61:203–212, 1990.
Ngo et al., in: *The Protein Folding Problem and Tertiary Structure Prediction*, 1994, Merz et al., (ed.), Birkhauser, Boston, MA, pp. 433 and 492–495.
Kreitman et al. (P.N.A.S., vol. 91, pp. 6889–6893, 1994).
Guerreiro et al. (Gene bank AN Z72996, May 17, 1996).
Muris et al. (Gene bank, AN Z29640, Jan. 30, 1996).

*Primary Examiner*—Bruce R. Campell
*Assistant Examiner*—Dave Trong Nguyen
*Attorney, Agent, or Firm*—Fish & Richardson, P.C.

[57] ABSTRACT

The invention features a substantially pure ZPR1 polypeptide. For example, a ZPR1 polypeptide that specifically binds to a non-activated membrane-bound receptor (e.g., EGF or PDGF receptors) and specifically binds small nucleolar RNAs (e.g., U3). ZPR1 polypeptides can be isolated from any eukaryote, including mammals (e.g. rodents and humans) and fungi (e.g., *S. cerevisiae* and *S. pombe*).

23 Claims, 18 Drawing Sheets

| | |
|---|---:|
| CCGCTCCCCG TTCCTCCACA ACCACAACCT TTCTTTTTCA AAGAAGATTT GCCCCGGGGA | 60 |
| AGCCGCCGCG GGAGCAACGC GTGGGGAG ATG TCT GCC AGC GGG GCT GTG CAG<br>                                                        Met Ser Ala Ser Gly Ala Val Gln<br>                                                          1              5 | 112 |
| CCG GGA CAC CCG GGG GCC GCC GTC GGG CCC TCG CCC GCT GCG GCT GCG<br>Pro Gly His Pro Gly Ala Ala Val Gly Pro Ser Pro Ala Ala Ala Ala<br>        10                  15                        20 | 160 |
| TCA CCA GCC ACC GGG CCT TTG TTC CGG CCC CTC AGC GCC GAA GAT GAG<br>Ser Pro Ala Thr Gly Pro Leu Phe Arg Pro Leu Ser Ala Glu Asp Glu<br>25                 30                        35                        40 | 208 |
| GAG CAA CAG CCC ACC GAG ATC GAG TCA CTG TGC ATG AAC TGT TAC CGG<br>Glu Gln Gln Pro Thr Glu Ile Glu Ser Leu Cys Met Asn Cys Tyr Arg<br>                 45                              *                  * | 256 |
| AAC GGC ACG ACG CGA CTT CTG CTC ACC AAG ATC CCC TTC TTT AGA GAA<br>Asn Gly Thr Thr Arg Leu Leu Leu Thr Lys Ile Pro Phe Phe Arg Glu<br>                     Zinc Finger 1                        70 | 304 |
| ATC ATC GTG AGC TCC TTT TCC TGC GAA CAC TGT GGC TGG AAC AAC ACG<br>Ile Ile Val Ser Ser Phe Ser Cys Glu His Cys Gly Trp Asn Asn Thr<br>          75                       *                  * | 352 |
| GAG ATC CAG TCT GCA GGC AGG ATC CAG GAC CAG GGA GTG CGC TAC ACC<br>Glu Ile Gln Ser Ala Gly Arg Ile Gln Asp Gln Gly Val Arg Tyr Thr<br>        90                        95                        100 | 400 |
| TTG ACC GTG AGA AGC CAA GAG GAC ATG AAC AGA GAA GTG GTA AAG ACA<br>Leu Thr Val Arg Ser Gln Glu Asp Met Asn Arg Glu Val Val Lys Thr<br>105                110                    115                  120 | 448 |
| GAC TCT GCC ACC ACA AGG ATC CCC GAG CTG GAT TTT GAG ATT CCA GCC<br>Asp Ser Ala Thr Thr Arg Ile Pro Glu Leu Asp Phe Glu Ile Pro Ala<br>                    125                    130                  135 | 496 |
| TTC AGC CAG AAG GGA GCT CTG ACC ACT GTT GAA GGA CTC ATC AGC CGT<br>Phe Ser Gln Lys Gly Ala Leu Thr Thr Val Glu Gly Leu Ile Ser Arg<br>          140                        145                    150 | 544 |
| GCG ATC TCT GGC CTG GAA CAG GAT CAG CCC ACA CGA CGG GCA GTG GAA<br>Ala Ile Ser Gly Leu Glu Gln Asp Gln Pro Thr Arg Arg Ala Val Glu<br>               155                    160                    165 | 592 |
| GGT GCC ATC GCA GAG AGA ATT GAT GAG TTC ATT GGC AAA CTG AAG GAC<br>Gly Ala Ile Ala Glu Arg Ile Asp Glu Phe Ile Gly Lys Leu Lys Asp<br>    170                      175                        180 | 640 |
| CTA AAG CAA ATG GCT TCC CCT TTC ACA CTG GTC ATT GAT GAT CCC TCG<br>Leu Lys Gln Met Ala Ser Pro Phe Thr Leu Val Ile Asp Asp Pro Ser<br>185                190                    195                  200 | 688 |
| GGA AAC AGC TTT GTA GAA AAC CCA CAT GCT CCC CAG AAA GAT AAT GCC<br>Gly Asn Ser Phe Val Glu Asn Pro His Ala Pro Gln Lys Asp Asn Ala<br>                    205                    210                  215 | 736 |
| TTG GTG ATC ACA TAC TAT GAC CGA ACC CCA CAG CAA GCT GAG ATG CTG<br>Leu Val Ile Thr Tyr Tyr Asp Arg Thr Pro Gln Gln Ala Glu Met Leu<br>          220                        225                  230 | 784 |

FIG. 1A

| | |
|---|---|
| GGG CTC CAA GCA GAA GCA CCA GAG GAG AAG GCG GAA GAG GAA GAC CTT<br>Gly Leu Gln Ala Glu Ala Pro Glu Glu Lys Ala Glu Glu Glu Asp Leu<br>235                        240                    245 | 832 |
| AGA AAC GAA GTG CTC CAG TTC AAC ACT AAC TGC CCA GAG TGC AAC GCT<br>Arg Asn Glu Val Leu Gln Phe Asn Thr Asn Cys Pro Glu Cys Asn Ala<br>250                        255              *                  * | 880 |
| CCG GCT CAG ACC AAC ATG AAG CTT GTC CAA ATC CCC CAC TTT AAA GAG<br>Pro Ala Gln Thr Asn Met Lys Leu Val Gln Ile Pro His Phe Lys Glu<br>265                           Zinc Finger 2         280 | 928 |
| GTT ATC ATC ATG GCC ACC AAC TGT GAG AAT TGT GGG CAT CGG ACT AAT<br>Val Ile Ile Met Ala Thr Asn Cys Glu Asn Cys Gly His Arg Thr Asn<br>285                *                 * | 976 |
| GAG GTG AAG TCC GGA GGA GCT GTA GAA CCT TTG GGT ACC AGG ATC ACC<br>Glu Val Lys Ser Gly Gly Ala Val Glu Pro Leu Gly Thr Arg Ile Thr<br>                300                    305                   310 | 1024 |
| CTC CAC ATC ACA GAT CCC TCA GAC ATG ACC AGA GAC CTC CTC AAG TCT<br>Leu His Ile Thr Asp Pro Ser Asp Met Thr Arg Asp Leu Leu Lys Ser<br>315                        320                    325 | 1072 |
| GAG ACC TGT AGT GTG GAA ATC CCA GAG CTT GAG TTT GAA CTG GGA ATG<br>Glu Thr Cys Ser Val Glu Ile Pro Glu Leu Glu Phe Glu Leu Gly Met<br>330                        335                    340 | 1120 |
| GCT GTA CTT GGG GGC AAG TTC ACC ACT CTA GAA GGA CTG CTG AAA GAC<br>Ala Val Leu Gly Gly Lys Phe Thr Thr Leu Glu Gly Leu Leu Lys Asp<br>345                        350                    355                   360 | 1168 |
| ATC CGA GAA CTG GTA ACC AAG AAC CCA TTC ACA CTG GGC GAC AGC TCT<br>Ile Arg Glu Leu Val Thr Lys Asn Pro Phe Thr Leu Gly Asp Ser Ser<br>                365                    370                   375 | 1216 |
| AAT CCT GAC CAG TCA GAG AAA CTG CAG GAG TTT AGC CAG AAG TTG GGC<br>Asn Pro Asp Gln Ser Glu Lys Leu Gln Glu Phe Ser Gln Lys Leu Gly<br>                380                    385                   390 | 1264 |
| CAG ATC ATC GAG GGC AAG ATG AAG GCC CAC TTT ATC ATG AAT GAT CCA<br>Gln Ile Ile Glu Gly Lys Met Lys Ala His Phe Ile Met Asn Asp Pro<br>395                        400                    405 | 1312 |
| GCA GGA AAC AGT TAT CTG CAG AAT GTG TAT GCA CCT GAA GAC GAT CCA<br>Ala Gly Asn Ser Tyr Leu Gln Asn Val Tyr Ala Pro Glu Asp Asp Pro<br>                410                    415                   420 | 1360 |
| GAG ATG AAG GTC GAG CGG TAC AAA CGC ACC TTT GAC CAA AAT GAG GAG<br>Glu Met Lys Val Glu Arg Tyr Lys Arg Thr Phe Asp Gln Asn Glu Glu<br>425                        430                    435                   440 | 1408 |
| CTC GGG CTC AAT GAC ATG AAG ACA GAG GGC TAT GAG GCG GGC CTG GCC<br>Leu Gly Leu Asn Asp Met Lys Thr Glu Gly Tyr Glu Ala Gly Leu Ala<br>                      445                    450                   455 | 1456 |
| CCA CAG CGG T AGCAGTGGCC AGCTCACTGG CCAGCTACAG TGCCACTCAC<br>Pro Gln Arg (SEQ ID NO: 1) | 1506 |
| ACTGCAGGGT TATCTGTTAC TGTGGGGAAC TGACGAGGAG TGCTCAAGCC CTCGTCCATG | 1566 |
| GTGAAGAGGT TACCACTTGA GTTAGAAATG TAAGCACCCA AGATTAGCAG CTGACGGACG | 1626 |

FIG. 1B

| | | | | | |
|---|---|---|---|---|---|
| AGGCAGCTGC | AGCCCTACTG | TGCTCCTTGA | CCTTCTTTTG | GAGGTTTTAA | AGTCGGCGTG | 1686 |
| AGAAGAATCC | CAGAAACACC | AGGCGGTCTG | CCATCACCGT | TTGCCTGTCA | GCTCTCTGAC | 1746 |
| CTCCAGTGCT | GGACCTTTGA | AGTCTGGGGA | AGTGAAATAC | AAGTTTCTGC | TGGCTCTGGG | 1806 |
| CATGTGAAGT | ACTGACTCAG | CAGGGCAAGG | ATGTCGGAGG | GGCCGAGCAG | GCACAGGTGA | 1866 |
| AGACGCCACA | TTAAAGTGAT | GGCCTTTAAA | CGAAAGGAGA | ACAACTATCC | AGACTCCTAC | 1926 |
| CTCCCACATG | GAAGAAACCG | CCACCTCATC | AAGTTAATAA | AGAAAAAGAA | AAGAAGGGAG | 1986 |
| GTCCAGAGTC | ATTCCCACAT | TCTGTTGGAG | GAGGAGAGAA | GGATGTTCAC | TACTTGGTGC | 2046 |
| ATACAGGCAT | GCACACGGAC | AGACAGGTGC | GTGCACACAC | ACAACCACAC | ACAAACACAG | 2106 |
| GTTTGCTGAT | GGAACATTAT | TATACAATTC | TGAGCTTACA | TAAAAAAAAA | AAAAAA | 2162 |

(SEQ ID NO: 5)

FIG. 1C

```
            *       *                                                        70
       1  MAASGAVEPGPPGAAVAPSPAPAPPPAPDHLFRPISAEDEEQQPTEIESLCMNCYCNGMTRLLLT
Human      MS....Q..H.....G....A.AS.TGP..L.....................R..T........
Mouse      MSEQKEDLFKFV.EAA.E.EDESIAEQNK.N.GVKLTGAQDAMGHFVQ..........GK..T..
S. cervisiae  MAEEKKEELFTSI.NAAQN.---------------STAEDREGNGVQ.V.....E.GK..T.K..
S. pombe                    G          V                    E   ESLCM C  NG T  LLLT
Consensus

*                                                         140
      71  KIPFFREIIVSSFSCEHCGWNNTEIQSAGRIQDQGVRYTLSVRALEDMNREVVKTDSAATRIPELDFEIP
Human      S..Y....IM.D.P..FK.C...P.SQ..EK.S..V.K.ECR..F..Q.I.SET TCKFV...I.......
Mouse      V..Y...VVLM.E.P..FK.AQV.H.ET..PE.TKITFH.EDK..L..T...SQE.IVS...IQL.....
S. cervisiae  IP FRE   SF C HCG N  Q A IQ G     V   ED NR V K    A    E    EIP
S. pombe
Consensus       G 210
     141  AFSQKGALTTVEGLITRAISGLEQDQPARRANKDATAERIDEFIVKLKELKQVAS---PFTLIIDDPSGN
Human      .S......T.VEG.I......G..D..M......V......
Mouse      .-KR.Q.......LSEM.DD.S..EM.KSIDE.LYKK..D..Q.V.SYINCEPNTI.I.F.L..A.....
S. cervisiae  G--RL.Q.......LSNVVDD.SKEQES.KESAPQLYDQ.NA..E.VNS.---R.GSV..ITV..IT....
S. pombe   G LTTVEGL    L Q R      I FI K            P T    DD GN
Consensus 280
     211  SFVENPHAPQKDDALVITHYNRTRQQEEMLGLQEEAPAEK--------------------
Human      .N....Y...P..A....A..E................
Mouse      .WI.YKPG-EPQHKWSH.Q.V..DE.NVQV.IITRDQL.QRRQEQLKQLANRERNPSESVKVGSANPQFL
S. cervisiae  .WI.MKPG-RDG.RWSQVS.K..LE.NTK...VDTDQP............-DVKTQTNNASNTLK-----
S. pombe   S  E           Y RT  Q   G         E
Consensus

*      *                                      350
     281  ---PEEEDLRNEVLQFSTNCPECNAPAQTNMKLVQIPHFKEVIIMATNCENCGHRTNEVKSGGAVEPLGT
Human      ---A.............N...................................................
Mouse      SDATDI.NFN....QT.RAS..S.TQECE.H..P.N............S.V.DH..YKS....T...IPDK.R
S. cervisiae  HDATAV.VDP....HT.HAT..S.SHQCD.H...LD............S.V.DR..Y.S....T..EIP.K.R
S. pombe       E  NEV F  CP C     T MK    IPHFKEVIIM T C  CG   NEVK GG     G
Consensus

*                                    420
     351  RITLHITDASDMTRDLLKSETCSVEIPELEFELGMAVLGGKFTTLEGLLKDIRELVTKNPFTL-GDSSNP
Human      ........P................................
Mouse      .......YCD..A.LS..I......MV....HLDIQEGT...R..L...RQVY.ELESRI..QTS..MDE
S. cervisiae  K...KVM..E.LS..I......A.LK....GLD.FPGT...R..I....AQVYDELYARV.SQET..MT.
S. pombe      ITL   D  D  RD LKSET S  IPEL        LGG FTT EGLL           F    DS
Consensus 500
     421  GQTERLQEFSQKMDQIIEGNMKAHFIMDDPAGNSYLQNVAPEDDPEMKVERYKRTFDQNEELGLNDMKTEGYEAGLAPQR
Human      D.S.K....LG....K.....N..............DP..N.TI.D.E..KE.........S.I.V.............
Mouse      ATKA.WV..FA.LKEA.A.KV.FTV..E..LAG..I......DP..N.TI.E..KE.........S.I.V.............
S. cervisiae  E.VANW.Q.LCNLTAAR..ATQFTL.L...LSQ....Y..DP..N.TI.E.E..S.QV........N..KDGGKK
S. pombe       F       G     I DP  SY QN YAP DP M  EYR    NEELGL D K E
Consensus (SEQ ID NO: 2)
(SEQ ID NO: 1)
(SEQ ID NO: 3)
(SEQ ID NO: 4)
(SEQ ID NO: 33)
```

FIG. 2

| | | | | | | | | | | | | | | |
|---|---|---|---|---|---|---|---|---|---|---|---|---|---|---|
| Met 1 | Ser | Glu | Gln | Lys 5 | Glu | Asp | Leu | Phe | Lys 10 | Pro | Val | Gly | Glu | Ala 15 |
| Ala | Glu | Val | Glu 20 | Asp | Glu | Ser | Ile | Ala 25 | Glu | Gln | Asn | Lys | Ala 30 | Asn | Asp |
| Gly | Val | Lys 35 | Leu | Thr | Gly | Ala | Gln 40 | Asp | Ala | Met | Gly | His 45 | Pro | Val | Gln |
| Glu | Ile 50 | Glu | Ser | Leu | Cys | Met 55 | Asn | Cys | Gly | Lys | Asn 60 | Gly | Thr | Thr | Arg |
| Leu 65 | Leu | Leu | Thr | Ser | Ile 70 | Pro | Tyr | Phe | Arg | Glu 75 | Ile | Ile | Ile | Met | Ser 80 |
| Phe | Asp | Cys | Pro | His 85 | Cys | Gly | Phe | Lys | Asn 90 | Cys | Glu | Ile | Gln | Pro 95 | Ala |
| Ser | Gln | Ile | Gln 100 | Glu | Lys | Gly | Ser | Arg 105 | Tyr | Val | Leu | Lys | Val 110 | Glu | Cys |
| Arg | Glu | Asp 115 | Phe | Asn | Arg | Gln | Val 120 | Ile | Lys | Ser | Glu | Thr 125 | Ala | Thr | Cys |
| Lys | Phe 130 | Val | Glu | Leu | Asp | Ile 135 | Glu | Ile | Pro | Ala | Lys 140 | Arg | Gly | Gln | Leu |
| Thr 145 | Thr | Val | Glu | Gly | Leu 150 | Leu | Ser | Glu | Met | Ile 155 | Asp | Asp | Leu | Ser | Gln 160 |
| Asp | Gln | Glu | Met | Arg 165 | Lys | Ser | Ile | Asp | Glu 170 | Ala | Leu | Tyr | Lys | Lys 175 | Ile |
| Asp | Asp | Phe | Ile 180 | Gln | Lys | Val | Lys | Ser 185 | Tyr | Ile | Asn | Cys | Glu 190 | Pro | Asn |
| Thr | Ile | Pro 195 | Ile | Thr | Phe | Ile | Leu 200 | Asp | Asp | Pro | Ala | Gly 205 | Asn | Ser | Trp |
| Ile | Glu 210 | Tyr | Lys | Pro | Gly | Glu 215 | Pro | Gln | His | Lys | Trp 220 | Ser | His | Thr | Gln |
| Tyr 225 | Val | Arg | Thr | Asp | Glu 230 | Gln | Asn | Val | Gln | Val 235 | Gly | Ile | Ile | Thr | Arg 240 |
| Asp | Gln | Leu | Glu | Gln 245 | Arg | Arg | Gln | Glu | Gln 250 | Leu | Lys | Gln | Leu | Ala 255 | Asn |
| Arg | Glu | Arg | Asn 260 | Pro | Ser | Glu | Ser | Val 265 | Lys | Val | Gly | Ser | Ala 270 | Asn | Pro |
| Gln | Phe | Leu 275 | Ser | Asp | Ala | Thr | Asp 280 | Ile | Glu | Asn | Phe | Asn 285 | Asn | Glu | Val |
| Gln | Thr 290 | Phe | Arg | Ala | Ser | Cys 295 | Pro | Ser | Cys | Thr | Gln 300 | Glu | Cys | Glu | Thr |
| His 305 | Met | Lys | Pro | Val | Asn 310 | Ile | Pro | His | Phe | Lys 315 | Glu | Val | Ile | Ile | Met 320 |
| Ser | Thr | Val | Cys | Asp 325 | His | Cys | Gly | Tyr | Lys 330 | Ser | Asn | Glu | Val | Lys 335 | Thr |

FIG. 3A

```
Gly Gly Ala Ile Pro Asp Lys Gly Arg Arg Ile Thr Leu Tyr Cys Asp
            340             345             350

Asp Ala Ala Asp Leu Ser Arg Asp Ile Leu Lys Ser Glu Thr Cys Ser
            355             360             365

Met Val Ile Pro Glu Leu His Leu Asp Ile Gln Glu Gly Thr Leu Gly
    370             375             380

Gly Arg Phe Thr Thr Leu Glu Gly Leu Leu Arg Gln Val Tyr Glu Glu
385             390             395             400

Leu Glu Ser Arg Ile Phe Thr Gln Thr Ser Asp Ser Met Asp Glu Ala
            405             410             415

Thr Lys Ala Arg Trp Val Glu Phe Phe Ala Lys Leu Lys Glu Ala Ile
            420             425             430

Ala Gly Lys Val Lys Phe Thr Val Ile Met Glu Asp Pro Leu Ala Gly
            435             440             445

Ser Tyr Ile Gln Asn Val Tyr Ala Pro Asp Pro Asp Pro Asn Met Thr
    450             455             460

Ile Glu Asp Tyr Glu Arg Thr Lys Glu Gln Asn Glu Asp Leu Gly Leu
465             470             475             480

Ser Asp Ile Lys Val Glu
            485
```

(SEQ ID NO: 3)

FIG. 3B

Met Ala Glu Glu Lys Lys Glu Glu Leu Phe Thr Ser Ile Gly Asn Ala
1               5                   10                  15

Ala Gln Asn Val Ser Thr Ala Glu Asp Arg Glu Gly Asn Gly Val Gln
            20                  25                  30

Glu Val Glu Ser Leu Cys Met Glu Cys Gly Lys Asn Gly Thr Thr Lys
        35                  40                  45

Leu Leu Leu Thr Val Ile Pro Tyr Phe Arg Glu Val Val Leu Met Ser
    50                  55                  60

Phe Glu Cys Pro His Cys Gly Phe Lys Asn Ala Gln Val Gln His Ala
65              70                  75                  80

Glu Thr Ile Gln Pro Glu Gly Thr Lys Ile Thr Phe His Val Glu Asp
            85                  90                  95

Lys Glu Asp Leu Asn Arg Thr Val Val Lys Ser Gln Glu Ala Ile Val
            100                 105                 110

Ser Ile Pro Glu Ile Gln Leu Glu Ile Pro Gly Arg Leu Gly Gln Leu
        115                 120                 125

Thr Thr Ile Glu Gly Ile Leu Ser Asn Val Val Asp Asp Leu Ser Lys
    130                 135                 140

Glu Gln Glu Ser Arg Lys Glu Ser Ala Pro Gln Leu Tyr Asp Gln Ile
145                 150                 155                 160

Asn Ala Phe Ile Glu Lys Val Asn Ser Leu Arg Ser Gly Ser Val Pro
            165                 170                 175

Phe Thr Ile Thr Val Asp Asp Ile Thr Gly Asn Ser Trp Ile Glu Met
            180                 185                 190

Lys Pro Gly Arg Asp Gly Asp Arg Trp Ser Gln Val Ser Tyr Lys Arg
        195                 200                 205

Thr Leu Glu Gln Asn Thr Lys Leu Gly Leu Val Asp Thr Asp Gln Pro
    210                 215                 220

Glu Asp Val Lys Thr Gln Thr Asn Asn Ala Ser Asn Thr Leu Lys His
225                 230                 235                 240

Asp Ala Thr Ala Val Glu Val Asp Pro Asn Glu Val His Thr Phe His
            245                 250                 255

Ala Thr Cys Pro Ser Cys Ser His Gln Cys Asp Thr His Met Lys Leu
            260                 265                 270

Leu Asp Ile Pro His Phe Lys Glu Val Ile Ile Met Ser Thr Val Cys
    275                 280                 285

Asp Arg Cys Gly Tyr Arg Ser Asn Glu Val Lys Thr Gly Gly Glu Ile
    290                 295                 300

Pro Pro Lys Gly Arg Lys Ile Thr Leu Lys Val Met Asp Ala Glu Asp
305                 310                 315                 320

Leu Ser Arg Asp Ile Leu Lys Ser Glu Thr Ala Ser Leu Lys Ile Pro
            325                 330                 335

FIG. 4A

```
Glu Leu Gly Leu Asp Leu Phe Pro Gly Thr Leu Gly Gly Arg Phe Thr
            340                 345                 350

Thr Ile Glu Gly Leu Leu Ala Gln Val Tyr Asp Glu Leu Tyr Ala Arg
        355                 360                 365

Val Phe Ser Gln Glu Thr Asp Ser Met Thr Pro Glu Gln Val Ala Asn
    370                 375                 380

Trp Gln Gln Phe Leu Cys Asn Leu Thr Ala Ala Arg Glu Gly Ala Thr
385                 390                 395                 400

Gln Phe Thr Leu Ile Leu Asp Asp Pro Leu Ser Gln Ser Tyr Leu Gln
                405                 410                 415

Asn Tyr Tyr Ala Pro Asp Pro Asp Pro Asn Met Thr Ile Glu Glu Tyr
            420                 425                 430

Glu Arg Ser Phe Gln Val Asn Glu Glu Leu Gly Leu Asn Asp Met Lys
        435                 440                 445

Thr Glu Asn Tyr Glu Lys Asp Gly Gly Lys Lys
    450                 455
```

(SEQ ID NO: 4)

FIG. 4B

```
TGCCGGAATG CGCTCCAGGC ACAAGCCCTG CCACATCCAA CAGTTTGATG GGGATATGCC    60
TCTTACCCTT GCTACACCAC CCGTAGTTAG GTTTACAAAG ATCTTCCTTG CCAAATCTGG   120
AGCAAGCACA CTCAACTTGC AAGTAGCCGG TTGCCTGATT TGGCTCGATC GTGGTAAAGG   180
GAAATGCTCC TACCGCCGCA CCTGCGTCCG TCAAAGAATT TAATGTGGTG GATTTCCCTG   240
AAGATGGCTT ACCCACAATA CCAATCAATG GATCCCTGGG CATACTGGCT CTATTTCCGT   300
TTTATTCTTA CAGACAGCTT ATACTACAAG TTAGTTGGAC AAAAGCTAAA AGACGGAAAA   360
CGAAAACGCA AAATGAAAAT AAAACCAACT CTCATTACAA TTCATCCTAG AACACTTACA   420
CATCTGTTTT GCACTGCATA GCATTACATT TCTTGCATAT CTATCTATTC GAGAAAAAAA   480
AAAAAAGGCA TCGAGTGAAT TTTTCACCTT GATAAAAAAG CCCTTACTAA CCCTACAATA   540
AATTGTGCCG AAACCCTCTG GAGTTTTCTA GAATATTCTA GCCCCATCAG GCTAGAATA    600
TCCTAAAAGT TTATAGTTGA CGAAAATTTT TCAGCGATGA GATGCACATT TATAATGCTA   660
TGATGTTCAA CGCAAAGGAA ATCATAGCGT TATCGGGTAG GTTCGCATCG TTAGCAATAG   720
CTAGTCGCAT ATATACACAG AGATACATAT TATACCTATA CCGTTAAGAA ATAGGATAGA   780
AAATAATGAG CGAACAAAAG GAAGATTTGT TTAAACCAGT AGGAGAAGCT GCTGCAGAGG   840
TCGAAGATGA AAGCATAGCC GAACAGAACA AAGCTAATGA CGGCGTCAAG TTAACCGGCG   900
CACAGGACGC CATGGGCCAT CCAGTGCAAG AGATAGAGTC TCTTTGTATG AATTGTGGAA   960
AGAACGGTAC AACCAGACTT CTTCTGACTT CCATCCCTTA TTTCAGAGAA ATAATTATTA  1020
TGTCATTCGA CTGTCCTCAC TGTGGGTTTA AGAACTGTGA GATCCAACCC GCTTCTCAAA  1080
TTCAAGAGAA GGGCTCTCGT TACGTTTTGA AAGTGGAGTG CCGTGAAGAT TTTAACAGGC  1140
AAGTTATTAA GTCAGAAACT GCCACTTGTA AGTTTGTCGA GCTAGACATT GAGATTCCTG  1200
CTAAGAGAGG TCAATTGACG ACAGTTGAAG GTTTGTTATC CGAGATGATC GACGATCTGT  1260
CGCAAGACCA GGAAATGAGA AAATCTATAG ACGAAGCTCT TTACAAGAAG ATCGATGACT  1320
TCATACAGAA AGTTAAATCC TACATCAATT GTGAACCCAA CACTATTCCG ATTACATTTA  1380
TTTTGGATGA TCCTGCGGGA AATTCCTGGA TCGAATACAA ACCCGGTGAA CCTCAACACA  1440
AATGGTCTCA TACCCAGTAC GTGAGAACCG ACGAACAAAA CGTTCAAGTT GGCATTATTA  1500
CTAGAGACCA GTTGGAGCAA CGTCGCCAAG AACAATTAAA ACAATTGGCC AACCGTGAAA  1560
GAAATCCTTC TGAATCTGTC AAAGTTGGCT CAGCAAACCC ACAGTTTTTG TCAGACGCCA  1620
CCGACATCGA AAACTTTAAC AACGAGGTGC AAACATTCAG AGCTTCTTGT CCATCGTGTA  1680
CCCAAGAGTG TGAAACTCAT ATGAAGCCAG TAAATATCCC ACACTTTAAA GAAGTCATTA  1740
TCATGTCGAC GGTCTGCGAT CATTGTGGTT ATAAGTCTAA TGAGGTGAAG ACCGGTGGTG  1800
CCATCCCTGA CAAAGGAAGA AGGATTACTT TATACTGTGA CGATGCAGCT GACTTGTCCC  1860
GTGATATTTT GAAATCTGAG ACCTGTAGTA TGGTAATTCC TGAATTACAT CTTGATATTC  1920
```

FIG. 5A

| | | | | | |
|---|---|---|---|---|---|
| AAGAAGGTAC | ATTGGGTGGT | AGATTCACCA | CTTTGGAAGG | TTTACTAAGA | CAAGTCTACG | 1980 |
| AAGAACTAGA | ATCCCGTATT | TTCACTCAAA | CTTCGGATTC | CATGGACGAA | GCAACGAAAG | 2040 |
| CCCGCTGGGT | AGAATTTTTT | GCCAAGCTAA | AGGAGGCCAT | CGCTGGGAAA | GTCAAGTTCA | 2100 |
| CAGTCATTAT | GGAAGATCCA | TTGGCCGGGT | CGTACATACA | AAATGTCTAC | GCCCCAGATC | 2160 |
| CGGATCCAAA | CATGACTATC | GAAGATTATG | AAAGAACTAA | AGAGCAAAAT | GAAGACCTGG | 2220 |
| GATTGTCCGA | TATCAAGGTT | GAGTAACGAT | CGTTGGCCTC | GGTATCACCT | CCCCCTTTCC | 2280 |
| TCTTCCTCTT | TACATATATC | CTAACCACAC | AAGCACTCAT | TTGATATGAT | AATACTTATT | 2340 |
| CGTTTTTATT | CAAATAGATA | GCGCAGTCTT | GAAGATTTAC | CTATATTTTT | AAACTTTTGT | 2400 |
| ATAATAGTTG | AAATAGATAA | TACAGCATTT | TTTGGCTCCT | GCTTCATATC | TTTTTTTTTA | 2460 |
| GGTTTTGCT | TTATATTCTT | TCTTTTAACT | CAACTTGTGC | GGAGCAGAGG | TAAAGAGGAC | 2520 |
| AACTATAAAT | GCTGTCAAAA | CGAACAATCT | ACAGATATTT | TTACGAAAAG | GAAAAAGCGC | 2580 |
| AAGAATGAAT | CTTAAACTTT | CTGCTATTGA | AAGTTACTTT | TTCCATAGAA | GCAGACTAAA | 2640 |
| TTTGCATTCA | TGTTTTTATG | TCGGAATCAA | ACTCAACGAA | TTGCCCAAAA | AAAGTCAACT | 2700 |
| GATAGCGGCT | CTTAAGTATA | CTGTAATCCA | ACATGAACGT | TTGACTTGTA | ATGTATTCTA | 2760 |
| TGATGAATTG | AAAAAGGAAA | ACTTCCTACA | AAACATTC | | | 2798 |

(SEQ ID NO: 6)

FIG. 5B

```
CTAGAGTCGA CCTGCAGGTC AACGGATCCA TTTGGATCTA TTTTGGCTGC AATTGTTGAA    60
TCGAAAATCA AAGTTCTTTC AGTTGATGCT CCTTCTTCAT GGGGTAAGTT TACAGTTGAA   120
ATTAGACATA TGGCTTTGTA AAGTGTTTAC CTAATGGAAT ATTTTTTAAC GAAATTTATT   180
TGTTTAGAGA TTGACGAAGG TCCCCAAAAG GAGGGACCTT TAAAGGATTT TGATCCTGAT   240
ACCTTGATCT CCCTAACTGC TCCAAAACCA TGCAGCAAGT TTTATAAGGG AAAACATTAT   300
TTAGGAGGCC GTTTTGTTAG TAAAGCAATT ACTAAAAAGT TCAACCTTTC CCTTCCTCAT   360
TACCCAGGCA TCGACCAGGT TGTTGATATT ACGAACAAGC CCCTCTCAAT GGTTTGAACT   420
GAAACCTGAT TCCTCCCAAT TTGATGAATA TGAGTTTATG ATATACATTC AGTCCACTTA   480
TTTAAGCATT TAACTAATTT TAAAAAAATC GCAGTTAATA GTAGTAAATT ATGATTCGCT   540
CTCATTTCTA GCAGCTGTCA TGTTTTTTA TTTGAGAAGA TGTTTATTTT ATGTAGGTTT   600
ATAAATGTAT GAAAGTTTAC ATACAATAAG TACCACTGCT ATTGGAAAA AAATTTTAAA   660
ATTTTTTAA CCCTTCACAT AGCTGAGCTC ATTTTAAGGT AATTGAGATC TTCAGGATTA   720
GCTTTCAGGT ATTATTCTAC GTTCTATTCG AAGGAATCCA AGGTTTCATG ACTTTCCTTC   780
ATTTGTTTAC TGAGTGCCAC CGCTGGCTAA CCAAAACCAT TCAGTTAACC ATCGTGAATA   840
TTCTGGGGGA TTCTTTTTAA ACAGAATATT TTGGTTTAAA AAAGTAAAAT TTTTGCATTT   900
TACCATATTT TACTTTAGTT TTAATTTTGT TTTTCATTAA AGACAGTTTA TATTGGGTCA   960
TTAAGGAAAA TTTTTTCCAT TCAAGTGAAG ACAAATTTTA TATTGGTACA AGTTATTCTG  1020
TACTTGTCCT TAAACACTTC TAATCAAAAT AACACTAAAA AGAAAATTTG AGAGCATGGC  1080
GGAAGAAAAA AAGGAAGAAT TGTTCACAAG TATTGGCAAT GCTGCACAAA ATGTGTCAAC  1140
AGCTGAGGAT AGGGAAGGAA ATGGTGTTCA AGAAGTCGAA TCGTTGTGTA TGGAGTGTGG  1200
AAAAAACGGT ACTACTAAAT TATTGTTGAC GGTCATTCCA TACTTCCGTG AGGTTGTTTT  1260
AATGTCGTTT GAGTGTCCTC ATTGTGGGTT TAAGAATGCG CAAGTTCAAC ACGCTGAGAC  1320
AATTCAACCG GAAGGAACCA AAATTACTTT CCATGTTGAG GATAAGGAAG ATTTAAATCG  1380
GACAGTTGTA AAGAGCCAGG AGGCTATTGT CAGTATTCCT GAAATTCAGC TAGAAATCCC  1440
GGGAAGGTTA GGCCAGTTAA CTACCATTGA GGGGATTCTG AGTAATGTGG TGGATGATTT  1500
AAGTAAAGAA CAAGAATCTC GTAAGGAGTC TGCTCCTCAG TTATATGACC AAATAAATGC  1560
TTTCATTGAG AAAGTGAATA GTCTACGTTC TGGATCTGTA CCATTTACCA TCACAGTTGA  1620
CGATATTACG GGCAACAGCT GGATCGAGAT GAAACCTGGC CGAGATGGTG ACCGATGGTC  1680
TCAGGTTAGC TACAAGCGTA CTTTGGAGCA GAATACGAAG CTGGGTCTTG TGGATACTGA  1740
TCAACCTGAA GACGTCAAGA CACAAACAAA CAACGCTTCT AATACACTTA AACATGATGC  1800
TACTGCTGTG GAAGTCGATC CCAATGAGGT ACATACCTTC CATGCAACTT GTCCCTCTTG  1860
TTCACATCAA TGTGACACCC ACATGAAGTT GCTTGATATT CCCCATTTCA AGAAGTTAT   1920
```

FIG. 6A

| | | | | | |
|---|---|---|---|---|---|
|TATCATGTCT|ACTGTTTGTG|ATCGTTGTGG|ATATCGTTCC|AACGAAGTAA|AGACTGGTGG|1980|
|TGAAATTCCA|CCCAAAGGTC|GAAAAATTAC|TTTAAAGGTC|ATGGATGCCG|AGGACTTATC|2040|
|CCGTGATATT|CTCAAATCTG|AAACCGCATC|TCTTAAAATT|CCTGAACTTG|GACTTGATTT|2100|
|GTTCCCAGGT|ACTTTGGGTG|GACGATTCAC|AACCATTGAA|GGTCTTCTAG|CTCAAGTTTA|2160|
|TGATGAGTTA|TATGCCCGTG|TGTTTTCTCA|GGAGACCGAT|TCTATGACTC|CTGAGCAAGT|2220|
|CGCTAACTGG|CAACAATTTC|TCTGCAACTT|GACGGCTGCA|CGTGAGGGTG|CTACTCAATT|2280|
|CACTCTTATT|TTAGATGATC|CTCTTTCACA|AAGTTATCTG|CAGAATTATT|ACGCTCCCGA|2340|
|TCCAGATCCA|AATATGACTA|TTGAGGAGTA|TGAACGTTCA|TTCCAAGTAA|ATGAGGAATT|2400|
|GGGTCTGAAC|GATATGAAGA|CAGAAAACTA|TGAAAGGAT|GGAGGTAAGA|AGTAAAGTTC|2460|
|GAGGTTTTTG|TCAAATGTTA|GGGAATGTAT|TTAATATAGT|AATACTATGT|TTTTTTGGGG|2520|
|GGTTTATTGA|CTATGAAGAT|ATAATAGTAT|AGTAGATTAG|CTAATTTTA|TTTCCCGTAA|2580|
|TGTTTTTGTT|AGAGACTGAT|GCTTTATTAT|TTTACTTTTA|GTTTAAAATA|GTTACTTGAT|2640|
|TTATCGCAAA|TGTTATGAGG|CTAATAATTC|GAAGTATTAG|TAAACCATAA|AATTTGCTAC|2700|
|AAGAAATGTT|AGATAGTGAA|GCTAAAATTA|TTACCAATAA|CAAACTTGTA|ACACATATTT|2760|
|AGCCGATACC|AGAAATAATT|GATTCATATT|TCACAATTTC|ATTATTTGTA|TACCATGTTT|2820|
|AGTGAAGAGT|AACAATGGTG|CGTAATTTAA|AGAACGCGAC|ACGCTATAAT|AGTAATAGAA|2880|
|TTTAATTTAT|ATATACATCT|AGATATTTCT|CAACACATAC|CATTGGTATA|AACAGCACTT|2940|
|TCCTTTTTTT|TTTGTTTGAA|TCCTTATCCC|TCTTTTCCTA|CCCTTTCTTC|TATTTTAGTA|3000|
|ATCTCTTTTT|TAATAATTGC|TAATATATTT|AATGATTCAG|CAACCAACAA|CTGCTAAACC|3060|
|TAGAATTTCT|ACTTCTTCAA|AGTTAAATAC|TGTTTTATCA|AAAAACAAAG|AGAATGTTCC|3120|
|TGGAAAGTTG|TTTAAAAAGT|TTAAATGCCC|TTCTTTAGTG|ATTTCAGAAA|AGCGAAAAGA|3180|
|GCTTCCTTTA|CGCAAAAAGC|CAAGAGTTAA|CTACAGCGAA|TATGGTTCTG|TTGATGGGAA|3240|
|GTATGATTCA|GCTTACGTAT|CTGAAAATGT|GTCTGGGTTG|GCAACCATCA|AAGAAGCTAA|3300|
|CCGATTAATA|CTAAATCATG|AACGACGAGA|TCCCTCAACA|GTCATTAAGA|AACAGTTCTC|3360|
|TGTGCCTAAA|CCTATCAAGG|GTCATGAAGA|TATATCTAAA|CTGTGTGCAC|ATCGTCCACC|3420|
|TCCTACACTG|GGAATGAAAA|GGAAGGTGGA|TTTTATTCCT|CGTCCCCTTT|ACGATCCTGC|3480|
|TGATGAATTT|GCTATCGTTT|TATATGATCC|CACTACTGAT|GCAGATGAGA|TCATTCCTGA|3540|
|TATAAAAGAG|GTTTTAGCGG|AAAAACGTAA|AAAAGATGAA|TTGTTAAAAA|ATCGAAAAGG|3600|
|AAAGAAAGAA|ATTTCTGATA|GTGAGCCTGA|AAGTGACCAT|GATTCATGTG|TCTCCACTGA|3660|
|CACAGTGGCT|AGCTGTTCTA|CCGAGCAAAG|TCTCATAACC|TCTAATACCT|CAAAGCATAG|3720|
|AAGACCAAAT|AAAAGTTTGA|AAGATCTACT|AGGAATTCAG|AAAGAAAAAC|CTCCACCTCC|3780|
|TCCTGTTGCT|GTTGTCATTG|ATCCAAAACT|TACTCGTATT|CTAAGACCTC|ATCAAATAGA|3840|

FIG. 6B

```
AGGTGTCAAA TTCTTGTACA AGTGTGTAAC TGGAAGGATT GACCGTTGTG CAAATGGATG    3900
TATTATGGCA GATGAGATGG GACTTGGTAA GACACTTCAA TGTATTGCTT TGTTATGGAC    3960
CCTTTTAAAA CAGTCTCCTC AGGCTGGAAA ACCGACAATT GAAAAGGCAA TTATAACTTG    4020
TCCTTCTTCT TTAGTCAAAA ATTGGGCTAA TGAACTTGTC AAATGGTTAG GAAAAGATGC    4080
TATTACTCCA TTCATATTGG ACGGTAAAAG CTCCAAACAG GAGTTAATCA TGGCTTTGCA    4140
ACAATGGGCA TCCGTACATG GACGACAAGT CACACGTCCA GTGCTTATTG CCAGTTATGA    4200
GACCCTTAGA AGTTATGTTG AGCATCTCAA CAACGCAGAA ATTGAATGC TTCTTTGTGA     4260
CGAAGGTCAT CGTCTTAAGA ATAGTGATTC TTTGACTTTT ACGGCATTAG ACAAGCTAAA    4320
CGTTCAAAGG CGTGTCATCC TTTCTGGTAC CCCTATTCAA AATGATCTAA GCGAATACTT    4380
TTCGTTGTTA AATTTTGCGA ATCCTGGTTT GTTAGGTTCA AGGCAAGAGT TCAGAAAAAA    4440
TTATGAAATT CCAATTTTAA AAGGTCGTGA TGCTGACGGA ACAGAAAAAG ATAAGGAGAA    4500
TGGTGATGCT AAGTTAGCTG AGTTAGCCAA GATTGTCAAT CGGTTTATTA TTCGTCGTAC    4560
GAATGATATT CTCTCCAAAT ATTTGCCTGT TAAATACGAA CATGTTGTCT TTTGCAACCT    4620
TTCCGAATTT CAGCTTTCTT TGTACAAGCA TTTTATTACC TCGCCTGAAA TCAATAAAAT    4680
CTTAAGGGGG ACCGGCAGTC AACCACTAAA AGCTATAGGT CTGCTAAAAA AAATATGTAA    4740
TCATCCTGAT CTATTGAATT TAACTGAGGA CTTGGAAGGT TGTGAGGCTC TATTCCCTCC    4800
AGGATTTATT CCCCGTGAGC TAAGAGGGCG CGATAGAAAC ATTGACTCCT CTTTATCAGG    4860
TAAAATGTTA GTGTTGGAAC GAATGCTCTA TCAAATAAAA CAAGAGACAG ACGATAAAAT    4920
TGTTTTAATT AGCAATTACA CCTCCACGCT TGACTTGTTT GAGCAGCTTT GTAGAGCTCG    4980
CGGTTACAAG GCTCTTCGGC TAGATGGTAC TATGAATGTA AATAAACGAC AACGTTAGT    5040
TGACACATTC AATGACCCGG AAAAGGATGC TTTTGTGTTT TTATTATCTT CTAAAGCAGG    5100
TGGTTGTGGT ATTAACCTTA TTGGCGCTAA TCGTCTTATT CTGTTTGATC CCGATTGGAA    5160
TCCAGCCGCC GATCAACAAG CTT                                            5183
(SEQ ID NO: 7)
```

FIG. 6C

```
GGCACGAGCTGAATTGCGCGTGGTGGCCATGGCGGCCAGCGGGGCTGTGGAACCAGGGCC      60
CCCGGGGCTGCCGTGCCGTGCGCCCCGTGCGAGGAGGCCCGCCCGCAGCCCTGATCACCT     120
GTTCCGGCCCATCAGCAGCGCCGAATGGCCTCCTTTCCTGCAGCAGCCCGAGATCGAGTCGCTATG  180
CATGAACTGTTACTGCAATGTGAGCTCCTTTCCTGCGAGCACTGTGGCTGGAACAACACGGAGATCCAG  240
AGAAATAATAGTGAGCAGGATCCAGGAGACCAGGGAGTGCGCTACACTTTGTCTGTCAGGGCTCTGA  300
GTCGGCAGGCAGGATCCAGGAGACCAGGGAGTGCGCTACACTTTGTCTGTCAGGGCTCTGA   360
GGACATGAACAGAGAAGTGTGAAGACTGAAGAAGGAGCTCTGACCACTGTTGAAGATTCCTGAGCTAGA  420
TTTGAAATTCCTGCCTTTAGCCAGACAGGACCCAGCCTGCACGAAGGGCAAACAAGATGCTAC  480
CCGTGCTATCTCTGGCCTGGAGTTCATTGTCAAACTGAAGGAGCTAAAGCAAGTAGCCTCCC  540
AGCTGAAAGAATTGATGAGTTCATTGTCAAACTGAAGGAGCTAAAGCAAGTAGCCTCCC      600
TTTCACTCTGTGATCATTGATGATGCCCTGGTGATCACACAACCGGAACAGTTTTGTGGAAAACCCACATGCTCC  660
TCAGAAAGATGATGCCCTGGTGATCACACAACCGGACACCGAGCAGCAGGAAGAGAT        720
GCTGGGGCTTCAAGAAGAAGCACCAGCAGAGAAGCCAGAAGAGGAAGATCTCAGAAATGA    780
AGTGCTCCAGTTCAGCACACAAATGCCCAGAAGAGGTTATCATCATGCTCAGACCAACATGAA  840
GCTAGTACAAATCCCTCACTTTAAGGAGTGTATCATCATGCTCCGAGAACTG             900
TGGGCATCGGACCAATGAGTGAAATCTGAGATATGACCAGAGACCTCCTCAAGTCTGAGACTTG  960
CACCCTCCACATCACAGATGCCTCAGATATTGAACTGGAATGGCAGTCCTCGGGGCAAGTT  1020
CAGTGTGGAAATCCCAGAGCTAGAATTTGAAAGACATCCGGGAACTGTGTGACCAAATCCTTTCAC  1080
CACCACACTGGAAGGGCTGCTGAAAGACATCCGGGAACTGTGTGACCAAATCCTTTCAC      1140
ACTGGGCGACAGTTCCAATCCTGGACAGAGACGGAGAGACTACAGAGAGTTTAGCCAGAAGAT  1200
GGACCAGATCATCGAAGTAACATGAAGGCCCTGAAGATGATCCTGAAGATGAAGGTGGAGCGTTA  1260
CAGTTACTTGCAGAATGTGTATGCCTGAAGATCTCAATGAGGCTAGGGCTGGGTGGCTCAAGGGCTA  1320
CAAGGCCACCTTTGACCAAAATGAGGAGCTAGCAGTGGCTCAAGAAGAACATGAAGAAGGCCAGCTTCCAGCGC  1380
TGAGGCAGGCCTGGCTCGTAGGTTATTATTAGTATTGGATGAAGGCGAAGGCTGGGAGTGTCTTTC  1440
TGCTCTTTCTGGCTCTGTAGGTTATTATTAGTATTGGATGAAGGCGAAGGCTGGGAGTGTCTTTC  1500
CCACCAGCCCTTGCCATGTGCCCATGGTGGGGAGGACATCTGGTTTGAGTCAGAGATCTGTGCACAC  1560
TTTTAAACAGCTTGTGATGCAAGTGTGAGCTGCCTATTGTGTTACTTGACCTTATTTTGAA   1620
GTTTGAATTGGCCTAGGAGGAAACCCAGAAATGAACCAGGGTATGTCATCACTTTTT        1680
CATATCAAGTCCTCACCCTCCTTCCACATAAATGCTTTATCCTTTAAGGTTGAACTTTGA   1740
AGTTGGAGAAGGTGGAATAAAGTTACACCTGAAAAAAAAAAAAAAAAAAAAAAAAAAAAA   1800
AAAAAAAAAAAAAAAA
(SEQ ID NO: 8)
```

FIG. 7

```
                    *        *    Zinc Finger    *        *
NH2       QPTEIESLCMNCYRNGTTRLLLTKIPFFREIIVSSFSCEHCGWNNTEIQSAGRIQDQGVRYTLTVRSQEDMNRE
COOH      EVLQFNTN.PE.NAPAQ.NMK.VQ..H.K.V.IMATN.N..HRTN.VK.G.AVEPL.T.I..HITDPS..T.D
Consensus                C  C      T   L  IPFEI    CE CG    E SG   G R TL      DM R NH2       VVKTDSATTRIPELDFEIPAFSQKGALTTVEGLISRAISGLEQDQPTRRAVEGAIAER--IDEFIGKLKDLKQM
COOH      LL.SETCSVE....E..LGMAVLG.KF..L...L-KD.RE.VTKN.FTLGDSSNPDQSEKLQ..SQ..GQIIEG
Consensus        K      IPEL FE     G  TT EGL    I  L   P              EF  KL NH2       ASPFTLVIDDPSGNSFVENPHAPQKDNALVITYYDRTPQQAEMLGLQAEAPEE-KAEEEDLR    (SEQ ID NO: 9)
COOH      KMKAHFIMN..A...YLQ.VY..ED.PEMKVER.K..FD.NEE...NDMKT.GYE.GLAPQ.    (SEQ ID NO:10)
Consensus     DP GNS    N AP D      Y RT  Q   LGL    E A    R             (SEQ ID NO:11)
```

FIG. 8

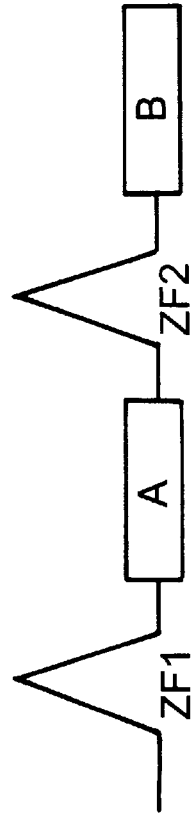

FIG. 9

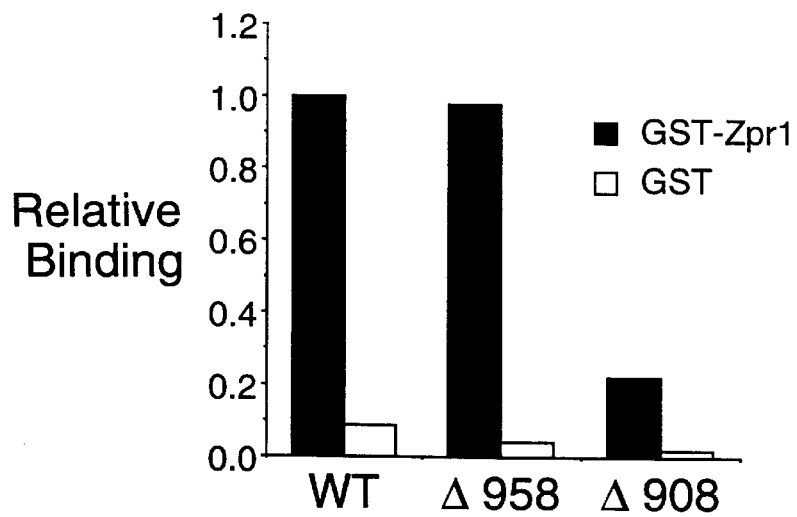

FIG. 10

```
              αG              αH              αI
             ┌──┐            ┌──┐            ┌──┐
              X                              XI
HER-1    IPASEISSILEKGERLPQPPICTIDVYMIMVKCWMIDADSRPKFRELIIEF   (SEQ ID NO:16)
HER-2    ...R..PDL.......................SEC..R....VS..       (SEQ ID NO:17)
HER-3    LRLA.VPDL.......A.Q.........V........ENI..T.K..AN..  (SEQ ID NO:18)
HER-4    ..TR..PDL............................K..AA..          (SEQ ID NO:19)
PDGF-Rα  MVD.TFYNKIKS.Y.MAK.DHA.SE..E......NSEPEK...S.YH.SEIV  (SEQ ID NO:20)
PDGF-Rβ  PMNEQFYNAIKR.Y.MA..AHASDEI.E..Q...EEKFEI..P.SQ.VLLL   (SEQ ID NO:21)
FGF-R1   V.VE.LFKL.KE.H.MDK.SN..NEL..M.RD..HAVPSQ..T.KQ.VEDL   (SEQ ID NO:22)
TrkA     LSNT.AIDCITQ.RE.ER.RA.PPE...A..RG..QREPQQ.HSIKDVHARL  (SEQ ID NO:23)
INS-R    LSNEQVLKFVMD.GY.D..DN.PER.TDL.RM..QFNPNM..T.L.IVNLL   (SEQ ID NO:24)
IGF1-R   LSNEQVLRFVME.GL.DK.DN.PDMLFEL.RM..QYNPKM...S.L.I.SSI  (SEQ ID NO:25)

Consensus            G              M  CW         R            (SEQ ID NO;35)
```

FIG. 11

(SEQ ID NO:36)

```
                        SEQUENCE LISTING ( 1 ) GENERAL INFORMATION:

( i i i ) NUMBER OF SEQUENCES: 35

( 2 ) INFORMATION FOR SEQ ID NO:1:

( i ) SEQUENCE CHARACTERISTICS:
            ( A ) LENGTH: 459 amino acids
            ( B ) TYPE: amino acid
            ( D ) TOPOLOGY: linear ( i i ) MOLECULE TYPE: protein ( v ) FRAGMENT TYPE: internal ( x i ) SEQUENCE DESCRIPTION: SEQ ID NO:1:

Met Ser Ala Ser Gly Ala Val Gln Pro Gly His Pro Gly Ala Ala Val
   1               5                  10                  15

Gly Pro Ser Pro Ala Ala Ala Ala Ser Pro Ala Thr Gly Pro Leu Phe
                  20                  25                  30

Arg Pro Leu Ser Ala Glu Asp Glu Glu Gln Gln Pro Thr Glu Ile Glu
                  35                  40                  45

Ser Leu Cys Met Asn Cys Tyr Arg Asn Gly Thr Thr Arg Leu Leu Leu
              50                  55                  60

Thr Lys Ile Pro Phe Phe Arg Glu Ile Ile Val Ser Ser Phe Ser Cys
  65                  70                  75                  80
```

```
Glu His Cys Gly Trp Asn Asn Thr Glu Ile Gln Ser Ala Gly Arg Ile
                85                  90                  95

Gln Asp Gln Gly Val Arg Tyr Thr Leu Thr Val Arg Ser Gln Glu Asp
            100                 105                 110

Met Asn Arg Glu Val Val Lys Thr Asp Ser Ala Thr Thr Arg Ile Pro
        115                 120                 125

Glu Leu Asp Phe Glu Ile Pro Ala Phe Ser Gln Lys Gly Ala Leu Thr
    130                 135                 140

Thr Val Glu Gly Leu Ile Ser Arg Ala Ile Ser Gly Leu Glu Gln Asp
145                 150                 155                 160

Gln Pro Thr Arg Arg Ala Val Glu Gly Ala Ile Ala Glu Arg Ile Asp
            165                 170                 175

Glu Phe Ile Gly Lys Leu Lys Asp Leu Lys Gln Met Ala Ser Pro Phe
        180                 185                 190

Thr Leu Val Ile Asp Asp Pro Ser Gly Asn Ser Phe Val Glu Asn Pro
    195                 200                 205

His Ala Pro Gln Lys Asp Asn Ala Leu Val Ile Thr Tyr Tyr Asp Arg
    210                 215                 220

Thr Pro Gln Gln Ala Glu Met Leu Gly Leu Gln Ala Glu Ala Pro Glu
225                 230                 235                 240

Glu Lys Ala Glu Glu Asp Leu Arg Asn Glu Val Leu Gln Phe Asn
            245                 250                 255

Thr Asn Cys Pro Glu Cys Asn Ala Pro Ala Gln Thr Asn Met Lys Leu
        260                 265                 270

Val Gln Ile Pro His Phe Lys Glu Val Ile Met Ala Thr Asn Cys
    275                 280                 285

Glu Asn Cys Gly His Arg Thr Asn Glu Val Lys Ser Gly Gly Ala Val
    290                 295                 300

Glu Pro Leu Gly Thr Arg Ile Thr Leu His Ile Thr Asp Pro Ser Asp
305                 310                 315                 320

Met Thr Arg Asp Leu Leu Lys Ser Glu Thr Cys Ser Val Glu Ile Pro
            325                 330                 335

Glu Leu Glu Phe Glu Leu Gly Met Ala Val Leu Gly Gly Lys Phe Thr
        340                 345                 350

Thr Leu Glu Gly Leu Leu Lys Asp Ile Arg Glu Leu Val Thr Lys Asn
        355                 360                 365

Pro Phe Thr Leu Gly Asp Ser Ser Asn Pro Asp Gln Ser Glu Lys Leu
    370                 375                 380

Gln Glu Phe Ser Gln Lys Leu Gly Gln Ile Ile Glu Gly Lys Met Lys
385                 390                 395                 400

Ala His Phe Ile Met Asn Asp Pro Ala Gly Asn Ser Tyr Leu Gln Asn
            405                 410                 415

Val Tyr Ala Pro Glu Asp Asp Pro Glu Met Lys Val Glu Arg Tyr Lys
        420                 425                 430

Arg Thr Phe Asp Gln Asn Glu Glu Leu Gly Leu Asn Asp Met Lys Thr
        435                 440                 445

Glu Gly Tyr Glu Ala Gly Leu Ala Pro Gln Arg
450                 455
```

(2) INFORMATION FOR SEQ ID NO:2:

(i) SEQUENCE CHARACTERISTICS:
        (A) LENGTH: 459 amino acids
        (B) TYPE: amino acid
        (D) TOPOLOGY: linear (ii) MOLECULE TYPE: protein (xi) SEQUENCE DESCRIPTION: SEQ ID NO:2:

| | | | | | | | | | | | | | | |
|---|---|---|---|---|---|---|---|---|---|---|---|---|---|---|
| Met | Ala | Ala | Ser | Gly | Ala | Val | Glu | Pro | Pro | Gly | Ala | Ala | Val |
| 1 | | | | 5 | | | | | 10 | | | | 15 |
| Ala | Pro | Ser | Pro | Ala | Pro | Ala | Pro | Pro | Ala | Pro | Asp | His | Leu | Phe |
| | | | 20 | | | | | 25 | | | | 30 | | |
| Arg | Pro | Ile | Ser | Ala | Glu | Asp | Glu | Glu | Gln | Gln | Pro | Thr | Glu | Ile | Glu |
| | | 35 | | | | | 40 | | | | | 45 | | | |
| Ser | Leu | Cys | Met | Asn | Cys | Tyr | Cys | Asn | Gly | Met | Thr | Arg | Leu | Leu | Leu |
| 50 | | | | | 55 | | | | | 60 | | | | | |
| Thr | Lys | Ile | Pro | Phe | Phe | Arg | Glu | Ile | Ile | Val | Ser | Ser | Phe | Ser | Cys |
| 65 | | | | | 70 | | | | | 75 | | | | | 80 |
| Glu | His | Cys | Gly | Trp | Asn | Asn | Thr | Glu | Ile | Gln | Ser | Ala | Gly | Arg | Ile |
| | | | | 85 | | | | | 90 | | | | | 95 | |
| Gln | Asp | Gln | Gly | Val | Arg | Tyr | Thr | Leu | Ser | Val | Arg | Ala | Leu | Glu | Asp |
| | | | 100 | | | | | 105 | | | | 110 | | | |
| Met | Asn | Arg | Glu | Val | Val | Lys | Thr | Asp | Ser | Ala | Ala | Thr | Arg | Ile | Pro |
| | | | 115 | | | | | 120 | | | | 125 | | | |
| Glu | Leu | Asp | Phe | Glu | Ile | Pro | Ala | Phe | Ser | Gln | Lys | Gly | Ala | Leu | Thr |
| | 130 | | | | | 135 | | | | | 140 | | | | |
| Thr | Val | Glu | Gly | Leu | Ile | Thr | Arg | Ala | Ile | Ser | Gly | Leu | Glu | Gln | Asp |
| 145 | | | | | 150 | | | | | 155 | | | | | 160 |
| Gln | Pro | Ala | Arg | Arg | Ala | Asn | Lys | Asp | Ala | Thr | Ala | Glu | Arg | Ile | Asp |
| | | | | 165 | | | | | 170 | | | | | 175 | |
| Glu | Phe | Ile | Val | Lys | Leu | Lys | Glu | Leu | Lys | Gln | Val | Ala | Ser | Pro | Phe |
| | | | 180 | | | | | 185 | | | | 190 | | | |
| Thr | Leu | Ile | Ile | Asp | Asp | Pro | Ser | Gly | Asn | Ser | Phe | Val | Glu | Asn | Pro |
| | | 195 | | | | | 200 | | | | | 205 | | | |
| His | Ala | Pro | Gln | Lys | Asp | Asp | Ala | Leu | Val | Ile | Thr | His | Tyr | Asn | Arg |
| | 210 | | | | | 215 | | | | | 220 | | | | |
| Thr | Arg | Gln | Gln | Glu | Glu | Met | Leu | Gly | Leu | Gln | Glu | Glu | Ala | Pro | Ala |
| 225 | | | | | 230 | | | | | 235 | | | | | 240 |
| Glu | Lys | Pro | Glu | Glu | Glu | Asp | Leu | Arg | Asn | Glu | Val | Leu | Gln | Phe | Ser |
| | | | | 245 | | | | | 250 | | | | | 255 | |
| Thr | Asn | Cys | Pro | Glu | Cys | Asn | Ala | Pro | Ala | Gln | Thr | Asn | Met | Lys | Leu |
| | | | 260 | | | | | 265 | | | | 270 | | | |
| Val | Gln | Ile | Pro | His | Phe | Lys | Glu | Val | Ile | Ile | Met | Ala | Thr | Asn | Cys |
| | | | 275 | | | | | 280 | | | | 285 | | | |
| Glu | Asn | Cys | Gly | His | Arg | Thr | Asn | Glu | Val | Lys | Ser | Gly | Gly | Ala | Val |
| | 290 | | | | | 295 | | | | | 300 | | | | |
| Glu | Pro | Leu | Gly | Thr | Arg | Ile | Thr | Leu | His | Ile | Thr | Asp | Ala | Ser | Asp |
| 305 | | | | | 310 | | | | | 315 | | | | | 320 |
| Met | Thr | Arg | Asp | Leu | Leu | Lys | Ser | Glu | Thr | Cys | Ser | Val | Glu | Ile | Pro |
| | | | | 325 | | | | | 330 | | | | | 335 | |
| Glu | Leu | Glu | Phe | Glu | Leu | Gly | Met | Ala | Val | Leu | Gly | Gly | Lys | Phe | Thr |
| | | | 340 | | | | | 345 | | | | 350 | | | |
| Thr | Leu | Glu | Gly | Leu | Leu | Lys | Asp | Ile | Arg | Glu | Leu | Val | Thr | Lys | Asn |
| | | 355 | | | | | 360 | | | | | 365 | | | |
| Pro | Phe | Thr | Leu | Gly | Asp | Ser | Ser | Asn | Pro | Gly | Gln | Thr | Glu | Arg | Leu |
| | 370 | | | | | 375 | | | | | 380 | | | | |
| Gln | Glu | Phe | Ser | Gln | Lys | Met | Asp | Gln | Ile | Ile | Glu | Gly | Asn | Met | Lys |
| 385 | | | | | 390 | | | | | 395 | | | | | 400 |

```
Ala His Phe Ile Met Asp Asp Pro Ala Gly Asn Ser Tyr Leu Gln Asn
            405                 410                 415

Val Tyr Ala Pro Glu Asp Pro Glu Met Lys Val Glu Arg Tyr Lys
            420                 425                 430

Arg Thr Phe Asp Gln Asn Glu Glu Leu Gly Leu Asn Asp Met Lys Thr
            435                 440                 445

Glu Gly Tyr Glu Ala Gly Leu Ala Pro Gln Arg
            450                 455
```

(2) INFORMATION FOR SEQ ID NO:3:

(i) SEQUENCE CHARACTERISTICS:
        (A) LENGTH: 486 amino acids
        (B) TYPE: amino acid
        (D) TOPOLOGY: linear (ii) MOLECULE TYPE: protein (xi) SEQUENCE DESCRIPTION: SEQ ID NO:3:

```
Met Ser Glu Gln Lys Glu Asp Leu Phe Lys Pro Val Gly Glu Ala Ala
 1               5                  10                  15

Ala Glu Val Glu Asp Glu Ser Ile Ala Glu Gln Asn Lys Ala Asn Asp
                20                  25                  30

Gly Val Lys Leu Thr Gly Ala Gln Asp Ala Met Gly His Pro Val Gln
            35                  40                  45

Glu Ile Glu Ser Leu Cys Met Asn Cys Gly Lys Asn Gly Thr Thr Arg
 50                  55                  60

Leu Leu Leu Thr Ser Ile Pro Tyr Phe Arg Glu Ile Ile Met Ser
 65                  70                  75                  80

Phe Asp Cys Pro His Cys Gly Phe Lys Asn Cys Glu Ile Gln Pro Ala
                85                  90                  95

Ser Gln Ile Gln Glu Lys Gly Ser Arg Tyr Val Leu Lys Val Glu Cys
            100                 105                 110

Arg Glu Asp Phe Asn Arg Gln Val Ile Lys Ser Glu Thr Ala Thr Cys
            115                 120                 125

Lys Phe Val Glu Leu Asp Ile Glu Ile Pro Ala Lys Arg Gly Gln Leu
130                 135                 140

Thr Thr Val Glu Gly Leu Leu Ser Glu Met Ile Asp Asp Leu Ser Gln
145                 150                 155                 160

Asp Gln Glu Met Arg Lys Ser Ile Asp Glu Ala Leu Tyr Lys Lys Ile
                165                 170                 175

Asp Asp Phe Ile Gln Lys Val Lys Ser Tyr Ile Asn Cys Glu Pro Asn
            180                 185                 190

Thr Ile Pro Ile Thr Phe Ile Leu Asp Asp Pro Ala Gly Asn Ser Trp
            195                 200                 205

Ile Glu Tyr Lys Pro Gly Glu Pro Gln His Lys Trp Ser His Thr Gln
210                 215                 220

Tyr Val Arg Thr Asp Glu Gln Asn Val Gln Val Gly Ile Ile Thr Arg
225                 230                 235                 240

Asp Gln Leu Glu Gln Arg Arg Gln Glu Gln Leu Lys Gln Leu Ala Asn
                245                 250                 255

Arg Glu Arg Asn Pro Ser Glu Ser Val Lys Val Gly Ser Ala Asn Pro
            260                 265                 270

Gln Phe Leu Ser Asp Ala Thr Asp Ile Glu Asn Phe Asn Asn Glu Val
            275                 280                 285

Gln Thr Phe Arg Ala Ser Cys Pro Ser Cys Thr Gln Glu Cys Glu Thr
            290                 295                 300
```

```
His Met Lys Pro Val Asn Ile Pro His Phe Lys Glu Val Ile Met
305                 310                 315                 320

Ser Thr Val Cys Asp His Cys Gly Tyr Lys Ser Asn Glu Val Lys Thr
            325                 330                 335

Gly Gly Ala Ile Pro Asp Lys Gly Arg Arg Ile Thr Leu Tyr Cys Asp
            340                 345                 350

Asp Ala Ala Asp Leu Ser Arg Asp Ile Leu Lys Ser Glu Thr Cys Ser
            355                 360                 365

Met Val Ile Pro Glu Leu His Leu Asp Ile Gln Glu Gly Thr Leu Gly
370                 375                 380

Gly Arg Phe Thr Thr Leu Glu Gly Leu Leu Arg Gln Val Tyr Glu Glu
385                 390                 395                 400

Leu Glu Ser Arg Ile Phe Thr Gln Thr Ser Asp Ser Met Asp Glu Ala
            405                 410                 415

Thr Lys Ala Arg Trp Val Glu Phe Phe Ala Lys Leu Lys Glu Ala Ile
            420                 425                 430

Ala Gly Lys Val Lys Phe Thr Val Ile Met Glu Asp Pro Leu Ala Gly
            435                 440                 445

Ser Tyr Ile Gln Asn Val Tyr Ala Pro Asp Pro Asp Pro Asn Met Thr
            450                 455                 460

Ile Glu Asp Tyr Glu Arg Thr Lys Glu Gln Asn Glu Glu Leu Gly Leu
465                 470                 475                 480

Ser Asp Ile Lys Val Glu
                485
```

(2) INFORMATION FOR SEQ ID NO:4:

(i) SEQUENCE CHARACTERISTICS:
       (A) LENGTH: 459 amino acids
       (B) TYPE: amino acid
       (D) TOPOLOGY: linear (ii) MOLECULE TYPE: protein (xi) SEQUENCE DESCRIPTION: SEQ ID NO:4:

```
Met Ala Glu Glu Lys Lys Glu Glu Leu Phe Thr Ser Ile Gly Asn Ala
1               5                   10                  15

Ala Gln Asn Val Ser Thr Ala Glu Asp Arg Glu Gly Asn Gly Val Gln
            20                  25                  30

Glu Val Glu Ser Leu Cys Met Glu Cys Gly Lys Asn Gly Thr Thr Lys
        35                  40                  45

Leu Leu Leu Thr Val Ile Pro Tyr Phe Arg Glu Val Val Leu Met Ser
    50                  55                  60

Phe Glu Cys Pro His Cys Gly Phe Lys Asn Ala Gln Val Gln His Ala
65                  70                  75                  80

Glu Thr Ile Gln Pro Glu Gly Thr Lys Ile Thr Phe His Val Glu Asp
            85                  90                  95

Lys Glu Asp Leu Asn Arg Thr Val Val Lys Ser Gln Glu Ala Ile Val
            100                 105                 110

Ser Ile Pro Glu Ile Gln Leu Glu Ile Pro Gly Arg Leu Gly Gln Leu
            115                 120                 125

Thr Thr Val Glu Gly Leu Leu Ser Asn Val Val Asp Asp Leu Ser Lys
            130                 135                 140

Glu Gln Glu Ser Arg Lys Glu Ser Ala Pro Gln Leu Tyr Asp Gln Ile
145                 150                 155                 160
```

Asn Ala Phe Ile Glu Lys Val Asn Ser Leu Arg Ser Gly Ser Val Pro
            165                 170                 175

Phe Thr Ile Thr Val Asp Asp Ile Thr Gly Asn Ser Trp Ile Glu Met
            180                 185                 190

Lys Pro Gly Arg Asp Gly Asp Arg Trp Ser Gln Val Ser Tyr Lys Arg
            195                 200                 205

Thr Leu Glu Gln Asn Thr Lys Leu Gly Leu Val Asp Thr Asp Gln Pro
    210                 215                 220

Glu Asp Val Lys Thr Gln Thr Asn Asn Ala Ser Asn Thr Leu Lys His
225                 230                 235                 240

Asp Ala Thr Ala Val Glu Val Asp Pro Asn Glu Val His Thr Phe His
            245                 250                 255

Ala Thr Cys Pro Ser Cys Ser His Gln Cys Asp Thr His Met Lys Leu
            260                 265                 270

Leu Asp Ile Pro His Phe Lys Glu Val Ile Ile Met Ser Thr Val Cys
            275                 280                 285

Asp Arg Cys Gly Tyr Arg Ser Asn Glu Val Lys Thr Gly Gly Glu Ile
            290                 295                 300

Pro Pro Lys Gly Arg Lys Ile Thr Leu Lys Val Met Asp Ala Glu Asp
305                 310                 315                 320

Leu Ser Arg Asp Ile Leu Lys Ser Glu Thr Ala Ser Leu Lys Ile Pro
            325                 330                 335

Glu Leu Gly Leu Asp Leu Phe Pro Gly Thr Leu Gly Gly Arg Phe Thr
            340                 345                 350

Thr Ile Glu Gly Leu Leu Ala Gln Val Tyr Asp Glu Leu Tyr Ala Arg
            355                 360                 365

Val Phe Ser Gln Glu Thr Asp Ser Met Thr Pro Glu Gln Val Ala Asn
    370                 375                 380

Trp Gln Gln Phe Leu Cys Asn Leu Thr Ala Ala Arg Glu Gly Ala Thr
385                 390                 395                 400

Gln Phe Thr Leu Ile Leu Asp Asp Pro Leu Ser Gln Ser Tyr Leu Gln
            405                 410                 415

Asn Tyr Tyr Ala Pro Asp Pro Asp Pro Asn Met Thr Ile Glu Glu Tyr
            420                 425                 430

Glu Arg Ser Phe Gln Val Asn Glu Glu Leu Gly Leu Asn Asp Met Lys
    435                 440                 445

Thr Glu Asn Tyr Glu Lys Asp Gly Gly Lys Lys
    450                 455

(2) INFORMATION FOR SEQ ID NO:5:

(i) SEQUENCE CHARACTERISTICS:
        (A) LENGTH: 2162 base pairs
        (B) TYPE: nucleic acid
        (C) STRANDEDNESS: single
        (D) TOPOLOGY: linear (ix) FEATURE:
        (A) NAME/KEY: Coding Sequence
        (B) LOCATION: 89...1465

(xi) SEQUENCE DESCRIPTION: SEQ ID NO:5:

CCGCTCCCCG TTCCTCCACA ACCACAACCT TTCTTTTTCA AAGAAGATTT GCCCCGGGGA    60

AGCCGCCGCG GGAGCAACGC GTGGGGAG ATG TCT GCC AGC GGG GCT GTG CAG    112
                            Met Ser Ala Ser Gly Ala Val Gln
                             1               5

```
CCG GGA CAC CCG GGG GCC GCC GTC GGG CCC TCG CCC GCT GCG GCT GCG        160
Pro Gly His Pro Gly Ala Ala Val Gly Pro Ser Pro Ala Ala Ala Ala
         10              15              20

TCA CCA GCC ACC GGG CCT TTG TTC CGG CCC CTC AGC GCC GAA GAT GAG        208
Ser Pro Ala Thr Gly Pro Leu Phe Arg Pro Leu Ser Ala Glu Asp Glu
 25              30              35                      40

GAG CAA CAG CCC ACC GAG ATC GAG TCA CTG TGC ATG AAC TGT TAC CGG        256
Glu Gln Gln Pro Thr Glu Ile Glu Ser Leu Cys Met Asn Cys Tyr Arg
                 45              50                      55

AAC GGC ACG ACG CGA CTT CTG CTC ACC AAG ATC CCC TTC TTT AGA GAA        304
Asn Gly Thr Thr Arg Leu Leu Leu Thr Lys Ile Pro Phe Phe Arg Glu
             60              65                  70

ATC ATC GTG AGC TCC TTT TCC TGC GAA CAC TGT GGC TGG AAC AAC ACG        352
Ile Ile Val Ser Ser Phe Ser Cys Glu His Cys Gly Trp Asn Asn Thr
             75              80              85

GAG ATC CAG TCT GCA GGC AGG ATC CAG GAC CAG GGA GTG CGC TAC ACC        400
Glu Ile Gln Ser Ala Gly Arg Ile Gln Asp Gln Gly Val Arg Tyr Thr
 90              95             100

TTG ACC GTG AGA AGC CAA GAG GAC ATG AAC AGA GAA GTG GTA AAG ACA        448
Leu Thr Val Arg Ser Gln Glu Asp Met Asn Arg Glu Val Val Lys Thr
105             110             115             120

GAC TCT GCC ACC ACA AGG ATC CCC GAG CTG GAT TTT GAG ATT CCA GCC        496
Asp Ser Ala Thr Thr Arg Ile Pro Glu Leu Asp Phe Glu Ile Pro Ala
                125             130             135

TTC AGC CAG AAG GGA GCT CTG ACC ACT GTT GAA GGA CTC ATC AGC CGT        544
Phe Ser Gln Lys Gly Ala Leu Thr Thr Val Glu Gly Leu Ile Ser Arg
            140             145             150

GCG ATC TCT GGC CTG GAA CAG GAT CAG CCC ACA CGA CGG GCA GTG GAA        592
Ala Ile Ser Gly Leu Glu Gln Asp Gln Pro Thr Arg Arg Ala Val Glu
            155             160             165

GGT GCC ATC GCA GAG AGA ATT GAT GAG TTC ATT GGC AAA CTG AAG GAC        640
Gly Ala Ile Ala Glu Arg Ile Asp Glu Phe Ile Gly Lys Leu Lys Asp
170             175             180

CTA AAG CAA ATG GCT TCC CCT TTC ACA CTG GTC ATT GAT GAT CCC TCG        688
Leu Lys Gln Met Ala Ser Pro Phe Thr Leu Val Ile Asp Asp Pro Ser
185             190             195             200

GGA AAC AGC TTT GTA GAA AAC CCA CAT GCT CCC CAG AAA GAT AAT GCC        736
Gly Asn Ser Phe Val Glu Asn Pro His Ala Pro Gln Lys Asp Asn Ala
                205             210             215

TTG GTG ATC ACA TAC TAT GAC CGA ACC CCA CAG CAA GCT GAG ATG CTG        784
Leu Val Ile Thr Tyr Tyr Asp Arg Thr Pro Gln Gln Ala Glu Met Leu
            220             225             230

GGG CTC CAA GCA GAA GCA CCA GAG GAG AAG GCG GAA GAG GAA GAC CTT        832
Gly Leu Gln Ala Glu Ala Pro Glu Glu Lys Ala Glu Glu Glu Asp Leu
            235             240             245

AGA AAC GAA GTG CTC CAG TTC AAC ACT AAC TGC CCA GAG TGC AAC GCT        880
Arg Asn Glu Val Leu Gln Phe Asn Thr Asn Cys Pro Glu Cys Asn Ala
250             255             260

CCG GCT CAG ACC AAC ATG AAG CTT GTC CAA ATC CCC CAC TTT AAA GAG        928
Pro Ala Gln Thr Asn Met Lys Leu Val Gln Ile Pro His Phe Lys Glu
265             270             275             280

GTT ATC ATC ATG GCC ACC AAC TGT GAG AAT TGT GGG CAT CGG ACT AAT        976
Val Ile Ile Met Ala Thr Asn Cys Glu Asn Cys Gly His Arg Thr Asn
                285             290             295

GAG GTG AAG TCC GGA GGA GCT GTA GAA CCT TTG GGT ACC AGG ATC ACC       1024
Glu Val Lys Ser Gly Gly Ala Val Glu Pro Leu Gly Thr Arg Ile Thr
            300             305             310

CTC CAC ATC ACA GAT CCC TCA GAC ATG ACC AGA GAC CTC CTC AAG TCT       1072
Leu His Ile Thr Asp Pro Ser Asp Met Thr Arg Asp Leu Leu Lys Ser
315             320             325
```

```
GAG ACC TGT AGT GTG GAA ATC CCA GAG CTT GAG TTT GAA CTG GGA ATG    1120
Glu Thr Cys Ser Val Glu Ile Pro Glu Leu Glu Phe Glu Leu Gly Met
        330                 335                 340

GCT GTA CTT GGG GGC AAG TTC ACC ACT CTA GAA GGA CTG CTG AAA GAC    1168
Ala Val Leu Gly Gly Lys Phe Thr Thr Leu Glu Gly Leu Leu Lys Asp
345                 350                 355                 360

ATC CGA GAA CTG GTA ACC AAG AAC CCA TTC ACA CTG GGC GAC AGC TCT    1216
Ile Arg Glu Leu Val Thr Lys Asn Pro Phe Thr Leu Gly Asp Ser Ser
                365                 370                 375

AAT CCT GAC CAG TCA GAG AAA CTG CAG GAG TTT AGC CAG AAG TTG GGC    1264
Asn Pro Asp Gln Ser Glu Lys Leu Gln Glu Phe Ser Gln Lys Leu Gly
            380                 385                 390

CAG ATC ATC GAG GGC AAG ATG AAG GCC CAC TTT ATC ATG AAT GAT CCA    1312
Gln Ile Ile Glu Gly Lys Met Lys Ala His Phe Ile Met Asn Asp Pro
        395                 400                 405

GCA GGA AAC AGT TAT CTG CAG AAT GTG TAT GCA CCT GAA GAC GAT CCA    1360
Ala Gly Asn Ser Tyr Leu Gln Asn Val Tyr Ala Pro Glu Asp Asp Pro
410                 415                 420

GAG ATG AAG GTC GAG CGG TAC AAA CGC ACC TTT GAC CAA AAT GAG GAG    1408
Glu Met Lys Val Glu Arg Tyr Lys Arg Thr Phe Asp Gln Asn Glu Glu
425                 430                 435                 440

CTC GGG CTC AAT GAC ATG AAG ACA GAG GGC TAT GAG GCG GGC CTG GCC    1456
Leu Gly Leu Asn Asp Met Lys Thr Glu Gly Tyr Glu Ala Gly Leu Ala
                445                 450                 455

CCA CAG CGG TAGCAGTGGC CAGCTCACTG GCCAGCTACA GTGCCACTCA CACTGCAGG  1514
Pro Gln Arg

GTTATCTGTT ACTGTGGGGA ACTGACGAGG AGTGCTCAAG CCCTCGTCCA TGGTGAAGAG  1574

GTTACCACTT GAGTTAGAAA TGTAAGCACC CAAGATTAGC AGCTGACGGA CGAGGCAGCT  1634

GCAGCCCTAC TGTGCTCCTT GACCTTCTTT TGGAGGTTTT AAAGTCGGCG TGAGAAGAAT  1694

CCCAGAAACA CCAGGCGGTC TGCCATCACC GTTTGCCTGT CAGCTCTCTG ACCTCCAGTG  1754

CTGGACCTTT GAAGTCTGGG GAAGTGAAAT ACAAGTTTCT GCTGGCTCTG GGCATGTGAA  1814

GTACTGACTC AGCAGGGCAA GGATGTCGGA GGGGCCGAGC AGGCACAGGT GAAGACGCCA  1874

CATTAAAGTG ATGGCCTTTA AACGAAAGGA GAACAACTAT CCAGACTCCT ACCTCCCACA  1934

TGGAAGAAAC CGCCACCTCA TCAAGTTAAT AAAGAAAAAG AAAAGAAGGG AGGTCCAGAG  1994

TCATTCCCAC ATTCTGTTGG AGGAGGAGAA AAGGATGTTC ACTACTTGGT GCATACAGGC  2054

ATGCACACGG ACAGACAGGT GCGTGCACAC ACACAACCAC ACACAAACAC AGGTTTGCTG  2114

ATGGAACATT ATTATACAAT TCTGAGCTTA CATAAAAAAA AAAAAAA                2162

(2) INFORMATION FOR SEQ ID NO:6:

(i) SEQUENCE CHARACTERISTICS:
        (A) LENGTH: 2798 base pairs
        (B) TYPE: nucleic acid
        (C) STRANDEDNESS: single
        (D) TOPOLOGY: linear (xi) SEQUENCE DESCRIPTION: SEQ ID NO:6:

TGCCGGAATG CGCTCCAGGC ACAAGCCCTG CCACATCCAA CAGTTTGATG GGGATATGCC    60

TCTTACCCTT GCTACACCAC CCGTAGTTAG GTTTACAAAG ATCTTCCTTG CCAAATCTGG   120

AGCAAGCACA CTCAACTTGC AAGTAGCCGG TTGCCTGATT TGGCTCGATC GTGGTAAAGG   180

GAAATGCTCC TACCGCCGCA CCTGCGTCCG TCAAAGAATT TAATGTGGTG GATTTCCCTG   240

AAGATGGCTT ACCCACAATA CCAATCAATG GATCCCTGGG CATACTGGCT CTATTTCCGT   300

TTTATTCTTA CAGACAGCTT ATACTACAAG TTAGTTGGAC AAAAGCTAAA AGACGGAAAA   360
```

```
CGAAAACGCA AAATGAAAAT AAAACCAACT CTCATTACAA TTCATCCTAG AACACTTACA    420

CATCTGTTTT GCACTGCATA GCATTACATT TCTTGCATAT CTATCTATTC GAGAAAAAAA    480

AAAAAGGCA TCGAGTGAAT TTTTCACCTT GATAAAAAAG CCCTTACTAA CCCTACAATA     540

AATTGTGCCG AAACCCTCTG GAGTTTTCTA GAATATTCTA GCCCCATCAG GGCTAGAATA    600

TCCTAAAAGT TTATAGTTGA CGAAAATTTT TCAGCGATGA GATGCACATT TATAATGCTA    660

TGATGTTCAA CGCAAAGGAA ATCATAGCGT TATCGGGTAG GTTCGCATCG TTAGCAATAG    720

CTAGTCGCAT ATATACACAG AGATACATAT TATACCTATA CCGTTAAGAA ATAGGATAGA    780

AAATAATGAG CGAACAAAAG GAAGATTTGT TTAAACCAGT AGGAGAAGCT GCTGCAGAGG    840

TCGAAGATGA AAGCATAGCC GAACAGAACA AAGCTAATGA CGGCGTCAAG TTAACCGGCG    900

CACAGGACGC CATGGGCCAT CCAGTGCAAG AGATAGAGTC TCTTTGTATG AATTGTGGAA    960

AGAACGGTAC AACCAGACTT CTTCTGACTT CCATCCCTTA TTTCAGAGAA ATAATTATTA   1020

TGTCATTCGA CTGTCCTCAC TGTGGGTTTA AGAACTGTGA GATCCAACCC GCTTCTCAAA   1080

TTCAAGAGAA GGGCTCTCGT TACGTTTTGA AAGTGGAGTG CCGTGAAGAT TTTAACAGGC   1140

AAGTTATTAA GTCAGAAACT GCCACTTGTA AGTTTGTCGA GCTAGACATT GAGATTCCTG   1200

CTAAGAGAGG TCAATTGACG ACAGTTGAAG GTTTGTTATC CGAGATGATC GACGATCTGT   1260

CGCAAGACCA GGAAATGAGA AAATCTATAG ACGAAGCTCT TTACAAGAAG ATCGATGACT   1320

TCATACAGAA AGTTAAATCC TACATCAATT GTGAACCCAA CACTATTCCG ATTACATTTA   1380

TTTTGGATGA TCCTGCGGGA AATTCCTGGA TCGAATACAA ACCCGGTGAA CCTCAACACA   1440

AATGGTCTCA TACCCAGTAC GTGAGAACCG ACGAACAAAA CGTTCAAGTT GGCATTATTA   1500

CTAGAGACCA GTTGGAGCAA CGTCGCCAAG AACAATTAAA ACAATTGGCC AACCGTGAAA   1560

GAAATCCTTC TGAATCTGTC AAAGTTGGCT CAGCAAACCC ACAGTTTTTG TCAGACGCCA   1620

CCGACATCGA AAACTTTAAC AACGAGGTGC AAACATTCAG AGCTTCTTGT CCATCGTGTA   1680

CCCAAGAGTG TGAAACTCAT ATGAAGCCAG TAAATATCCC ACACTTTAAA GAAGTCATTA   1740

TCATGTCGAC GGTCTGCGAT CATTGTGGTT ATAAGTCTAA TGAGGTGAAG ACCGGTGGTG   1800

CCATCCCTGA CAAAGGAAGA AGGATTACTT TATACTGTGA CGATGCAGCT GACTTGTCCC   1860

GTGATATTTT GAAATCTGAG ACCTGTAGTA TGGTAATTCC TGAATTACAT CTTGATATTC   1920

AAGAAGGTAC ATTGGGTGGT AGATTCACCA CTTTGGAAGG TTTACTAAGA CAAGTCTACG   1980

AAGAACTAGA ATCCCGTATT TTCACTCAAA CTTCGGATTC CATGGACGAA GCAACGAAAG   2040

CCCGCTGGGT AGAATTTTTT GCCAAGCTAA AGGAGGCCAT CGCTGGGAAA GTCAAGTTCA   2100

CAGTCATTAT GGAAGATCCA TTGGCCGGGT CGTACATACA AAATGTCTAC GCCCCAGATC   2160

CGGATCCAAA CATGACTATC GAAGATTATG AAAGAACTAA AGAGCAAAAT GAAGACCTGG   2220

GATTGTCCGA TATCAAGGTT GAGTAACGAT CGTTGGCCTC GGTATCACCT CCCCCTTTCC   2280

TCTTCCTCTT TACATATATC CTAACCACAC AAGCACTCAT TTGATATGAT AATACTTATT   2340

CGTTTTTATT CAAATAGATA GCGCAGTCTT GAAGATTTAC CTATATTTTT AAACTTTTGT   2400

ATAATAGTTG AAATAGATAA TACAGCATTT TTTGGCTCCT GCTTCATATC TTTTTTTTTA   2460

GGTTTTTGCT TTATATTCTT TCTTTTAACT CAACTTGTGC GGAGCAGAGG TAAAGAGGAC   2520

AACTATAAAT GCTGTCAAAA CGAACAATCT ACAGATATTT TTACGAAAAG GAAAAAGCGC   2580

AAGAATGAAT CTTAAACTTT CTGCTATTGA AAGTTACTTT TTCCATAGAA GCAGACTAAA   2640

TTTGCATTCA TGTTTTTATG TCGGAATCAA ACTCAACGAA TTGCCCAAAA AAAGTCAACT   2700
```

```
GATAGCGGCT CTTAAGTATA CTGTAATCCA ACATGAACGT TTGACTTGTA ATGTATTCTA    2760

TGATGAATTG AAAAAGGAAA ACTTCCTACA AAACATTC                            2798

(2) INFORMATION FOR SEQ ID NO:7:

(i) SEQUENCE CHARACTERISTICS:
         (A) LENGTH: 5183 base pairs
         (B) TYPE: nucleic acid
         (C) STRANDEDNESS: single
         (D) TOPOLOGY: linear (xi) SEQUENCE DESCRIPTION: SEQ ID NO:7:

CTAGAGTCGA CCTGCAGGTC AACGGATCCA TTTGGATCTA TTTTGGCTGC AATTGTTGAA      60

TCGAAAATCA AGTTCTTTC AGTTGATGCT CCTTCTTCAT GGGGTAAGTT TACAGTTGAA      120

ATTAGACATA TGGCTTTGTA AAGTGTTTAC CTAATGGAAT ATTTTTTAAC GAAATTTATT    180

TGTTTAGAGA TTGACGAAGG TCCCCAAAAG GAGGGACCTT TAAAGGATTT TGATCCTGAT    240

ACCTTGATCT CCCTAACTGC TCCAAAACCA TGCAGCAAGT TTTATAAGGG AAAACATTAT    300

TTAGGAGGCC GTTTTGTTAG TAAAGCAATT ACTAAAAAGT TCAACCTTTC CCTTCCTCAT    360

TACCCAGGCA TCGACCAGGT TGTTGATATT ACGAACAAGC CCCTCTCAAT GGTTTGAACT    420

GAAACCTGAT TCCTCCCAAT TTGATGAATA TGAGTTTATG ATATACATTC AGTCCACTTA    480

TTTAAGCATT TAACTAATTT TAAAAAAATC GCAGTTAATA GTAGTAAATT ATGATTCGCT    540

CTCATTTCTA GCAGCTGTCA TGTTTTTTTA TTTGAGAAGA TGTTTATTTT ATGTAGGTTT    600

ATAAATGTAT GAAAGTTTAC ATACAATAAG TACCACTGCT ATTTGGAAAA AAATTTTAAA    660

ATTTTTTTAA CCCTTCACAT AGCTGAGCTC ATTTTAAGGT AATTGAGATC TTCAGGATTA    720

GCTTTCAGGT ATTATTCTAC GTTCTATTCG AAGGAATCCA AGGTTTCATG ACTTTCCTTC    780

ATTTGTTTAC TGAGTGCCAC CGCTGGCTAA CCAAAACCAT TCAGTTAACC ATCGTGAATA    840

TTCTGGGGGA TTCTTTTTAA ACAGAATATT TTGGTTTAAA AAAGTAAAAT TTTTGCATTT    900

TACCATATTT TACTTTAGTT TTAATTTTGT TTTTCATTAA AGACAGTTTA TATTGGGTCA    960

TTAAGGAAAA TTTTTTCCAT TCAAGTGAAG ACAAATTTTA TATTGGTACA AGTTATTCTG   1020

TACTTGTCCT TAAACACTTC TAATCAAAAT AACACTAAAA AGAAAATTTG AGAGCATGGC   1080

GGAAGAAAAA AAGGAAGAAT TGTTCACAAG TATTGGCAAT GCTGCACAAA ATGTGTCAAC   1140

AGCTGAGGAT AGGGAAGGAA ATGGTGTTCA AGAAGTCGAA TCGTTGTGTA TGGAGTGTGG   1200

AAAAAACGGT ACTACTAAAT TATTGTTGAC GGTCATTCCA TACTTCCGTG AGGTTGTTTT   1260

AATGTCGTTT GAGTGTCCTC ATTGTGGGTT TAAGAATGCG CAAGTTCAAC ACGCTGAGAC   1320

AATTCAACCG GAAGGAACCA AAATTACTTT CCATGTTGAG GATAAGGAAG ATTTAAATCG   1380

GACAGTTGTA AAGAGCCAGG AGGCTATTGT CAGTATTCCT GAAATTCAGC TAGAAATCCC   1440

GGGAAGGTTA GGCCAGTTAA CTACCATTGA GGGGATTCTG AGTAATGTGG TGGATGATTT   1500

AAGTAAAGAA CAAGAATCTC GTAAGGAGTC TGCTCCTCAG TTATATGACC AAATAAATGC   1560

TTTCATTGAG AAAGTGAATA GTCTACGTTC TGGATCTGTA CCATTTACCA TCACAGTTGA   1620

CGATATTACG GGCAACAGCT GGATCGAGAT GAAACCTGGC CGAGATGGTG ACCGATGGTC   1680

TCAGGTTAGC TACAAGCGTA CTTTGGAGCA GAATACGAAG CTGGGTCTTG TGGATACTGA   1740

TCAACCTGAA GACGTCAAGA CACAAACAAA CAACGCTTCT AATACACTTA AACATGATGC   1800

TACTGCTGTG GAAGTCGATC CAATGAGGT ACATACCTTC CATGCAACTT GTCCCTCTTG   1860

TTCACATCAA TGTGACACCC ACATGAAGTT GCTTGATATT CCCCATTTCA AGAAGTTAT    1920

TATCATGTCT ACTGTTTGTG ATCGTTGTGG ATATCGTTCC AACGAAGTAA AGACTGGTGG   1980
```

```
TGAAATTCCA CCCAAAGGTC GAAAAATTAC TTTAAAGGTC ATGGATGCCG AGGACTTATC      2040

CCGTGATATT CTCAAATCTG AAACCGCATC TCTTAAAATT CCTGAACTTG GACTTGATTT      2100

GTTCCCAGGT ACTTTGGGTG GACGATTCAC AACCATTGAA GGTCTTCTAG CTCAAGTTTA      2160

TGATGAGTTA TATGCCCGTG TGTTTTCTCA GGAGACCGAT TCTATGACTC CTGAGCAAGT      2220

CGCTAACTGG CAACAATTTC TCTGCAACTT GACGGCTGCA CGTGAGGGTG CTACTCAATT      2280

CACTCTTATT TTAGATGATC CTCTTTCACA AAGTTATCTG CAGAATTATT ACGCTCCCGA      2340

TCCAGATCCA AATATGACTA TTGAGGAGTA TGAACGTTCA TTCCAAGTAA ATGAGGAATT      2400

GGGTCTGAAC GATATGAAGA CAGAAAACTA TGAAAAGGAT GGAGGTAAGA AGTAAAGTTC      2460

GAGGTTTTTG TCAAATGTTA GGGAATGTAT TTAATATAGT AATACTATGT TTTTTTGGGG      2520

GGTTTATTGA CTATGAAGAT ATAATAGTAT AGTAGATTAG CTAATTTTTA TTTCCCGTAA      2580

TGTTTTTGTT AGAGACTGAT GCTTTATTAT TTTACTTTTA GTTTAAAATA GTTACTTGAT      2640

TTATCGCAAA TGTTATGAGG CTAATAATTC GAAGTATTAG TAAACCATAA AATTTGCTAC      2700

AAGAAATGTT AGATAGTGAA GCTAAAATTA TTACCAATAA CAAACTTGTA ACACATATTT      2760

AGCCGATACC AGAAATAATT GATTCATATT TCACAATTTC ATTATTTGTA TACCATGTTT      2820

AGTGAAGAGT AACAATGGTG CGTAATTTAA AGAACGCGAC ACGCTATAAT AGTAATAGAA      2880

TTTAATTTAT ATATACATCT AGATATTTCT CAACACATAC CATTGGTATA AACAGCACTT      2940

TCCTTTTTTT TTTGTTTGAA TCCTTATCCC TCTTTTCCTA CCCTTTCTTC TATTTTAGTA      3000

ATCTCTTTTT TAATAATTGC TAATATATTT AATGATTCAG CAACCAACAA CTGCTAAACC      3060

TAGAATTTCT ACTTCTTCAA AGTTAAATAC TGTTTTATCA AAAAACAAAG AGAATGTTCC      3120

TGGAAAGTTG TTTAAAAAGT TTAAATGCCC TTCTTTAGTG ATTTCAGAAA AGCGAAAAGA      3180

GCTTCCTTTA CGCAAAAAGC CAAGAGTTAA CTACAGCGAA TATGGTTCTG TTGATGGGAA      3240

GTATGATTCA GCTTACGTAT CTGAAAATGT GTCTGGGTTG GCAACCATCA AGAAGCTAA       3300

CCGATTAATA CTAAATCATG AACGACGAGA TCCCTCAACA GTCATTAAGA AACAGTTCTC      3360

TGTGCCTAAA CCTATCAAGG GTCATGAAGA TATATCTAAA CTGTGTGCAC ATCGTCCACC      3420

TCCTACACTG GGAATGAAAA GGAAGGTGGA TTTTATTCCT CGTCCCCTTT ACGATCCTGC      3480

TGATGAATTT GCTATCGTTT TATATGATCC CACTACTGAT GCAGATGAGA TCATTCCTGA      3540

TATAAAAGAG GTTTTAGCGG AAAAACGTAA AAAAGATGAA TTGTTAAAAA ATCGAAAAGG      3600

AAAGAAAGAA ATTTCTGATA GTGAGCCTGA AAGTGACCAT GATTCATGTG TCTCCACTGA      3660

CACAGTGGCT AGCTGTTCTA CCGAGCAAAG TCTCATAACC TCTAATACCT CAAAGCATAG      3720

AAGACCAAAT AAAAGTTTGA AAGATCTACT AGGAATTCAG AAAGAAAAC CTCCACCTCC       3780

TCCTGTTGCT GTTGTCATTG ATCCAAAACT TACTCGTATT CTAAGACCTC ATCAAATAGA      3840

AGGTGTCAAA TTCTTGTACA AGTGTGTAAC TGGAAGGATT GACCGTTGTG CAAATGGATG      3900

TATTATGGCA GATGAGATGG GACTTGGTAA GACACTTCAA TGTATTGCTT TGTTATGGAC      3960

CCTTTTAAAA CAGTCTCCTC AGGCTGAAAA ACCGACAATT GAAAAGGCAA TTATAACTTG      4020

TCCTTCTTCT TTAGTCAAAA ATTGGGCTAA TGAACTTGTC AAATGGTTAG GAAAAGATGC      4080

TATTACTCCA TTCATATTGG ACGGTAAAAG CTCCAAACAG GAGTTAATCA TGGCTTTGCA      4140

ACAATGGGCA TCCGTACATG GACGACAAGT CACACGTCCA GTGCTTATTG CCAGTTATGA      4200

GACCCTTAGA AGTTATGTTG AGCATCTCAA CAACGCAGAA ATTGGAATGC TTCTTTGTGA      4260

CGAAGGTCAT CGTCTTAAGA ATAGTGATTC TTTGACTTTT ACGGCATTAG ACAAGCTAAA      4320

CGTTCAAAGG CGTGTCATCC TTTCTGGTAC CCCTATTCAA AATGATCTAA GCGAATACTT      4380
```

```
TTCGTTGTTA AATTTTGCGA ATCCTGGTTT GTTAGGTTCA AGGCAAGAGT TCAGAAAAAA    4440

TTATGAAATT CCAATTTTAA AAGGTCGTGA TGCTGACGGA ACAGAAAAAG ATAAGGAGAA    4500

TGGTGATGCT AAGTTAGCTG AGTTAGCCAA GATTGTCAAT CGGTTTATTA TTCGTCGTAC    4560

GAATGATATT CTCTCCAAAT ATTTGCCTGT TAAATACGAA CATGTTGTCT TTTGCAACCT    4620

TTCCGAATTT CAGCTTTCTT TGTACAAGCA TTTTATTACC TCGCCTGAAA TCAATAAAAT    4680

CTTAAGGGGG ACCGGCAGTC AACCACTAAA AGCTATAGGT CTGCTAAAAA AAATATGTAA    4740

TCATCCTGAT CTATTGAATT TAACTGAGGA CTTGGAAGGT TGTGAGGCTC TATTCCCTCC    4800

AGGATTTATT CCCCGTGAGC TAAGAGGGCG CGATAGAAAC ATTGACTCCT CTTTATCAGG    4860

TAAAATGTTA GTGTTGGAAC GAATGCTCTA TCAAATAAAA CAAGAGACAG ACGATAAAAT    4920

TGTTTTAATT AGCAATTACA CCTCCACGCT TGACTTGTTT GAGCAGCTTT GTAGAGCTCG    4980

CGGTTACAAG GCTCTTCGGC TAGATGGTAC TATGAATGTA AATAAACGAC AACGTTTAGT    5040

TGACACATTC AATGACCCGG AAAAGGATGC TTTTGTGTTT TTATTATCTT CTAAAGCAGG    5100

TGGTTGTGGT ATTAACCTTA TTGGCGCTAA TCGTCTTATT CTGTTTGATC CCGATTGGAA    5160

TCCAGCCGCC GATCAACAAG CTT                                           5183

(2) INFORMATION FOR SEQ ID NO:8:

(i) SEQUENCE CHARACTERISTICS:
        (A) LENGTH: 1817 base pairs
        (B) TYPE: nucleic acid
        (C) STRANDEDNESS: single
        (D) TOPOLOGY: linear (xi) SEQUENCE DESCRIPTION: SEQ ID NO:8:

GGCACGAGCT GAATTGCGCG TGGTGGCCAT GGCGGCCAGC GGGGCTGTGG AACCAGGGCC      60

CCCGGGGGCT GCCGTCGCCC CGTCGCCCGC CCCGGCCCCG CCGCCTGCCC CTGATCACCT     120

GTTCCGGCCC ATCAGCGCCG AGGACGAGGA GCAGCAGCCC ACCGAGATCG AGTCGCTATG     180

CATGAACTGT TACTGCAATG GCATGACGCG CCTCCTGCTC ACCAAGATTC CCTTCTTCAG     240

AGAAATAATA GTGAGCTCCT TTTCCTGCGA GCACTGTGGC TGGAACAACA CGGAGATCCA     300

GTCGGCAGGC AGGATCCAGG ACCAGGGAGT GCGCTACACT TTGTCTGTCA GGGCTCTGGA     360

GGACATGAAC AGAGAAGTGG TGAAGACTGA CTCTGCTGCC ACAAGGATTC CTGAGCTAGA     420

TTTTGAAATT CCTGCCTTTA GCCAGAAAGG AGCTCTGACC ACTGTTGAAG GATTGATCAC     480

CCGTGCTATC TCTGGCCTGG AGCAGGACCA GCCTGCACGA AGGGCAAACA AAGATGCTAC     540

AGCTGAAAGA ATTGATGAGT TCATTGTCAA ACTGAAGGAG CTAAAGCAAG TAGCCTCCCC     600

TTTCACTCTG ATCATTGATG ATCCCTCAGG GAACAGTTTT GTGGAAAACC CACATGCTCC     660

TCAGAAAGAT GATGCCCTGG TGATCACACA CTACAACCGG ACCCGACAGC AGGAAGAGAT     720

GCTGGGGCTT CAAGAAGAAG CACCAGCAGA GAAGCCAGAA GAGGAAGATC TCAGAAATGA     780

AGTGCTCCAG TTCAGCACAA ACTGCCCAGA ATGCAATGCC CCCGCTCAGA CCAACATGAA     840

GCTAGTACAA ATCCCTCACT TTAAGGAGGT TATCATCATG GCTACCAACT GCGAGAACTG     900

TGGGCATCGG ACCAATGAGG TGAAATCTGG AGGAGCAGTA GAACCCTTGG GCACCAGGAT     960

CACCCTCCAC ATCACAGATG CCTCAGATAT GACCAGAGAC CTCCTCAAGT CTGAGACTTG    1020

CAGTGTGGAA ATCCCAGAGC TAGAATTTGA ACTGGGAATG GCAGTCCTCG GGGCAAGTT     1080

CACCACACTG GAAGGGCTGC TGAAAGACAT CCGGGAACTG GTGACCAAAA ATCCTTTCAC    1140

ACTGGGCGAC AGTTCCAATC CTGGACAGAC GGAGAGACTA CAGGAGTTTA GCCAGAAGAT    1200
```

-continued

```
GGACCAGATC ATCGAAGGTA ACATGAAGGC CCACTTTATT ATGGATGATC CAGCAGGAAA    1260

CAGTTACTTG CAGAATGTGT ATGCGCCTGA AGATGATCCT GAGATGAAGG TGGAGCGTTA    1320

CAAGCGCACC TTTGACCAAA ATGAGGAGCT AGGGCTCAAT GACATGAAGA CAGAGGGCTA    1380

TGAGGCAGGC CTGGCTCCGC AACGGTAGCA GTGGGTGGCT CAAGGGCCAG CCTCCAGCGC    1440

TGCTCTTTCT GTAGGTTATT TATTAGTATT GGATGAAGGC GAAGGCTGGG AGTGTCTTTC    1500

CCACCAGCCC TTGCCCATGG TGGGGAGGAC ATCTGGTTTG AGTCAGAGAT CTGTGCACAC    1560

TTTTTAAACA GCTTGTGATG CAAGTGTGAG CCTATTGTGT TACTTGACCT TATTTTGGAA    1620

GTTTTGAATT GGCCTAGGAG GAAACCCAGA AATGAACCAG GGGTATGTCA TCACTTTTTT    1680

CATATCAAGT CCTCACCCTC CTTCCACATA ATGCTTTATC CTTTAAGGTT GGAACTTTGA    1740

AGTTGGAGAA GGTGGAATAA AGTTACACCT GGAAAAAAAA AAAAAAAAAA AAAAAAAAAA    1800

AAAAAAAAAA AAAAAA                                                   1817
```

(2) INFORMATION FOR SEQ ID NO:9:

(i) SEQUENCE CHARACTERISTICS:
       (A) LENGTH: 207 amino acids
       (B) TYPE: amino acid
       (D) TOPOLOGY: linear (ii) MOLECULE TYPE: protein (xi) SEQUENCE DESCRIPTION: SEQ ID NO:9:

```
Gln Pro Thr Glu Ile Glu Ser Leu Cys Met Asn Cys Tyr Arg Asn Gly
 1               5                  10                  15

Thr Thr Arg Leu Leu Leu Thr Lys Ile Pro Phe Phe Arg Glu Ile Ile
            20                  25                  30

Val Ser Ser Phe Ser Cys Glu His Cys Gly Trp Asn Asn Thr Glu Ile
        35                  40                  45

Gln Ser Ala Gly Arg Ile Gln Asp Gln Gly Val Arg Tyr Thr Leu Thr
    50                  55                  60

Val Arg Ser Gln Glu Asp Met Asn Arg Glu Val Lys Thr Asp Ser
65                  70                  75                  80

Ala Thr Thr Arg Ile Pro Glu Leu Asp Phe Glu Ile Pro Ala Phe Ser
                85                  90                  95

Gln Lys Gly Ala Leu Thr Thr Val Glu Gly Leu Ile Ser Arg Ala Ile
            100                 105                 110

Ser Gly Leu Glu Gln Asp Gln Pro Thr Arg Arg Ala Val Glu Gly Ala
        115                 120                 125

Ile Ala Glu Arg Ile Asp Glu Phe Ile Gly Lys Leu Lys Asp Leu Lys
    130                 135                 140

Gln Met Ala Ser Pro Phe Thr Leu Val Ile Asp Asp Pro Ser Gly Asn
145                 150                 155                 160

Ser Phe Val Glu Asn Pro His Ala Pro Gln Lys Asp Asn Ala Leu Val
                165                 170                 175

Ile Thr Tyr Tyr Asp Arg Thr Pro Gln Gln Ala Glu Met Leu Gly Leu
            180                 185                 190

Gln Ala Glu Ala Pro Glu Glu Lys Ala Glu Glu Asp Leu Arg
        195                 200                 205
```

(2) INFORMATION FOR SEQ ID NO:10:

(i) SEQUENCE CHARACTERISTICS:
       (A) LENGTH: 209 amino acids
       (B) TYPE: amino acid
       (D) TOPOLOGY: linear (ii) MOLECULE TYPE: protein (xi) SEQUENCE DESCRIPTION: SEQ ID NO:10:

```
Glu Val Leu Gln Phe Asn Thr Asn Cys Pro Glu Cys Asn Ala Pro Ala
  1               5                  10                  15

Gln Thr Asn Met Lys Leu Val Gln Ile Pro His Phe Lys Glu Val Ile
             20                  25                  30

Ile Met Ala Thr Asn Cys Glu Asn Cys Gly His Arg Thr Asn Glu Val
             35                  40                  45

Lys Ser Gly Gly Ala Val Glu Pro Leu Gly Thr Arg Ile Thr Leu His
 50                  55                  60

Ile Thr Asp Pro Ser Asp Met Thr Arg Asp Leu Leu Lys Ser Glu Thr
 65                  70                  75                  80

Cys Ser Val Glu Ile Pro Glu Leu Glu Phe Glu Leu Gly Met Ala Val
             85                  90                  95

Leu Gly Gly Lys Phe Thr Thr Leu Glu Gly Leu Leu Lys Asp Ile Arg
            100                 105                 110

Glu Leu Val Thr Lys Asn Pro Phe Thr Leu Gly Asp Ser Ser Asn Pro
            115                 120                 125

Asp Gln Ser Glu Lys Leu Gln Glu Phe Ser Gln Lys Leu Gly Gln Ile
130                 135                 140

Ile Glu Gly Lys Met Lys Ala His Phe Ile Met Asn Asp Pro Ala Gly
145                 150                 155                 160

Asn Ser Tyr Leu Gln Asn Val Tyr Ala Pro Glu Asp Pro Glu Met
            165                 170                 175

Lys Val Glu Arg Tyr Lys Arg Thr Phe Asp Gln Asn Glu Glu Leu Gly
            180                 185                 190

Leu Asn Asp Met Lys Thr Glu Gly Tyr Glu Ala Gly Leu Ala Pro Gln
            195                 200                 205

Arg
```

(2) INFORMATION FOR SEQ ID NO:11:

(i) SEQUENCE CHARACTERISTICS:
        (A) LENGTH: 210 amino acids
        (B) TYPE: amino acid
        (D) TOPOLOGY: linear (ii) MOLECULE TYPE: protein (xi) SEQUENCE DESCRIPTION: SEQ ID NO:11:

```
Xaa Xaa Xaa Xaa Xaa Xaa Xaa Xaa Cys Xaa Xaa Cys Xaa Xaa Xaa Xaa
  1               5                  10                  15

Xaa Thr Xaa Xaa Xaa Leu Xaa Xaa Ile Pro Xaa Phe Xaa Glu Xaa Ile
             20                  25                  30

Xaa Xaa Xaa Xaa Xaa Cys Glu Xaa Cys Gly Xaa Xaa Xaa Xaa Glu Xaa
             35                  40                  45

Xaa Ser Xaa Gly Xaa Xaa Xaa Xaa Xaa Gly Xaa Arg Xaa Thr Leu Xaa
 50                  55                  60

Xaa Xaa Xaa Xaa Xaa Asp Met Xaa Arg Xaa Xaa Xaa Lys Xaa Xaa Xaa
 65                  70                  75                  80

Xaa Xaa Xaa Xaa Ile Pro Glu Leu Xaa Phe Glu Xaa Xaa Xaa Xaa Xaa
             85                  90                  95

Xaa Xaa Gly Xaa Xaa Thr Thr Xaa Glu Gly Leu Xaa Xaa Xaa Xaa Ile
            100                 105                 110
```

```
Xaa Xaa Leu Xaa Xaa Xaa Xaa Pro Xaa Xaa Xaa Xaa Xaa Xaa Xaa
        115                 120                 125

Xaa Xaa Xaa Xaa Xaa Xaa Xaa Glu Phe Xaa Xaa Lys Leu Xaa Xaa
        130                 135                 140

Xaa Xaa Xaa Xaa Xaa Xaa Xaa Xaa Xaa Xaa Xaa Xaa Asp Pro Xaa
145                 150                 155                 160

Gly Asn Ser Xaa Xaa Xaa Asn Xaa Xaa Ala Pro Xaa Xaa Asp Xaa Xaa
            165                 170                 175

Xaa Xaa Xaa Xaa Xaa Tyr Xaa Arg Thr Xaa Xaa Gln Xaa Xaa Xaa Leu
            180                 185                 190

Gly Leu Xaa Xaa Xaa Xaa Xaa Glu Xaa Xaa Xaa Ala Xaa Xaa Xaa Xaa
            195                 200                 205

Xaa Arg
    210
```

(2) INFORMATION FOR SEQ ID NO:12:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (xi) SEQUENCE DESCRIPTION: SEQ ID NO:12:

```
CCGCTCCCCG TTCCTCCACA ACCACAACCT TTCTTTTTCA AGAAGATTT GCCCCGGGGA    60

AGCCGCCGCG GGAGCAACGC GTGGGG                                       86
```

(2) INFORMATION FOR SEQ ID NO:13:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (xi) SEQUENCE DESCRIPTION: SEQ ID NO:13:

```
GAACGGCACG ACGCGACTTC TGCTCACCAA GATCCCCTT                          39
```

(2) INFORMATION FOR SEQ ID NO:14:

(i) SEQUENCE CHARACTERISTICS:
        (A) LENGTH: 169 base pairs
        (B) TYPE: nucleic acid
        (C) STRANDEDNESS: single
        (D) TOPOLOGY: linear (xi) SEQUENCE DESCRIPTION: SEQ ID NO:14:

```
AGATGTCTGC CAGCGGGGCT GTGCAGCCGG ACACCCGGG GGCCGCCGTC GGGCCCTCGC    60

CCGCTGCGGC TGCGTCACCA GCCACCGGGC CTTTGTTCCG GCCCCTCAGC GCCGAAGATG   120

AGGAGCAACA GCCCACCGAG ATCGAGTCAC TGTGCATGAA CTGTTACCG              169
```

(2) INFORMATION FOR SEQ ID NO:15:

(i) SEQUENCE CHARACTERISTICS:
        (A) LENGTH: 145 base pairs
        (B) TYPE: nucleic acid
        (C) STRANDEDNESS: single
        (D) TOPOLOGY: linear (xi) SEQUENCE DESCRIPTION: SEQ ID NO:15:

```
CTTTAGAGAA ATCATCGTGA GCTCCTTTTC CTGCGAACAC TGTGGCTGGA ACAACACGGA      60

GATCCAGTCT GCAGGCAGGA TCCAGGACCA GGGAGTGCGC TACACCTTGA CCGTGAGAAG     120

CCAAGAGGAC ATGAACAGAG AAGTG                                          145
```

(2) INFORMATION FOR SEQ ID NO:16:

(i) SEQUENCE CHARACTERISTICS:
        (A) LENGTH: 51 amino acids
        (B) TYPE: amino acid
        (D) TOPOLOGY: linear (ii) MOLECULE TYPE: peptide (xi) SEQUENCE DESCRIPTION: SEQ ID NO:16:

```
Ile Pro Ala Ser Glu Ile Ser Ser Ile Leu Glu Lys Gly Glu Arg Leu
 1               5                  10                  15

Pro Gln Pro Pro Ile Cys Thr Ile Asp Val Tyr Met Ile Met Val Lys
                20                  25                  30

Cys Trp Met Ile Asp Ala Asp Ser Arg Pro Lys Phe Arg Glu Leu Ile
            35                  40                  45

Ile Glu Phe
        50
```

(2) INFORMATION FOR SEQ ID NO:17:

(i) SEQUENCE CHARACTERISTICS:
        (A) LENGTH: 51 amino acids
        (B) TYPE: amino acid
        (D) TOPOLOGY: linear (ii) MOLECULE TYPE: peptide (xi) SEQUENCE DESCRIPTION: SEQ ID NO:17:

```
Ile Pro Ala Arg Glu Ile Pro Asp Leu Leu Glu Lys Gly Glu Arg Leu
 1               5                  10                  15

Pro Gln Pro Pro Ile Cys Thr Ile Asp Val Tyr Met Ile Met Val Lys
                20                  25                  30

Cys Trp Met Ile Asp Ser Glu Cys Arg Pro Arg Phe Arg Glu Leu Val
            35                  40                  45

Ser Glu Phe
        50
```

(2) INFORMATION FOR SEQ ID NO:18:

(i) SEQUENCE CHARACTERISTICS:
        (A) LENGTH: 51 amino acids
        (B) TYPE: amino acid
        (D) TOPOLOGY: linear (ii) MOLECULE TYPE: peptide (xi) SEQUENCE DESCRIPTION: SEQ ID NO:18:

```
Leu Arg Leu Ala Glu Val Pro Asp Leu Leu Glu Lys Gly Glu Arg Leu
 1               5                  10                  15

Ala Gln Gln Pro Ile Cys Thr Ile Asp Val Tyr Met Val Met Val Lys
                20                  25                  30

Cys Trp Met Ile Asp Glu Asn Ile Arg Pro Thr Phe Lys Glu Leu Ala
            35                  40                  45

Asn Glu Phe
        50
```

(2) INFORMATION FOR SEQ ID NO:19:

(i) SEQUENCE CHARACTERISTICS:
    (A) LENGTH: 51 amino acids
    (B) TYPE: amino acid
    (D) TOPOLOGY: linear (ii) MOLECULE TYPE: peptide (xi) SEQUENCE DESCRIPTION: SEQ ID NO:19:

Leu Arg Thr Arg Glu Ile Pro Asp Leu Leu Glu Lys Gly Glu Arg Leu
 1               5                  10                  15

Pro Gln Pro Pro Ile Cys Thr Ile Asp Val Tyr Met Ile Met Val Lys
                20                  25                  30

Cys Trp Met Ile Asp Ala Asp Ser Arg Pro Lys Phe Lys Glu Leu Ala
            35                  40                  45

Ala Glu Phe
        50

(2) INFORMATION FOR SEQ ID NO:20:

(i) SEQUENCE CHARACTERISTICS:
       (A) LENGTH: 51 amino acids
       (B) TYPE: amino acid
       (D) TOPOLOGY: linear (ii) MOLECULE TYPE: peptide (xi) SEQUENCE DESCRIPTION: SEQ ID NO:20:

Met Val Asp Ser Thr Phe Tyr Asn Lys Ile Lys Ser Gly Tyr Arg Met
 1               5                  10                  15

Ala Lys Pro Asp His Ala Thr Ser Glu Val Tyr Glu Ile Met Val Lys
                20                  25                  30

Cys Trp Asn Ser Glu Pro Glu Lys Arg Pro Ser Phe Tyr His Leu Ser
            35                  40                  45

Glu Ile Val
        50

(2) INFORMATION FOR SEQ ID NO:21:

(i) SEQUENCE CHARACTERISTICS:
       (A) LENGTH: 51 amino acids
       (B) TYPE: amino acid
       (D) TOPOLOGY: linear (ii) MOLECULE TYPE: peptide (xi) SEQUENCE DESCRIPTION: SEQ ID NO:21:

Pro Met Asn Glu Gln Phe Tyr Asn Ala Ile Lys Arg Gly Tyr Arg Met
 1               5                  10                  15

Ala Gln Gln Ala His Ala Ser Asp Glu Ile Tyr Glu Ile Met Gln Lys
                20                  25                  30

Cys Trp Glu Glu Lys Phe Glu Ile Arg Pro Pro Phe Ser Gln Leu Val
            35                  40                  45

Leu Leu Leu
        50

(2) INFORMATION FOR SEQ ID NO:22:

(i) SEQUENCE CHARACTERISTICS:
       (A) LENGTH: 51 amino acids
       (B) TYPE: amino acid
       (D) TOPOLOGY: linear (ii) MOLECULE TYPE: peptide (xi) SEQUENCE DESCRIPTION: SEQ ID NO:22:

Val Pro Val Glu Glu Leu Phe Lys Leu Leu Lys Glu Gly His Arg Met
 1               5                  10                  15

Asp Lys Pro Ser Asn Cys Thr Asn Glu Leu Tyr Met Met Arg Asp
            20                  25                  30

Cys Trp His Ala Val Pro Ser Gln Arg Pro Thr Phe Lys Gln Leu Val
            35                  40                  45

Glu Asp Leu
        50

(2) INFORMATION FOR SEQ ID NO:23:

(i) SEQUENCE CHARACTERISTICS:
         (A) LENGTH: 51 amino acids
         (B) TYPE: amino acid
         (D) TOPOLOGY: linear (ii) MOLECULE TYPE: peptide (xi) SEQUENCE DESCRIPTION: SEQ ID NO:23:

Leu Ser Asn Thr Glu Ala Ile Asp Cys Ile Thr Gln Gly Arg Glu Leu
 1               5                  10                  15

Glu Arg Pro Arg Ala Cys Pro Pro Glu Val Tyr Ala Ile Met Arg Gly
            20                  25                  30

Cys Trp Gln Arg Glu Pro Gln Gln Arg His Ser Ile Lys Asp Val His
            35                  40                  45

Ala Arg Leu
        50

(2) INFORMATION FOR SEQ ID NO:24:

(i) SEQUENCE CHARACTERISTICS:
         (A) LENGTH: 51 amino acids
         (B) TYPE: amino acid
         (D) TOPOLOGY: linear (ii) MOLECULE TYPE: peptide (xi) SEQUENCE DESCRIPTION: SEQ ID NO:24:

Leu Ser Asn Glu Gln Val Leu Lys Phe Val Met Asp Gly Gly Tyr Leu
 1               5                  10                  15

Asp Gln Pro Asp Asn Cys Pro Glu Arg Val Thr Asp Leu Met Arg Met
            20                  25                  30

Cys Trp Gln Phe Asn Pro Asn Met Arg Pro Thr Phe Leu Glu Ile Val
            35                  40                  45

Asn Leu Leu
        50

(2) INFORMATION FOR SEQ ID NO:25:

(i) SEQUENCE CHARACTERISTICS:
         (A) LENGTH: 51 amino acids
         (B) TYPE: amino acid
         (D) TOPOLOGY: linear (ii) MOLECULE TYPE: peptide (xi) SEQUENCE DESCRIPTION: SEQ ID NO:25:

Leu Ser Asn Glu Gln Val Leu Arg Phe Val Met Glu Gly Gly Leu Leu
 1               5                  10                  15

Asp Lys Gln Asp Asn Cys Pro Asp Met Leu Phe Glu Leu Met Arg Met
            20                  25                  30

```
    Cys Trp Gln Tyr Asn Pro Lys Met Arg Pro Ser Phe Leu Glu Ile Ile
            35                  40                  45

Ser Ser Ile
         50

(2) INFORMATION FOR SEQ ID NO:26:

(i) SEQUENCE CHARACTERISTICS:
           (A) LENGTH: 15 amino acids
           (B) TYPE: amino acid
           (D) TOPOLOGY: linear (ii) MOLECULE TYPE: peptide (xi) SEQUENCE DESCRIPTION: SEQ ID NO:26:

Asn Asp Met Lys Thr Glu Gly Tyr Glu Ala Gly Leu Ala Pro Gln
 1               5                  10                  15

(2) INFORMATION FOR SEQ ID NO:27:

(i) SEQUENCE CHARACTERISTICS:
           (A) LENGTH: 8 amino acids
           (B) TYPE: amino acid
           (D) TOPOLOGY: linear (ii) MOLECULE TYPE: peptide (xi) SEQUENCE DESCRIPTION: SEQ ID NO:27:

Asp Tyr Lys Asp Asp Asp Asp Lys
 1               5

(2) INFORMATION FOR SEQ ID NO:28:

(i) SEQUENCE CHARACTERISTICS:
           (A) LENGTH: 33 amino acids
           (B) TYPE: amino acid
           (D) TOPOLOGY: linear (ii) MOLECULE TYPE: peptide (xi) SEQUENCE DESCRIPTION: SEQ ID NO:28:

Cys Xaa Xaa Cys Xaa Xaa Xaa Xaa Xaa Xaa Xaa Xaa Xaa Xaa Xaa
 1               5                  10                  15

Xaa Xaa Xaa Xaa Xaa Xaa Xaa Xaa Xaa Xaa Xaa Xaa Xaa Cys Xaa Xaa
            20                  25                  30

Cys (2) INFORMATION FOR SEQ ID NO:29:

(i) SEQUENCE CHARACTERISTICS:
           (A) LENGTH: 255 base pairs
           (B) TYPE: nucleic acid
           (C) STRANDEDNESS: single
           (D) TOPOLOGY: linear (xi) SEQUENCE DESCRIPTION: SEQ ID NO:29:

CCGCTCCCCG TTCCTCCACA ACCACAACCT TTCTTTTTCA AAGAAGATTT GCCCCGGGGA      60

AGCCGCCGCG GGAGCAACGC GTGGGGAGAT GTCTGCCAGC GGGGCTGTGC AGCCGGGACA     120

CCCGGGGGCC GCCGTCGGGC CCTCGCCCGC TGCGGCTGCG TCACCAGCCA CCGGGCCTTT     180

GTTCCGGCCC CTCAGCGCCG AAGATGAGGA GCAACAGCCC ACCGAGATCG AGTCACTGTG     240

CATGAACTGT TACCG                                                     255

(2) INFORMATION FOR SEQ ID NO:30:
```

(i) SEQUENCE CHARACTERISTICS:
    (A) LENGTH: 184 base pairs
    (B) TYPE: nucleic acid
    (C) STRANDEDNESS: single
    (D) TOPOLOGY: linear (xi) SEQUENCE DESCRIPTION: SEQ ID NO:30:

GAACGGCACG ACGCGACTTC TGCTCACCAA GATCCCCTTC TTTAGAGAAA TCATCGTGAG    60

CTCCTTTTCC TGCGAACACT GTGGCTGGAA CAACACGGAG ATCCAGTCTG CAGGCAGGAT   120

CCAGGACCAG GGAGTGCGCT ACACCTTGAC CGTGAGAAGC CAAGAGGACA TGAACAGAGA   180

AGTG                                                                184

(2) INFORMATION FOR SEQ ID NO:31:

(i) SEQUENCE CHARACTERISTICS:
        (A) LENGTH: 294 base pairs
        (B) TYPE: nucleic acid
        (C) STRANDEDNESS: single
        (D) TOPOLOGY: linear (xi) SEQUENCE DESCRIPTION: SEQ ID NO:31:

CCGCTCCCCG TTCCTCCACA ACCACAACCT TTCTTTTTCA AAGAAGATTT GCCCCGGGGA    60

AGCCGCCGCG GGAGCAACGC GTGGGGAGAT GTCTGCCAGC GGGGCTGTGC AGCGGGACA   120

CCCGGGGGCC GCCGTCGGGC CCTCGCCCGC TGCGGCTGCG TCACCAGCCA CCGGGCCTTT   180

GTTCCGGCCC CTCAGCGCCG AAGATGAGGA GCAACAGCCC ACCGAGATCG AGTCACTGTG   240

CATGAACTGT TACCGGAACG GCACGACGCG ACTTCTGCTC ACCAAGATCC CCTT         294

(2) INFORMATION FOR SEQ ID NO:32:

(i) SEQUENCE CHARACTERISTICS:
        (A) LENGTH: 439 base pairs
        (B) TYPE: nucleic acid
        (C) STRANDEDNESS: single
        (D) TOPOLOGY: linear (xi) SEQUENCE DESCRIPTION: SEQ ID NO:32:

CCGCTCCCCG TTCCTCCACA ACCACAACCT TTCTTTTTCA AAGAAGATTT GCCCCGGGGA    60

AGCCGCCGCG GGAGCAACGC GTGGGGAGAT GTCTGCCAGC GGGGCTGTGC AGCGGGACA   120

CCCGGGGGCC GCCGTCGGGC CCTCGCCCGC TGCGGCTGCG TCACCAGCCA CCGGGCCTTT   180

GTTCCGGCCC CTCAGCGCCG AAGATGAGGA GCAACAGCCC ACCGAGATCG AGTCACTGTG   240

CATGAACTGT TACCGGAACG GCACGACGCG ACTTCTGCTC ACCAAGATCC CCTTCTTTAG   300

AGAAATCATC GTGAGCTCCT TTTCCTGCGA ACACTGTGGC TGGAACAACA CGGAGATCCA   360

GTCTGCAGGC AGGATCCAGG ACCAGGGAGT GCGCTACACC TTGACCGTGA AAGCCAAGA   420

GGACATGAAC AGAGAAGTG                                                439

(2) INFORMATION FOR SEQ ID NO:33:

(i) SEQUENCE CHARACTERISTICS:
        (A) LENGTH: 490 amino acids
        (B) TYPE: amino acid
        (D) TOPOLOGY: linear (ii) MOLECULE TYPE: protein (xi) SEQUENCE DESCRIPTION: SEQ ID NO:33:

Xaa Xaa Xaa Xaa Xaa Xaa Xaa Xaa Xaa Xaa Xaa Xaa Xaa Gly Xaa Xaa
 1               5                  10                  15

```
Xaa Xaa Xaa Val Xaa Xaa Xaa Xaa Xaa Xaa Xaa Xaa Xaa Xaa
         20              25              30

Xaa Xaa Xaa Xaa Xaa Xaa Xaa Xaa Xaa Xaa Xaa Xaa Xaa Xaa
     35              40              45

Xaa Glu Xaa Glu Ser Leu Cys Met Xaa Cys Xaa Xaa Asn Gly Xaa Thr
 50              55              60

Xaa Leu Leu Leu Thr Xaa Ile Pro Xaa Phe Arg Glu Xaa Xaa Xaa Xaa
 65              70              75              80

Ser Phe Xaa Cys Xaa His Cys Gly Xaa Xaa Asn Xaa Xaa Xaa Gln Xaa
             85              90              95

Ala Xaa Xaa Ile Gln Xaa Gly Xaa Xaa Xaa Xaa Xaa Val Xaa
             100             105             110

Xaa Xaa Glu Asp Xaa Asn Arg Xaa Val Xaa Lys Xaa Xaa Xaa Ala Xaa
         115             120             125

Xaa Xaa Xaa Xaa Glu Xaa Xaa Xaa Glu Ile Pro Xaa Xaa Xaa Xaa Xaa
 130             135             140

Gly Xaa Leu Thr Thr Val Glu Gly Leu Xaa Xaa Xaa Xaa Xaa Xaa
145             150             155             160

Leu Xaa Xaa Xaa Gln Xaa Xaa Arg Xaa Xaa Xaa Xaa Xaa Xaa Xaa
         165             170             175

Xaa Xaa Ile Xaa Xaa Phe Ile Xaa Lys Xaa Xaa Xaa Xaa Xaa Xaa Xaa
         180             185             190

Xaa Xaa Xaa Xaa Xaa Pro Xaa Thr Xaa Xaa Xaa Asp Asp Xaa Xaa Gly
         195             200             205

Asn Ser Xaa Xaa Glu Xaa Xaa Xaa Xaa Xaa Xaa Xaa Xaa Xaa
         210             215             220

Xaa Xaa Xaa Xaa Tyr Xaa Arg Thr Xaa Xaa Gln Xaa Xaa Xaa Xaa Gly
225             230             235             240

Xaa Xaa Xaa Xaa Xaa Xaa Xaa Glu Xaa Xaa Xaa Xaa Xaa Xaa Xaa
             245             250             255

Xaa Xaa Xaa Xaa Xaa Xaa Xaa Xaa Xaa Xaa Xaa Xaa Xaa Xaa
         260             265             270

Xaa Xaa Xaa Xaa Xaa Xaa Xaa Xaa Xaa Xaa Xaa Glu Xaa Xaa
         275             280             285

Xaa Asn Glu Val Xaa Xaa Phe Xaa Xaa Xaa Cys Pro Xaa Cys Xaa Xaa
 290             295             300

Xaa Xaa Xaa Thr Xaa Met Lys Xaa Xaa Xaa Ile Pro His Phe Lys Glu
305             310             315             320

Val Ile Ile Met Xaa Thr Xaa Cys Xaa Xaa Cys Gly Xaa Xaa Xaa Asn
             325             330             335

Glu Val Lys Xaa Gly Gly Xaa Xaa Xaa Xaa Gly Xaa Xaa Ile Thr
         340             345             350

Leu Xaa Xaa Xaa Asp Xaa Xaa Asp Xaa Xaa Arg Asp Xaa Leu Lys Ser
     355             360             365

Glu Thr Xaa Ser Xaa Xaa Ile Pro Glu Leu Xaa Xaa Xaa Xaa Xaa
370             375             380

Xaa Xaa Leu Gly Gly Xaa Phe Thr Thr Xaa Glu Gly Leu Leu Xaa Xaa
385             390             395             400

Xaa Xaa Xaa Xaa Xaa Xaa Xaa Xaa Phe Xaa Xaa Xaa Xaa Asp Ser
             405             410             415

Xaa Xaa Xaa Xaa Xaa Xaa Xaa Xaa Xaa Phe Xaa Xaa Xaa
         420             425             430

Xaa Xaa Xaa Xaa Xaa Gly Xaa Xaa Xaa Xaa Xaa Ile Xaa Xaa Asp
         435             440             445
```

```
        Pro Xaa Xaa Xaa Ser Tyr Xaa Gln Asn Xaa Tyr Ala Pro Xaa Xaa Asp
            450                 455                 460

Pro Xaa Met Xaa Xaa Glu Xaa Tyr Xaa Arg Xaa Xaa Xaa Xaa Asn Glu
        465                 470                 475                 480

Glu Leu Gly Leu Xaa Asp Xaa Lys Xaa Glu
                        485                 490

(2) INFORMATION FOR SEQ ID NO:34:

(i) SEQUENCE CHARACTERISTICS:
        (A) LENGTH: 1094 base pairs
        (B) TYPE: nucleic acid
        (C) STRANDEDNESS: single
        (D) TOPOLOGY: linear (xi) SEQUENCE DESCRIPTION: SEQ ID NO:34:

CTGCAGCTTT GAACTCAGCC AGCTTCCCTG ACTCAAACGA TCAATCCGCT TCAGCCTCCC      60

GAGTAGCTGG GACTACAGAC GGTGCCATCA CGCCCAGCTC ATTGTTGATT CCCGCCCCCT     120

TGGTAGAGAC GGGATTCCGC TATATTGCCT GGGCTGGTGT CGAACTCATA GAACAAAGGA     180

TCCTCCCTCC TGGGCCTGGG CGTGGGCTCG CAAAACGCTG GGATTCCCGG ATTACAGGCG     240

GGCGCACCAC ACCAGGAGCA AACACTTCCG GTTTTAAAAA TTCAGTTTGT GATTGGCTGT     300

CATTCAGTAT TATGCTAATT AAGCATGCCC GGTTTTAAAC CTCTTAAAAC AACTTTTAAA     360

ATTACCTTTC CACCTAAAAC GTTAAAATTT GTCAAGTGAT AATATTCGAC AAGCTGTTAT     420

TGCCAAACTA TTTTCCTATT TGTTTCCTAA TGGCATCGGA ACTAGCGAAA GTTTCTCGCC     480

ATCAGTTAAA AGTTTGCGGC AGATGTAGAC CTAGCAGAGG TGTGCGAGGA GGCCGTTAAG     540

ACTATACTTT CAGGGATCAT TTCTATAGTG TGTTACTAGA GAAGTTTCTC TGAACGTGTA     600

GAGCACCGAA AACCACGAGG AAGAGAGGTA GCGTTTTCTC CTGAGCGTGA AGCCGGCTTT     660

CTGGCGTTGC TTGGCTGCAA CTGCCGTCAG CCATTGATGA TCGTTCTTCT CTCCGTATTG     720

GGGAGTGAGA GGGAGAGAAC GCGGTCTGAG TGGTTTTTCC TTCTTGATGG CTCAATGACA     780

GAGACTAGCT CGTAAACTCC GGGCCGTTTC CGGGCTGTTC GCTCCTGCTT GGCAATGTCG     840

CGAGAAAGGT TTTCGCCTCC TGTTTCAGCG GTGACGGCTC TTGGGTTTTC TCGGGGTGGC     900

TTTTTAATTT TAGTCTTGGC GCGAGGCGGG GGATGCTGTG TGGCACCTCC TATTGTCTCT     960

TTTTGCGTTT TCTCCCATTC TCGCTCCCTC TTTTGTCGCC GTTTCCCGCC CGCCACTCCC    1020

ACCCCCAGAC GGGGTCTCCG GGTCTCTTGT TCTGTCTGCC GGCCCCGGCT GGAGTGCAGT    1080

GGCGCGATCT CGGG                                                     1094

(2) INFORMATION FOR SEQ ID NO:35:

(i) SEQUENCE CHARACTERISTICS:
        (A) LENGTH: 51 amino acids
        (B) TYPE: amino acid
        (D) TOPOLOGY: linear (ii) MOLECULE TYPE: peptide (xi) SEQUENCE DESCRIPTION: SEQ ID NO:35:

Xaa Xaa Xaa Xaa Xaa Xaa Xaa Xaa Xaa Xaa Xaa Xaa Gly Xaa Xaa Xaa
 1               5                  10                  15

Xaa Xaa Xaa Xaa Xaa Xaa Xaa Xaa Xaa Xaa Xaa Xaa Xaa Met Xaa Xaa
                20                  25                  30
```

-continued

```
Cys Trp Xaa Xaa Xaa Xaa Xaa Xaa Arg Xaa Xaa Xaa Xaa Xaa Xaa Xaa
         35                  40                  45

Xaa Xaa Xaa
     50
```

NON-ACTIVATED RECEPTOR COMPLEX PROTEINS AND USES THEREOF

CROSS REFERENCE TO RELATED APPLICATIONS

This application claims priority from U.S. Provisional Application Ser. No. 60/019,219, filed Jun. 6, 1996.

STATEMENT AS TO FEDERALLY SPONSORED RESEARCH

This invention was made in part with Government funding, and the Government therefore may have certain rights in the invention.

BACKGROUND OF THE INVENTION

This application relates to signal transduction proteins.

The epidermal growth factor receptor (EGF-R) is a transmembrane glycoprotein with an extracellular ligand binding domain and a cytoplasmic tyrosine kinase domain [Ullrich et al., Cell 61, 203 (1990); Schlessinger et al., Neuron 9, 383 (1992)]. Treatment of cells with epidermal growth factor (EGF) causes increased EGF receptor tyrosine kinase activity, i.e., the activated state. Substrates for the activated EGF-R tyrosine kinase include the COOH terminal region of the receptor [Ullrich et al., supra; Schlessinger et al., supra]. The tyrosine phosphorylated EGF receptor binds to modular signaling proteins that contain Src homolog (SH2) or PTB domains [Ullrich et al., supra; Schlessinger et al., supra; Koch et al, Science 252, 668 (1991); Pawson et al., Cell 71, 359 (1992); Kavanaugh et al., Science 266, 1862 (1994); Bork et al., Cell 80, 693 (1995); Kavanaugh et al., Science 268, 1177 (1995)]. However, prior to the formation of the receptor SH2/PTB signaling complex, the non-activated EGF receptor is proposed to interact with other proteins [Ullrich et al., supra; Schlessinger et al., supra]. The identity of proteins within the non-activated EGF-R complex is currently unknown.

SUMMARY OF THE INVENTION

The invention is based on the discovery of a novel class of signaling molecules that bind to non-activated membrane receptors (i.e., a membrane receptor which has not been induced or activated by an extracellular factor such as a hormone, adhesion molecule, or neurotransmitter) and are subsequently released from the membrane receptor after activation (e.g., following treatment of cells with an appropriate ligand such as EGF). Following their release, these polypeptides are disseminated to subcellular locations (e.g., the nucleus and nucleolus) where they are further capable of relaying signals (e.g., via protein-protein or protein-RNA interactions) throughout the cell. These signaling molecules are termed "ZPR1 proteins" or "ZPR1 polypeptides."

In general, the invention features a substantially pure ZPR1 polypeptide (the terms "ZPR1," "Zpr1," and "Zpr" are used interchangeably herein). In preferred embodiments, the ZPR1 polypeptide specifically binds to a non-activated membrane-bound receptor (e.g., EGF or PDGF-β receptors). Such ZPR1 polypeptides can be isolated from any eukaryote, including mammals (e.g., rodents such as mice (SEQ ID NO:1) and humans (SEQ ID NO:2)) and fungi (e.g., S. cerevisiae (SEQ ID NO:3) and S. pombe (SEQ ID NO:4)).

In another aspect, the invention features isolated nucleic acid that includes a sequence encoding a ZPR1 polypeptide. Preferably, such a nucleic acid (e.g., DNA) is from a eukaryote such as a rodent or human, or a fungus such as S. cerevisiae and S. pombe.

In another aspect, the invention features a method of producing a recombinant ZPR1 polypeptide. The method includes: (a) providing a cell transformed with a nucleic acid encoding a ZPR1 polypeptide positioned for expression in the cell; (b) culturing the transformed cell under conditions for expressing the nucleic acid; and (c) recovering the recombinant ZPR1 polypeptide.

In related aspects, the invention features vectors and cells that include isolated ZPR1 nucleic acid; and ZPR1 polypeptides that are produced by expression of isolated ZPR1 DNA. In another related aspect, the invention includes a substantially pure antibody that specifically binds a ZPR1 polypeptide.

In another aspect, the invention features a method for suppressing a ZPR1-EGF receptor mediated interaction in a mammal. The method includes administering to the mammal a compound that inhibits a ZPR1-EGF receptor interaction.

In still another aspect, the invention features a method of identifying a compound that decreases a binding interaction between a ZPR1 polypeptide and a receptor. The method includes: (a) mixing a compound with a ZPR1 polypeptide and a receptor; (b) measuring binding of the ZPR1 polypeptide to the receptor in the presence of the compound; and (c) identifying whether the compound decreases binding of the ZPR1 polypeptide to the receptor relative to a control sample, decreased binding indicating that the compound decreases binding between the ZPR1 and the receptor. In addition, the invention also features a method of identifying a compound that increases a binding interaction between a ZPR1 polypeptide and a receptor. This method involves: (a) mixing a compound with a ZPR1 polypeptide and a receptor; (b) measuring binding of the ZPR1 polypeptide to the receptor in the presence of the compound; and (c) identifying whether the compound increases binding of the ZPR1 polypeptide to the receptor relative to a control sample, increased binding indicating that the compound increases binding between the ZPR1 polypeptide and the receptor.

In still another aspect, the invention features a method of diagnosing a mammal for the presence of a malignancy or an increased likelihood of developing a malignancy. The method involves measuring ZPR1 gene expression in a sample from the mammal, a decrease in ZPR1 expression relative to a wild-type sample being an indication that the mammal has a malignancy or has an increased likelihood of developing a malignancy. A related feature of the invention involves the identification of ZPR1 mutations.

In related aspects, the invention features kits for diagnosing the presence of a malignancy or an increased likelihood of developing a malignancy in a mammal. In another aspect, the invention features a method of diagnosing a mammal for the presence of a malignancy or an increased likelihood of developing a malignancy. The method includes isolating a sample of nucleic acid from the mammal and determining whether the nucleic acid includes a mutated ZPR1 gene, a ZPR1 mutation being an indication that the mammal has a malignancy or has an increased likelihood of developing a malignancy.

In still another aspect, the invention features a method of treating a mammal with a ZPR1-associated disorder, for example, malignancy. The method includes administering to the mammal a transgene encoding a ZPR1 polypeptide or administering to the mammal a ZPR1 polypeptide in an amount sufficient to inhibit an increase in the malignancy.

In another aspect, the invention features a method of identifying a modulatory compound which is capable of increasing or decreasing the expression of a ZPR1 gene.

In related aspects, the invention features methods of treating a mammal with a disease involving increased expression of a ZPR1-encoding gene or decreased expression of a ZPR1-encoding gene, or the administration of ZPR1 agonists, ZPR1 antagonists, or modulators.

The invention features a method for suppressing a ZPR1-nucleolar interactions in a eukaryote, the method involving administration to the eukaryote a compound that inhibits a ZPR1-nucleolar interaction. The eukaryote treated by this method may be a mammal (e.g., human). Compounds used in this method can be nucleic acids, ZPR1 polypeptides or fragments of ZPR1 polypeptides. The method includes suppressing ZPR1-nucleolar interactions that involve RNA, including small nucleolar RNA (e.g., U3) and fragments of those RNAs.

Another aspect of the invention features a method of treating an animal with a ZPR1-associated disorder, the method involving the administering to the animal a compound that inhibits a ZPR1-nucleolar interaction. The compound can be a small nucleolar RNA, a fragment of such an RNA, a ZPR1 polypeptide or a fragment of a ZPR1 polypeptide.

A "ZPR1 polypeptide" is an amino acid sequence that includes a zinc finger domain (e.g., the ZF1 and ZF2 domains described herein) that specifically binds to a cytoplasmic domain (e.g., a cytoplasmic tyrosine kinase) of a membrane growth factor (e.g., epidermal growth factor (EGF) receptor, platelet-derived growth factor (PDGF) receptor, and any EPH class of neuronal receptor such as (Eph, Eck, Hek, Erk, Htk). ZPR1 polypeptides also include ZPR1 fusion proteins (e.g., ZPR1-GST) and epitope-tagged ZPR1 polypeptides. ZPR1 polypeptides, in general, have amino acid identity that is at least 30%, preferably 50%, and most preferably 80%, 90%, or even 95% identical to any of the ZPR1 amino acid sequences including, but not limited to, mammalian sequences from the mouse (FIG. 1; SEQ ID NO:1), rat, or human (FIG. 2; SEQ ID NO:2), and yeast ZPR1 sequences from S. cerevisiae (FIG. 3; SEQ ID NO:3) and S. pombe (FIG. 4; SEQ ID NO:4), which are disclosed herein.

A "substantially identical" polypeptide sequence is an amino acid sequence that differs from a given amino acid sequence only by conservative amino acid substitutions, for example, substitution of one amino acid for another of the same class or by one or more non-conservative substitutions, deletions, or insertions located at positions of the amino acid sequence which do not destroy the function of the polypeptide (assayed, e.g., as described herein).

Homology or identity is typically measured using sequence analysis software (e.g., Sequence Analysis Software Package of the Genetics Computer Group, University of Wisconsin Biotechnology Center, 1710 University Avenue, Madison, Wis. 53705). Such software matches similar sequences by assigning degrees of homology to various substitutions, deletions, substitutions, and other modifications. Conservative substitutions typically include, but are not limited to, substitutions within the following groups: glycine, alanine; valine, isoleucine, leucine; aspartic acid, glutamic acid, asparagine, glutamine; serine, threonine; lysine, arginine; and phenylalanine, tyrosine.

If nucleic acid sequences are compared, a "substantially identical" nucleic acid sequence is one which is at least 50%, more preferably 80%, and most preferably 90% or more identical to a given nucleic acid sequence, e.g., the nucleotide sequence of FIG. 1 (SEQ ID NO:5), FIG. 5 (SEQ ID NO:6), FIG. 6 (SEQ ID NO:7), or FIG. 7 (SEQ ID NO:8). The length of nucleic acid sequence comparison is generally at least 20 nucleotides, preferably at least 100 nucleotides, more preferably at least 200 nucleotides, and most preferably 1,000 nucleotides. Again, homology is typically measured using sequence analysis software, e.g., BESTFIT and PILEUP programs from the Wisconsin Genetics Computer Group and the MacVector program from IBI-Kodak.

A "protein" or "polypeptide" is any chain of amino acids, regardless of length or post-translational modification (e.g., glycosylation or phosphorylation).

A "substantially pure" preparation is one that is at least 60% by weight (dry weight) of the compound of interest, e.g., the ZPR1 polypeptide or a ZPR1-specific antibody. Preferably the preparation is at least 75%, more preferably at least 90%, and most preferably at least 99%, by weight the compound of interest. Purity can be measured by any appropriate method, e.g., column chromatography, polyacrylamide gel electrophoresis, or HPLC analysis.

An "isolated nucleic acid" is a nucleic acid that is free of the genes which, in the naturally-occurring genome of the organism from which the nucleic acid of the invention is derived, flank the nucleic acid. The term therefore includes, for example, a recombinant DNA that is incorporated into a vector, into an autonomously replicating plasmid or virus, or into the genomic DNA of a prokaryote or eukaryote, or which exists as a separate molecule (e.g., a cDNA or a genomic DNA fragment produced by polymerase chain reaction (PCR) or restriction endonuclease treatment) independent of other sequences. It also includes a recombinant DNA which is part of a hybrid gene encoding additional polypeptide sequence.

A "transformed cell" is a cell into which (or into an ancestor of which) has been introduced, by means of recombinant DNA techniques, a nucleic acid molecule encoding (as used herein) ZPR1 protein.

By "positioned for expression" is meant that the DNA molecule is positioned adjacent to a DNA sequence that directs transcription and translation of the sequence (i.e., facilitates the production of ZPR1 protein).

A "purified antibody" is an antibody that is at least 60%, by weight, free from the proteins and naturally-occurring organic molecules with which it is naturally associated. Preferably, the preparation is at least 75%, more preferably at least 90%, and most preferably at least 99%, by weight, antibody.

An antibody that "specifically binds" a ZPR1 polypeptide is an antibody that recognizes and binds a ZPR1 polypeptide (including ZPR1 fusion proteins (e.g., ZPR1-GST) and epitope-tagged ZPR1), but that does not substantially recognize and bind other molecules in a sample (e.g., a biological sample) which naturally includes a ZPR1 polypeptide. An antibody that "specifically binds" ZPR1 is sufficient to detect a ZPR1 protein product in such a biological sample using one or more of the standard immunological techniques available to those in the art (for example, immunoblotting (i.e., Western blotting) or immunoprecipitation).

A "malignancy" is any neoplasm or abnormal tissue that grows by cellular proliferation more rapidly than normal or that continues to grow after growth stimuli cease. Most malignancies show partial or complete lack of structural organization or functional coordination with surrounding normal tissue. A malignancy according to the invention is generally either locally invasive or metastatic and generally involves the over-expression of growth factor activity, e.g., EGF.

By "relative to a wild-type sample" is meant either (a) relative to an equivalent tissue sample from an unaffected individual or (b) relative to an unaffected sample of similar tissue type from the mammal being diagnosed.

A "carcinoma" is any of the various types of malignancies derived from epithelial tissues. Carcinomas include, without limitation, malignancies arising in breast, cervix, prostate, skin, large intestine, lung/bronchi, liver, brain, kidney, ovary, uterus, stomach, esophagus, nasopharynx, larynx, or glandular tissue.

A "cell of epithelial origin" is a cell (for example, a malignant cell) that, at some point in its life cycle, was an epithelial cell (i.e., a cell of the avascular layer that covers the free surface of the body, including, without limitation, the cutaneous, mucous, and serous layers, all glandular surfaces, and structures derived therefrom).

"Immunological methods" are any assay involving antibody-based detection techniques including, without limitation, immunoblotting (e.g., Western blotting), immunoprecipitation, and direct and competitive enzyme linked immunosorbent assay (ELISA) and radioimmunassay (RIA) techniques.

A "means for detecting" is any one or a series of components that sufficiently indicate a detection event of interest. Such means involve at least one label that can be assayed or observed, including, without limitation, radioactive, fluorescent, and chemiluminescent labels.

"ZPR1 RNA" is RNA (e.g., messenger RNA) transcribed from a ZPR1 DNA sequence. "ZPR1 DNA" is DNA that is responsible for the transcription and translation of a ZPR1 polypeptide.

A "transgene" is a DNA sequence that is inserted by artifice into a cell and becomes a part of the genome of that cell and its progeny. Such a transgene can be partly or entirely heterologous to the cell.

A "modulatory compound" is any compound capable of either increasing or decreasing ZPR1 gene expression (i.e., at the level of transcription, translation, or post-translation), or increasing or decreasing ZPR1 protein activity (i.e., the amount of activity, for example, EGF receptor (or PDGF receptor or EPH receptor) binding activity, per unit of ZPR1 protein).

"Small nucleolar RNA" or "snoRNA" refers to RNA sequences located in the nucleolus and includes the sequences encoded by the U3, U10, U15, U22, and U33 genes.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

The drawings will first be described.

BRIEF DESCRIPTION OF DRAWINGS

FIGS. 1A–C together are a schematic representation of the nucleotide sequence (SEQ ID NO:5) and corresponding deduced amino acid sequence (SEQ ID NO:1) of the murine ZPR1 polypeptide. The amino acid sequence is presented as single letter code. The ZPR1 nucleotide sequence (2,162 bp) has been deposited in GenBank with the accession number U41287.

FIG. 2 is a schematic representation of an alignment of the human (SEQ ID NO:2), mouse (SEQ ID NO:1), *S. cerevisiae* (SEQ ID NO:3), and *S. pombe* (SEQ ID NO:4) deduced ZPR1 amino acid sequences presented as single letter code. The bottom line indicates the sites of consensus between all four ZPR1 sequences (SEQ ID NO:33). Gaps introduced to optimize the alignment are indicated with a dash (-) Identical residues are illustrated with a period (.). The two zinc finger motifs are overlined and the Cys residues are indicted with asterisks (*)

FIGS. 3A–B together are a schematic representation of the deduced amino acid sequence (SEQ ID NO:3) of the *S. cerevisae* ZPR1 polypeptide.

FIGS. 4A–B together are a schematic representation of the deduced amino acid sequence (SEQ ID NO:4) of the *S. pombe* ZPR1 polypeptide.

FIGS. 5A–B together are a schematic representation of the genomic nucleotide sequence (SEQ ID NO:6) that encodes the *S. cerevisae* ZPR1 polypeptide.

FIGS. 6A–C together are a schematic representation of nucleotide sequence (SEQ ID NO:7) that encodes the *S. pombe* ZPR1 polypeptide.

FIG. 7 is an illustration showing the cDNA sequence of human ZPR1.

FIG. 8 is an illustration showing the alignment of the murine ZPR1 $NH_2$-terminus (SEQ ID NO:9) to the COOH-terminus of ZPR1 (SEQ ID NO:10). Gaps introduced to optimize the alignment are indicated with a dash (-). Identical residues are illustrated with a period (.). The zinc finger consensus motif is also shown (SEQ ID NO:11).

FIG. 9 is a schematic illustration showing the predicted domain structure of murine ZPR1, including two zinc fingers (ZF1 and ZF2; SEQ ID NO:12 and SEQ ID NO:13, respectively) and two regions adjacent to the fingers (A and B; SEQ ID NO:14 and SEQ ID NO:15, respectively).

FIG. 10 is a bar graph illustrating the deletion analysis of EGF receptor binding to ZPR1. The wild-type (WT) EGF receptor and COOH terminal truncation mutants (Δ958 and Δ908) were translated in vitro with [$^{35}$S]methionine. The translated EGF receptors were subsequently incubated with immobilized GST-ZPR1 (designated as ■). Control experiments were performed using immobilized GST (designated as ☐). Bound EGF receptors were detected by sodium dodecyl sulfate-polyacrylamide gel electrophoresis (SDS-PAGE) and Phosphorimager analysis. The relative binding of the EGF receptors is presented.

FIG. 11 is an illustration showing the aligned primary sequences of sub-domains X and XI of the EGF receptor HER1 (SEQ ID NO:16), HER2 (SEQ ID NO:17), HER3 (SEQ ID NO:18), HER4 (SEQ ID NO:19), PDGF-Rα (SEQ ID NO:20), PDGF-Rβ (SEQ ID NO:21), FGF-R1 (SEQ ID NO:22); TrkA (SEQ ID NO:23), insulin (INS-R) (SEQ ID NO:24), and insulin-like growth factor 1 (IGF1-R) (SEQ ID NO:25) receptors. The sequence of EGF receptor residues 894–944 is presented. The conserved helices G, H, and I are indicated. Identical residues are illustrated with a period (.). Gaps which were introduced to optimize the alignment are indicated with a dash (-).

ZPR1 Polypeptides

Figure 12:
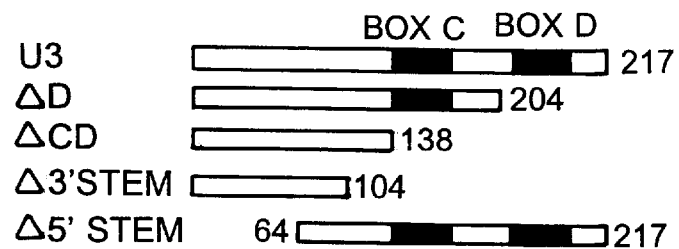
FIG. 12 is a diagram of the constructs used for deletion analysis of U3 sequences required for interaction with ZPR1.
Figure 14:
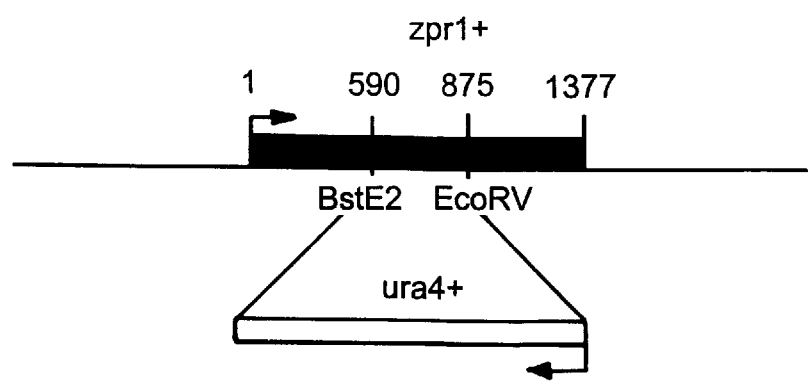
FIG. 14 is a schematic representation of the S. pombe zpr1+ genomic locus and the disrupted gene (zpr1::ura4+).

ZPR polypeptides according to the invention include any full-length ZPR polypeptide (as described in FIG. 1 (SEQ ID NO:1), FIG. 3 (SEQ ID NO:3), FIG. 4 (SEQ ID NO:4, FIG. 2 (SEQ ID NO:2), or a fragment or an analog of such ZPR1 polypeptides. ZPR1 polypeptides can be derived from any source, including, but not limited to, mammals such as humans, mice, or rats, and yeast such as S. cerevisiae and S. pombe. Polypeptides according to the invention are used, e.g, to screen for antagonists or agonists of a ZPR1:protein interaction (e.g., a ZPR1:EGF receptor or ZPR1:protein kinase), a ZPR1:mediated physiological response, or ZPR1 expression or activity (see below) according to conventional techniques. ZPR1 fragments or analogs are also useful, for example, as antagonists of a ZPR1:polypeptide interaction (e.g., a ZPR1:EGF receptor interaction) activity. The efficacy of a ZPR1 fragment or analog, e.g., as either an antagonist or agonist, is dependent upon its ability to interact with, for example, a polypeptide such as the EGF receptor or the ZPR1 polypeptide itself. Such an interaction can be readily assayed using any number of standard binding methods and functional assays (e.g., those described below).

Specific ZPR1 polypeptide fragments of interest include any portion of a ZPR1 polypeptide which is capable of interaction with a polypeptide (e.g., a non-activated membrane-bound receptor such as the EGF receptor). Fragments, for example, all or part of the ZPR1 N-terminus, the ZF1+A or ZF1+B domains, or a zinc finger domain, e.g., ZF1 or ZF2, are useful as antagonists or agonists (as described above), and are also useful as immunogens for producing antibodies which neutralize the activity of ZPR1; see infra).

In addition, from the primary amino acid sequence the secondary protein structure and, therefore, the domains of ZPR1 can be deduced semi-empirically using any standard hydrophobicity/hydrophilicity calculation, e.g., the Chou-Fasman method (see, e.g., Chou and Fasman, Ann. Rev. Biochem. 47:251, 1978). Hydrophilic domains present themselves as strong candidates for antigenicity and hydrophobic regions for binding domains, and therefore, useful antagonists or agonists.

Candidate fragments are tested for interaction with a non-activated membrane-bound receptor (e.g., the EGF receptor) and their ability to modulate a ZPR1-mediated physiological response, i.e., to serve as ZPR1 agonists, by any of the assays described herein. Fragments are also tested for their ability to antagonize the interaction between a ZPR1 polypeptide and a receptor using the assays described herein. Analogs of useful ZPR1 fragments (as described above) can also be produced and tested for efficacy as screening components, antagonists, or agonists; such analogs are also considered to be useful in the invention.

There now follows a description of the cloning and characterization of a ZPR1 polypeptide isolated from a murine cDNA library that is useful in the instant invention.

Murine ZPR1 is a Zinc Finger Protein

A two-hybrid screen as described by Fields et al. (Nature 340:245, 1989) was employed to identify proteins that bind to the COOH terminal region of the non-activated EGF receptor as follows. This screen was biased towards identification of proteins that bind to the EGF receptor in the absence of tyrosine phosphorylation, i.e., the non-activated state.

Using this screen, several ZPR1 cDNA fragments were isolated from a mouse embryo cDNA library using the yeast strain L40 [MATa hisD200 trp1-901 leu2-3,112 ade2 LYS:: (lexAop)4-HIS URA3::(lexAop)8-lacZ] described by Vojtek et al. [Cell 74, 205 (1993)]. The bait plasmid expressed the LexA DNA binding domain fused to the COOH terminal region of the human EGF receptor (residues 908–1186) [Ullrich et al., Nature 309:418, 1984]. Twenty million yeast transformants were examined for growth on media in the absence of histidine. Positive clones were subsequently confirmed by measurement of LacZ expression.

Nucleotide sequence analysis of these positive clones identified cDNA clones that were fused in-frame to the activation domain of VP16. This analysis demonstrated that these clones corresponded to fragments of five different cDNAs. One of these cDNAs, designated ZPR1, was independently isolated six times and was chosen for further analysis.

To isolate a full-length ZPR1 clone, we screened a murine fetal cell (NIH 3T3) cDNA library (Stratagene Inc.) with a random-primed ZPR1 cDNA fragment according to standard methods. From this screening, ten positive clones were isolated, including a full-length ZPR1 clone (2,162 bp). This clone was sequenced with an Applied Biosystems model 373A sequencer. The sequence of the nucleotide and deduced amino acid of ZPR1 is shown in FIG. 1. Examination of the ZPR1 sequence demonstrated that the $NH_2$-terminal region was similar to the COOH terminal region (FIG. 8). Each of these regions contained a putative zinc finger: $Cys-X_2-Cys-X_{25}-Cys-X_2-Cys$ (where $X_2$ and $X_{25}$ represent a series of 2 and 25 amino acids, respectively; FIG. 8; SEQ ID NO:28).

Fungal ZPRs

Homologs of ZPR1 in the yeast S. cerevisiae and S. pombe were identified by screening genomic libraries using a probe prepared from the full-length mouse ZPR1 cDNA according to standard hybridization and cloning methods. The yeast ZPR1 genes were characterized by automated sequencing using an Applied Biosystems model 373A machine. The nucleotide sequence of the S. cerevisiae (FIG. 5; SEQ ID NO:6) and the S. pombe (FIG. 6; SEQ ID NO:7) genes were determined. The deduced sequence of the S. cerevisiae (FIG. 3; SEQ ID NO:3) and the S. pombe (FIG. 4; SEQ ID NO:4) ZPR1 proteins demonstrated the presence of two zinc fingers, similar to the mouse ZPR1 (FIGS. 1 and 8).

Human ZPRs

A human ZPR1 homolog was identified by screening a HeLa cDNA library cloned into λ phage (Stratagene, Inc.) for sequences related to ZPR1. The library was screened using murine ZPR1 cDNA as a probe. The clones were characterized by automated sequencing using an Applied Biosystems model 373A machine.

The human ZPR1 protein (SEQ ID NO:2) deduced from the sequence of cDNA clones (SEQ ID NO:8) is similar to mouse ZPR1 (FIG. 2). Comparison of the sequence of the mammalian and yeast ZPR1 proteins demonstrated that they share conserved structural motifs, including the presence of two zinc fingers ($CysX_2Cys-X_{25}-CysX_2Cys$, SEQ ID NO:28)

Zinc Fingers in ZPR1 Polypeptides

The presence of both zinc fingers was confirmed using inductively coupled plasma emission spectroscopy as follows. Six milligrams of purified GST-ZPR1 were prepared by expressing ZPR1 in bacteria as glutathione-S-transferase (GST) fusion proteins by sub-cloning PCR fragments of the ZPR1 cDNA in the EcoRI and XhoI sites of pGEX-5X-1 (Pharmacia LKB Biotechnology Inc.). Purified GST-ZPR1 protein was dialyzed against water, lyophilized, and then solubilized by incubation for 30 minutes at 65° C. in concentrated nitric acid (0.5 ml) prior to standard spectroscopic analysis. The results of this analysis demonstrated the presence of 1.9±0.1 moles of zinc per mole of ZPR1 protein (mean ±SE, n=3).

ZPR1 expression was examined by Northern blot analysis of polyA+ mRNA isolated from various murine tissues (Clontech) using a ZPR1 cDNA probe labeled with [$\alpha$-$^{32}$P] CTP by a random priming method (Amersham International PLC). Northern blot analysis demonstrated that the ~2.1 kb ZPR1 mRNA is expressed in different murine tissues, including heart, brain, spleen, lung, liver, muscle, kidney, and testis. Highest levels of ZPR1 expression were detected in testis.

Expression of ZPR1 was also examined in transfected COS-1 cells maintained in Dulbecco's modified Eagle's medium supplemented with calf serum (5%) (Gibco-BRL) carrying an empty expression vector or a ZPR1 expression vector. ZPR1 expression vectors were constructed by sub-cloning the ZPR1 cDNA in the HindIII and EcoRI sites of pCDNA3 (InVitrogen Inc.). Transfection studies were performed with the lipofectamine reagent (Gibco-BRL) and purified plasmid DNA according to conventional methods. Proteins isolated from the transfected cells were fractionated by SDS-PAGE and transferred to a polyvinylidene difluoride membrane (Immobilon-P) according to standard methods. The blots were then probed according to standard methods with a rabbit polyclonal ZPR1 antibody which was prepared using a synthetic ZPR1 peptide corresponding to the ZPR1 COOH terminus (NDMKTEGYEAGLAPQ, SEQ ID NO:26) as an antigen. Immunecomplexes were detected using enhanced chemiluminescence (Amersham International Corp.) according to conventional methods. Immunoblot analysis using the anti-peptide antibody demonstrated that the murine ZPR1 was detected as an approximately 51 kDa protein. Furthermore, a large increase in ZPR1 expression was detected following transfection with a ZPR1 expression vector.

ZPR1 Binds to the EGF Receptor Tyrosine Kinase Domain

The isolation of ZPR1 cDNA clones by an interaction trap suggested that ZPR1 binds to the EGF receptor. We therefore examined the binding of ZPR1 and several of its domains, including ZF1 (residues 1–86 of ZPR1, SEQ ID NO:12), A (residues 87–255 of ZPR1, SEQ ID NO:14), ZF1+A (residues 1–255 of ZPR1, SEQ ID NO:29) ZF2 (residues 256–294 of ZPR1, SEQ ID NO:13), B (residues 295–439, SEQ ID NO:15), ZF2+B (residues 256–439 of ZPR1, SEQ ID NO:30), ZF1+A+ZF2 (residues 1–294, SEQ ID NO:31), and ZF1+A+ZF2+B (i.e., residues 1–439 of ZPR1, SEQ ID NO:32) to the EGF receptor in vitro (FIG. 9). EGF receptors bound to ZPR1 or a ZPR1 domain were detected by immunoblot analysis (as described above). ZPR1 and its domains were expressed in bacteria as glutathione-S-transferase (GST) fusion proteins and purified by glutathione-agarose affinity chromatography [Smith et al., Gene 67, 31 (1988)]. Bacterial ZPR1 expression vectors were constructed by sub-cloning PCR fragments of the ZPR1 cDNA in the EcoRI and XhoI sites of pGEX-5X-1 (Pharmacia LKB Biotechnology Inc.). The GST fusion proteins (5 μg) were immobilized on glutathione-agarose beads. Immobilized GST fusion proteins (5 μg) were then individually incubated with soluble cell extracts (1 ml) prepared from 2.5×10$^5$ A431 cells using lysis buffer [20 mM Tris (pH 7.4), 2 mM EDTA, 2 mM Na pyrophosphate, 25 mM Na β-glycerophosphate, 1 mM Na orthovanadate, 25 mM NaCl, 0.1% TRITON® X-100, 10% glycerol, 1 mM PMSF, 10 μg/ml leupeptin, and 10 μg/ml aprotinin]. A431 cells were maintained in Dulbecco's modified Eagle's medium supplemented with 5% calf serum (Gibco-BRL). Each binding reaction was incubated at 22° C. for 1 hour. The agarose beads were then washed extensively with lysis buffer and bound EGF receptors were detected by immunoblot analysis using the 20.3.6 monoclonal antibody to the EGF receptor [Galcheva-Gargova et al. Oncogene 11:2649, 1995]. An aliquot of the cell lysate (5%) used for the binding assays was also examined by immunoblot analysis. Control experiments were performed using immobilized GST. This analysis demonstrated that the EGF receptor binds to ZPR1.

The deletion studies were also performed to determine regions of ZPR1 that bind to the EGF receptor. Bacterial ZPR1 expression vectors containing ZPR1 deletions were constructed by sub-cloning PCR fragments of the ZPR1 cDNA into appropriate restriction sites of pGEX-3X (Pharmacia LKB Biotechnology Inc.) according to conventional methods.

The results of the deletion analysis indicated that the zinc fingers (ZF1 or ZF2) were sufficient for the EGF receptor binding interaction. Both zinc fingers bound to the EGF receptor. When Cys$^{80}$ and Cys$^{83}$ of ZF1 and Cys$^{288}$ and Cys$^{291}$ of ZF2 of ZPR1 were replaced with serine according to standard methods [e.g., according to Ho et al., Gene 77, 51 (1989)], the ZPR1/EGF receptor binding interaction was reduced, but not eliminated. These data demonstrated that ZPR1 binds to the EGF receptor, and that this interaction required the zinc fingers.

To identify regions of the EGF receptor that were required for binding to the ZPR1 zinc fingers, we next examined the effect of deletions of the COOH terminal region of the EGF receptor on the binding interaction. In initial experiments, we examined the effect of proteolytic cleavage of the COOH terminus of the EGF receptor with calpain as follows. Calpain cleavage of the EGF receptors was performed by harvesting cells in lysis buffer without EDTA, PMSF, leupeptin, and aprotinin [Gregoriou et al., Eur. J. Biochem. 223:455, 1994]. The extracts were then clarified by centrifugation at 100,000×g for 20 minutes at 4° C., and standard binding assays were performed as described herein. We found that both the wild-type and the calpain-cleaved EGF receptor bound to the ZPR1 zinc fingers.

Since the major sites of calpain-cleavage of the EGF receptor are Gln$^{996}$ and Asp$^{1059}$ [Gregoriou et al., Eur. J. Biochem. 223, 455 (1994)], we concluded that the COOH terminus of the EGF receptor (residues 996 to 1186) is not required for interaction with ZPR1. In contrast, ZPR1 bound to the COOH terminal region of the EGF receptor (residues 908 to 1186) in the yeast two-hybrid analysis described above. Together, these data suggested that the region of the EGF receptor required for interaction with ZPR1 corresponded to residues 908 to 996. To test this hypothesis, we prepared [$^{35}$S]methionine-labeled wild-type and truncated EGF receptors by in vitro translation according to standard techniques, and evaluated their ability to bind ZPR1. The wild-type human EGF receptor and a mutant receptor truncated at residue 958 have been described [Davis, J. Biol. Chem. 263, 9462 (1988); Ekstrand et al., Proc. Natl. Acad. Sci. USA 89, 4309 (1992)]. The EGF receptor mutant truncated at residue 908 was prepared by restriction digestion with BglII and subcloning according to standard methods.

In vitro translated [$^{35}$S]methionine-labeled wild-type or truncated EGF receptors (Δ958 or Δ908) were incubated in lysis buffer with 5 μg of either GST-ZPR1 fusion protein or GST immobilized on glutathione-agarose at 4° C. for 1 hour. The agarose beads were then washed extensively with lysis buffer and bound EGF receptors were detected by SDS-PAGE and Phosphorimager analysis (Molecular Dynamics Inc.) according to standard methods. Truncation of the human EGF receptor at residue 958 (designated Δ958) caused a small decrease in binding to ZPR1. Binding of wild-type EGF receptor to ZPR1 was also detected (FIG. 10) In contrast, truncation of the receptor at residue 908 (designated Δ908) caused a marked decrease in EGF receptor binding to ZPR1. Together, these data demonstrated that a specific region of the EGF receptor (including residues 908 to 958) is required for binding to ZPR1.

Residues 908 to 958 of the EGF receptor correspond to sub-domains X and XI of the tyrosine kinase domain. This region is highly conserved in members of the EGF receptor family (HER1, HER2, HER3, and HER4). A related sequence is found in the platelet-derived growth factor (PDGF) receptor, but the sequence differs for other receptor tyrosine kinases (FIG. 11). Examination of the conserved tyrosine kinase domain secondary structure [Hubbard et al., Nature 372, 746 (1994)] indicated that sub-domains X and XI include three α-helices (G, H, and I) that form a surface at the base of the kinase domain. This surface can represent the site of interaction of the ZPR1 zinc fingers with the EGF receptor and is distinct from the tyrosine phosphorylated COOH terminal region of the EGF receptor that binds SH2 and PTB proteins.

The conserved secondary structure of the region of the EGF receptor that is required for ZPR1 binding suggests that other protein kinases can interact with ZPR1. Binding studies of representative proteins to ZPR1 were also performed. The binding of tyrosine kinase receptor A (TrkA) was examined using extracts of Sf9 cells infected with a TrkA baculovirus [Wolf et al., J. Biol. Chem. 270:2133 (1995)]. The binding of the insulin receptor, insulin growth factor 1 (IGF-1) receptor, platelet derived growth factor (PDGF) receptor β, mitogen-activated protein (MAP) kinases (ERK, JNK, and p38), and MAP kinases kinases (MKK1, MKK3, and MKK4) were examined using extracts prepared from transfected COS-cells. The expression vectors used for these studies were pCMV5-PDGF-Rb (Valius and Kazlaushas, Cell 73:321, 1993], pCMV5-INS-R [Lewis et al. J. Biol. Chem. 269:26259, 1994], pCMV5-IGF1-R [Lewis et al. J. Biol. Chem. 269:26259, 1994], pCMV-Flag-p38 [Raingeaud, et al., J. Biol. Chem. 270, 7420 (1995)], pCDNA3-Flag-JNK1 [Dérijard, et al., Cell 76, 1025 (1994)], pCMV-HA-ERK2 [Catling et al., Mol. Cell Biol. 15:5214, 1995], pCMV-HA-MKK1 [Mansour et al., Science 265:966, 1994], pRSV-Flag-MKK3 (B. Dérijard, et al., Science 267, 682 (1995)), pCDNA3-Flag-MKK4 (B. Dérijard, et al., Science 267, 682 (1995)). Immunecomplexes were detected using the monoclonal Flag antibody M2 (IBI-Kodak), the monoclonal EGF-R antibody 20.3.6, rabbit polyclonal PDGF receptor β antibody (Upstate Biotechnology Inc.), monoclonal anti-IGF1 receptor antibody aIR3 (Oncogene Science), monoclonal anti-insulin receptor antibody CT-1 [Soos et al., Adv. Exp. Med. Biol. 343:145, 1993], rabbit polyclonal TrkA antibody #203 [Wolf et al., J. Biol. Chem. 270:2133, 1995], and a rabbit polyclonal ZPR1 antibody that was prepared using the synthetic peptide NDMKTEGYEAGLAPQ (SEQ ID NO:26). Control experiments demonstrated that ZPR1 did not bind to MAP kinases (ERK, JNK, and p38), MAP kinase kinases (MKK1, MKK3, MKK4), TrkA, the insulin receptor, or the IGF-1 receptor (data not shown). However, both the PDGF receptor and the EGF receptor bound to ZPR1 (data not shown). Together, these data demonstrated that ZPR1 binds selectively to a subgroup of receptor protein kinases that includes the EGF receptor.

EGF Regulates the Binding of ZPR1 to the EGF Receptor

The effect of EGF on the binding of the EGF receptor to ZPR1 was then examined. Extracts from control A431 cells and EGF-treated (100 nM EGF for 5 minutes at 37° C.) A431 cells were obtained and incubated with immobilized ZPR1 as described above. The bound EGF receptors were subsequently detected by immunoblot analysis as described above and the extent of EGF receptor tyrosine phosphorylation, and the binding of EGF receptors to immobilized ZPR1 (GST-ZPR1) examined.

Treatment of A431 cells with EGF caused decreased binding of the EGF receptor to ZPR1. A431 cells were incubated for different periods of time (0, 5, 15, 30, 60, and 120 minutes) with or without 100 nM EGF at 37° C. and the ZPR1/EGR-R complexes detected using the monoclonal antibody 20.3.6 that recognizes the EGF receptor. The decreased binding effect of EGF was observed in experiments using either ZPR1 (GST-ZF1-A-ZF2)or ZPR1 zinc fingers (GST-ZF1 or GST-ZF2), was rapid (within 5 minutes), and occurred before EGF receptor down-regulation In contrast to the effect of EGF, treatment of cells with phorbol myristate acetate caused no change in EGF receptor binding to ZPR1.

To confirm that EGF regulates the interaction between the EGF receptor and ZPR1 in living cells, we performed co-immunoprecipitation analysis. ZPR1 was isolated from cell extracts by immunoprecipitation with an antibody to ZPR1 as follows. A431 cells cultured in 100 mm dishes were serum-starved (12 hours) and treated without and with 100 nM EGF for 5 minutes at 37° C. Soluble extracts were prepared with 1 ml of lysis buffer [20 mM Tris (pH 7.4), 2 mM EDTA, 2 mM Na pyrophosphate, 25 mM Na β-glycerophosphate, 1 mM Na orthovanadate, 25 mM NaCl, 0.1% Triton X-100, 10% glycerol, 1 mM PMSF, 10 μg/ml leupeptin, and 10 μg/ml aprotinin]. ZPR1 was immunoprecipitated with a rabbit polyclonal antibody that was prepared with the antigen GST-ZPR1 (residues 292–416) as described herein. Control experiments were done with pre-immune serum. The complexes were washed three times with 20 mM Tris (pH 7.4), 2 mM EDTA, 137 mM NaCl, 2 mM Na pyrophosphate, 25 mM Na β-glycerophosphate, 1 mM Na orthovanadate, 1% Triton X-100, 0.5% deoxycholate, 0.1% sodium dodecylsulfate, 10% glycerol, 1 mM PMSF, 10 μg/ml leupeptin, and 10 μg/ml aprotinin. The ZPR1 immunoprecipitates were then examined by immunoblot analysis with the monoclonal EGF receptor antibody 20.3.6 as described above.

Immunobolt analysis demonstrated the presence of EGF receptors in the ZPR1 immunoprecipitates. In contrast, EGF receptors were not detected in immunoprecipitates of ZPR1 prepared from EGF-treated cells. Together, these data indicated that ZPR1 interacts with the EGF receptor in vivo and that the formation of this complex is negatively regulated by EGF. The mechanism of negative regulation is mediated by the presence of ZPR1 binding proteins in extracts of EGF-treated cells or by decreased affinity of the ZPR1\EGF receptor interaction.

ZPR1 Binding to the EGF Receptor is Regulated By Tyrosine Phosphorylation

Treatment of cells with EGF caused increased binding of the EGF receptor to SH2 and PTB signaling proteins and decreased binding of the EGF receptor to ZPR1. This difference was confirmed by direct comparison of the interaction of the EGF receptor with ZPR1 and the NH$_2$-terminal SH2 domain of PLC-γ. The level of EGF receptor expression and tyrosine phosphorylation was examined in lysates prepared from A431 cells incubated with and without 100 nM EGF for 5 minutes at 37° C. The amount of EGF receptor expression and tyrosine phosphorylation was detected by immunoblot analysis uing the monoclonal phosphotyrosine antibody PY20 (ICN Biomedicals Inc.) and the antiphosphotyrosine/horseradish peroxidase conjugate RC20 (Transduction Labs.). The bidnign of EGFreceptors to immobilized PLCγN-SH2 domain or APR1 was examined by immunoblot analysis using the monoclonal antibody EGF-R 20.3.6. Soluble extracts were prepared in the presence and absence of the tyrosine phosphatoase inhibitor orthovanadate. The interaction of the EGF receptor with SH2 and PTB proteins requires tyrosine phosphorylation of the receptor Thus, A431 cell extracts prepared without the tyrosine phosphatase inhibitor orthovanadate contained EGF receptors that were not tyrosine phosphorylated and did not bind to the NH$_2$-terminal SH2 domain of PLC-γ. Similarly, the tyrosine phosphatase inhibitor orthovanadate was required for EGF regulation of ZPR1 binding to the EGF receptor. Control experiments designed to examine the role of Ser or Thr phosphorylation by investigating the requirement for Ser-Thr phosphatase inhibitors did not support a role for Ser or Thr phosphorylation in the regulation of EGF receptor binding to ZPR1 (data not shown). These data indicated a primary role for tyrosine phosphorylation in the regulation of EGF receptor binding to ZPR1.

To test this hypothesis, we subsequently examined the interaction between ZPR1 and a mutated kinase-negative EGF receptor (K721R) in Chinese hamster ovary (CHO) cells by immunoblot analysis. CHO cells expressing the human wild-type [Lys$^{721}$]EGF-R and the mutated, kinase-negative [Arg$^{721}$]EGF-R have been described by Countaway et al. [*J. Biol. Chem.* 267, 1129 (1992)]. These cells were maintained in Ham's F12 medium supplemented with 5% fetal bovine serum (Gibco-BRL). The cells expressing the different receptors were incubated with 100 nM EGF for 5 minutes at 37° C. The blot was probed using the monoclonal EGF-R antibody 20.3.6. In these experiments, our results indicated that the binding of ZPR1 to the kinase-negative EGF receptor was not altered by treatment of cells with EGF. Together, these data demonstrated that tyrosine phosphorylation is required for the regulation of EGF receptor binding to ZPR1.

ZPR1 Over-Expression Inhibits EGF-Stimulated SHC Phosphorylation

The binding of ZPR1 to the non-activated EGF receptor contrasts with the binding of the activated EGF receptor to proteins with SH2 or PTB domains. To test whether the over-expression of ZPR1 would alter the interaction of the EGF receptor with SH2 or PTB proteins in living cells, we examined the effect of ZPR1 over-expression on the tyrosine phosphorylation of the SH2-PTB protein SHC using the method described by Pelicci et al. [*Cell* 70, 93 (1992)]. For immunoblot analysis, the Flag epitope (-Asp-Tyr-Lys-Asp-Asp-Asp-Asp-Lys-, SEQ ID NO:27); Immunex Corp.) was inserted between codons 1 and 2 of the ZPR1 cDNA by insertional overlapping PCR as described by Ho et al. [*Gene* 77, 51 (1989)], and the epitope-tagged ZPR1 was detected using the monoclonal Flag antibody M2 (IBI-Kodak) according to standard methods. COS-1 cells were transfected with epitope-tagged ZPR1, and then incubated without and with 100 nM EGFfor 5 minutes at 37° C. The EGF receptor and epitope-tagged ZPR1 were detected using monoclonal antibodies 20.3.6 and M2, respectively. SHC was detected with a rabbit polyclonal SHC antibody. Protein immunoblot analysis of lysates prepared from the transfected COS-1 cells demonstrated the presence of the EGF receptor and SHC polypeptides (66 kD, 52 kD, and 46 kD isoforms).

Treatment of the cells with EGF caused increased Ser, Thr, and Tyr phosphorylation and decreased electrophoretic mobility of the EGF receptor. EGF causes increased phosphorylation and reduced electrophoretic mobility of the EGF receptor during SDS-PAGE. Contributions to the gel shift arise from increased Ser, Thr, and Tyr phosphorylation. The EGF receptor gel shift was observed in EGF-treated cells over-expressing ZPR1. As ZPR1 inhibits EGF receptor tyrosine phosphorylation, the observed gel shift indicated that ZPR1 does not inhibit the EGF-stimulated Ser and Thr phosphorylation of the EGF receptor. This increased Ser and Thr phosphorylation is caused, in part, by activation of cytoplasmic protein kinases [Countaway et al., *J. Biol. Chem.* 264, 10828 (1989)]. Thus, the reduced EGF-stimulated tyrosine phosphorylation observed in cells over-expressing ZPR1 is not sufficient to block signaling completely by the EGF receptor. Indeed, control experiments demonstrated that EGF can activate the MAP kinase ERK2 in cells over-expressing ZPR1. Phosphotyrosine immunoblot analysis of EGF receptor immunoprecipitates and SHC immunoprecipitates (using the phosphotyrosine antibody, RC20) demonstrated that EGF caused increased tyrosine phosphorylation of the EGF receptor and SHC polypeptides. The over-expression of ZPR1 caused a reduction in the EGF-stimulated tyrosine phosphorylation of both the EGF receptor and SHC. Consistent with this reduced level of tyrosine phosphorylation, ZPR1 over-expression decreased the EGF-stimulated formation of SHC-EGF receptor complexes that were detected by immunoblot analysis of SHC immunoprecipitates with antibodies to the EGF receptor and phosphotyrosine. Together, these data indicated that ZPR1 over-expression caused an inhibition of EGF-stimulated tyrosine phosphorylation. It is possible that the interaction of ZPR1 with the non-activated EGF receptor contributes to the inhibition of EGF-stimulated tyrosine phosphorylation caused by over-expressed ZPR1.

Redistribution of ZPR1 from the Cytoplasm to the Nucleus in EGF-treated Cells

The sub-cellular location of ZPR1 in serum-starved and EGF-treated cells was examined by use of immunofluorescence analysis. A431 cells were cultured on glass coverslips (22 mm square; Corning) according to coventional methods. The cells were then rinsed briefly with phosphate-buffered saline (PBS) and fixed at −20° C. with methanol for 5 minutes and acetone for 2 minutes. EGF receptors were detected according to known methods with the monoclonal antibody 528 [Kawamoto, et al., *Proc. Natl. Acad. Sci. USA,* 80, 1337 (1983)], the Golgi region was detected with a human antibody to a Golgi-associated antigen [Fritzler et al., *Mol. Biol. Cell* 5, 1043, (1994)], and ZPR1 was detected with the rabbit polyclonal antibody raised against the synthetic peptide NDMKTEGYEAGLAPQ (SEQ ID NO:26) described herein. Incubation with the primary antibodies was done at 25° C. for 1 hour. The coverslips were then washed three times with PBS and incubated with species-specific secondary antibodies coupled to fluorescein or rhodamine (Caltag Laboratories) for 1 hour. Next the coverslips were washed three times with PBS and mounted on slides with Vectashield media (Vector Laboratories). Control experiments using pre-immune immunoglobulin and competition analysis with antigen demonstrated the specificity of the ZPR1 immunofluorescence. Microscopy was done with a MRC-600 confocal laser scanning microscope with an argon/krypton mixed gas laser (BioRad Laboratories) fitted to a Zeiss Axiovert epifluorescence microscope with an oil immersion objective lens (1.4 N.A.; 63×). Images were collected from a single focal plane (approximately 0.4 µm) using Kalman averaging of 30 scans (BioRad COMOS program). The rhodamine and fluorescein images were collected simultaneously, digitized, and subsequently merged. Differential interference contrast (DIC) images were collected after fluorescence imaging. The images were recorded on Kodak Ektar 25 film.

We found that the ZPR1 protein was widely distributed in the cytoplasm, but not in the nucleus, of serum-starved cells. In addition, an accumulation of ZPR1 was detected in the perinuclear region of the cells. This perinuclear region was observed to be co-localized with a Golgi-associated antigen. EGF receptors were also detected in this perinuclear region and at the cell periphery. Double-label immunofluorescence analysis with antibodies against ZPR1 and the EGF receptor was performed to test whether the cytoplasmic ZPR1 protein co-localized with the EGF receptor. Partial co-localization of ZPR1 with a sub-population of EGF receptors was observed. These data demonstrated a cytoplasmic localization of both ZPR1 and the EGF receptor. Treatment of the cells with EGF altered the sub-cellular distribution of the EGF receptors. The punctate staining of EGF receptors observed after EGF-treatment is likely to reflect the internalization and sequestration of the EGF receptors in an endosomal compartment. EGF was also found to cause the partial redistribution of ZPR1 within the cell. Double-label immunofluorescence analysis of EGF-treated cells demonstrated that the ZPR1 protein was detected adjacent to the Golgi marker. Differential interference contrast microscopy indicated that ZPR1 was located in the nucleus of EGF-treated cells. This conclusion was confirmed by double-label immunofluorescence studies to compare the distribution of ZPR1 with other nuclear antigens, specifically, coilin, pol I, and snRNP. Antisera to human p80 coilin and pol I were described by Andrade et al., *J. Exp. Med.* 173:1407–1419 (1991) and Reimer et al., *J. Clin. Invest.* 79:65–72 (1987), respectively. The human anti-snRNP antibody is a reference serum (obtained from Dr. Y. Tan, Scripps Research Institute). ZPR1 co-localized with fibrillarin and RNA pol 1, but did not co-localize with the splicing factor SC35 or p80 coilin. Together, these data demonstrated that the cytoplasmic ZPR1 protein accumulates in the nucleolus of activated cells.

The binding of ZPR1 to the non-activated EGF receptor and the dissociation of ZPR1 from the activated EGF receptor indicates that ZPR1 functions to stabilize the non-activated EGF receptor. The observation that the overexpression of ZPR1 inhibits EGF-stimulated tyrosine phosphorylation of SHC is consistent with this hypothesis. Thus, ZPR1 repressed basal signaling by the non-activated EGF receptor. In addition, ZPR1 represents a class of signaling molecule that is released from the receptor following activation. The released ZPR1 can function by interacting with proteins, nucleic acids, or other biomolecules via the zinc fingers or the inter-finger domains.

The above is a system that can be used, for example, to assay for substances that disrupt ZPR1 localization.

Sub-Nucleolar Location of Zpr

The nucleolus is composed of separate regions, including fibrillar centers, the dense fibrillar component, and the granular component (Shaw and Jordan, *Annu. Rev. Cell Dev. Diol.* 11;93–121 (1995). Each of these components is thought to correspond to a different functional region of the nucleolus. Since these regions are interspersed, it is not possible to determine the sub-nucleolar localization of ZPR1 by immunofluorescence microscopy. However, the nucleolus can be segregated into fibrillar and granular regions by use of drugs (Simar and Bernhardt, *J. Cancer* 1:463–479 (1966); Ochs et al., *Biol. Cell* 54:123–134 (1985)). At low doses, actinomycin D intercalates into GC-rich regions of DNA and markedly inhibits pol I transcription of rRNA (Abelson and Penman, *Handbook Exp. Pharm.* 38:571–581 (1975). The adenosine analog 5,6-dichloro-β-D-ribofuranosylbenzimidazole (DRB), induces segregation of nucleolar components without altering the ultrastructural characteristics of the fibrillar and granular compartments of the nucleolus (Granick, *J. Cell Biol.* 65:418–427 (1975). Thus, HEp-2 cells were treated for 4 hours with 0.1 µg/ml actinomycin D or with 25 µg/ml DRB. The cells were then fixed and processed for immunofluorescence microscopy using antibodies raised against ZPR1, and antibodies that stain the fibrillar component (fibrillarin) and the granular component (B23) of the nucleolus. Fixation was in methanol (5 minutes, −20° C.) followed by acetone (2 minutes, −20° C.). The cells were then permeabilized with 0.1% TRITON®X-100 and incubated with primary antibodies diluted in phosphate-buffered saline (PBS). Incubations were for 1 hour at 25° C. After extensive washing, the cells were incubated with fluorescently labeled secondary antibodies (Caltag Laboratories), washed and mounted on slides using Vectashield (Vector Laboratories). The rabbit polyclonal antibody to ZPR1 (Galcheva-Gargova, et al., *Science* 272:1797–1802 (1996) mouse monoclonal antibody to fibrillarin 72B9 (Reimer et al., *J. Clin. Invest.* 79:65–72 (1987), anti-DNA antibody 1.D12 (Kotzin et al., *J. Immunol.* 133:2554–2559 (1984), and the anti-SC-35 antibody (Fu and Maniatis, *Nature* 343:437–441 (1990). The anti-B23 monoclonal antibody was provided by Dr. I. Todorov. Cells treated with actinomycin D were stained from ZPR1 and fibrillarin. Cells treated with DRB were stained with antibodies to ZPR1 and fibrillarin or ZPR1 and B23. Cells were observed with epifluorescence and differential interference contrast (DIC) microscopy and photographed.

Treatment of HEp-2 cells with actinomycin D caused the formation of fibrillar caps (stained with an antibody to fibrillarin) and the dissociation of ZPR1 from the nucleolus. These data indicate that ZPR1 is not located in the same compartment of the nucleolus as fibrillarin. However, as actinomycin D causes some disruption of the granular region of the nucleolus, it is possible that ZPR1 may be located within the granular component of the nucleolus. Experiments in which cells were treated with DRB demonstrated that ZPR1 did not co-localize with either a marker for the fibrillar component (fibrillarin) or the granular component (B23) of the segregated nucleolus. Together, these data demonstrate that ZPR1 is not an integral component of the granular or fibrillar compartments of the nucleolus. Thus, ZPR1 may be peripherally associated with one of these nucleolar compartments. Alternatively, ZPR1 may be located within a distinct region of the nucleolus Methods such as this are useful for identification of molecules that affect ZPR1 localization.

RNA is Required for the Nucleolar Localization of ZPR1

The nucleolus is the major site of transcription of rRNA genes and the processing of rRNA into pre-ribosomal particles (Woolford and Warner, *The Ribosome and its Synthesis*, vol. 1, Broach, PRingle and Jones, eds. (New York: Cold Spring Harbor Laboratory Press (1991) and Shaw and Jordan, *Annu. Rev. Cell Dev. Biol.* 11:93–121 (1995). The nucleic acid composition of the nucleolus differs from other regions of the nucleus because of the abundance of rRNA genes and rRNA transcripts. This distinctive nucleic acid composition (both DNA and RNA) may contribute to the accumulation of ZPR1 in the nucleolus.

To examine the possible role of nucleic acids in ZPR1 localization, immunofluorescence microscopy was used to follow the effects of nuclease digestion on ZPR1 localization. HEp-2 cells were grown on microscope slides, permeabilized with 0.1% TRITON® X-100 in phosphate-buffered saline (PBS) for 3 minutes on ice, washed, and digested with 0.1 mg/ml DNase I in PBS containing 5 mM $MgCl_2$ with 0.1 mg/ml RNase A in PBS for 60 minutes at 37° C. After digestion, the cells were washed in PBS and processed for indirect immunofluorescence. Buffers without enzymes served as negative controls. A human antibody raised against snRNP or a monoclonal antibody specific for DNA were used to monitor the efficiency of DNase I and RNase A digestions, respectively. DAPI was used as a counterstain for nucleic acids. Digestion with DNase I caused a marked decrease in nuclear DNA, which was detected using a monoclonal antibody raised against DNA. However, this treatment did not affect the nucleolar location of ZPR1. In contrast, digestion with RNase A caused a marked decrease in the nucleolar location of ZPR1. Control studies demonstrated that RNase A digestion did not alter nuclear DNA, but did reduce the nuclear presence of snRNP. Together, these data indicate that the nucleolar localization of ZPR1 requires RNA, but not DNA, thus, ZPR1 nucleolar localization appears to be mediated by the interaction of ZPR1 (directly or indirectly) with RNA.

These methods are used to identify molecules that interfere with ZPR1 localization to the nucleolus.

ZPR1 is an RNA binding protein

Studies of the effect of nucleases on the nucleolar location of ZPR1 indicate that this association requires RNA. One possible explanation for this observation is that ZPR1 binds RNA. To test this hypothesis, the interaction of ZPR1 with nucleic acids was examined. Binding experiments indicated that ZPR1 does not exhibit a high level of non-specific binding to nucleic acids. However, the possibility that ZPR1 exhibits specific RNA binding activity is not excluded by these data.

To test whether ZPR1 might bind to specific RNA molecules, [$^{32}$P]-labeled RNA was prepared by in vitro transcription and binding to recombinant ZPR1 assessed using an electrophoretic mobility shift assay (EMSA). RNA was prepared by in vitro transcription of cDNA templates in the presence of [$\alpha$-$^{32}$P]UTP using T3 or T7 polymerase (Maxiscript kit; Ambion Inc.). Binding reactions were done in the presence of tRNA (0.15 mg/ml) and bovine serum albumin (0.1 µg/ml) in a final volume of 25 µl. Recombinant ZPR1, prepared as described (Galcheva-Gargova et al., *Science* 272:1797–1802 (1996), was incubated in binding buffer (10 mM Tris-HCl, pH 7.5, 50 mM KC1, 50 mM NaCl, 10% glycerol, 1 mM DTT, 90 µg/ml bovine serum albumin, 0.15 mg/ml tRNA, and 1000 U/ml RNAsin) for 15 minutes at 4° C. The labeled RNA was added to this reaction mixture and incubated for 30 minutes at 30° C. Bound and non-bound RNA were separated by acrylamide gel electrophoresis and detected by autoradiography (Singh et al., *Science* 268:1173–1176 (1995)). The migration of the RNA was analyzed in the absence of ZPR1 and in the presence of increasing concentrations of ZPR1 (0.7, 1.4, and 2.8 µg). The interaction of ZPR1 with the snoRNAs U3, U10, U15, U22, U33, or the viral RNAs corresponding to the RRE (HIV Rev responsive element), HIV trans-acting response element (TAR), and adenovirus VA-RNA1 (Akusjavari et al., *Proc. Natl. Acad. Sci. USA* 77:2424–2428 (1980); Feng and Holland, *Nature* 334:165–167 (1988); Bartel et al., *Cell* 67:529–539 (1991)) was investigated by this method. No binding of ZPR1 was detected in experiments using viral RNA corresponding to RRE, the TAR, or adenovirus VA-RNA1. In contrast, binding to ZPR1 was detected in experiments using several small nucleolar RNAs (snoRNAs), including U3, U15, and U22.

The specificity of the interaction of RNA with ZPR1 was examined in greater detail in competition experiments using the snoRNA, U3. A [$^{32}$P]-labeled U3 probe was incubated with ZPR1 alone or in the presence of excess non-radioactive U3, anti-sense U3, or tRNA. The resulting complexes were examined by EMSA. In this competition analysis, the binding of [$^{32}$P]-labeled U3 to ZPR1 was eliminated in the presence of a 20-fold excess of non-radioactive U3. In contrast, a 20-fold excess of anti-sense U3 failed to compete with U3 for binding to ZPR1. Similarly, a 200-fold excess of a non-specific competitor (tRNA) did not compete for binding to ZPR1. These data establish that the interaction of U3 with ZPR1 is saturable and does not represent a non-specific complex.

Previous studies have demonstrated that zinc fingers are able to interact with RNA (Mattaj, *Cell* 73:837–840 (1993); Burd and Dreyfuss, *Science* 265:615–621 (1994)). As ZPR1 contains two zinc fingers, the role of these zinc fingers in the interaction of ZPR1 with U3 was examined. A series of ZPR1 molecules with deletions was constructed and the binding of a [$^{32}$P]-labeled U3 probe to the deleted ZPR1 molecules was assayed by EMSA. The following ZPR1 fragments were used: residues 1–267, residues 1–774, residues 757–888, residues 757–1380, and residues 1–888. Full-length ZPR1 (residues 1–1380) were bound to U3 (WT). In contrast, none of the ZPR1 fragments bound detectably to U3. Thus, these studies indicate that the full-length ZPR1 molecule is required for interaction with U3. Similar methods can be used to test for other RNAs that interact with ZPR1.

Analysis of U3 Sequences Required for Interaction with ZPR1

To define the sequences within U3 that are required for binding to ZPR1, the effect of deletions within U3 on the binding to ZPR1 was examined (FIG. 12). Deletions were generated using the polymerase chain reaction (PCR). Binding assays were performed by EMSA as described above. U3 contains two conserved box elements (C and D) in the 3' region (see FIG. 13 and Maxwell and Fournier, *Ann. Rev. Biochem.* 35:897–934 (1995)). There was little or no decrease in the binding of ZPR1 to a U3 fragment lacking the D box indicating that although the D box may contribute to ZPR1 binding, it is not required for interaction with ZPR1. However, deletion of sequences including the C box caused a marked decrease in binding to ZPR1. These data suggested that the 3' stem loop of U3 that includes the C and D boxes may be the site of interaction with ZPR1. The observation that the 5' stem loop of U3 fails to bind to ZPR1 is consistent with this hypothesis. However, it was found that the 3' stem loop was also unable to bind ZPR1. Together, these data suggest that sequences located in both the 5' and 3' regions of U3 are required for interaction with ZPR1. To test this hypothesis, the U3 residues protected from chemical modification by the interaction with ZPR1 were investigated by footprint analysis. Chemical protection analysis of the ZPR1 footprint on U3 was performed using methods described previously (Purohit and Stern, *Nature*

Figure 13:
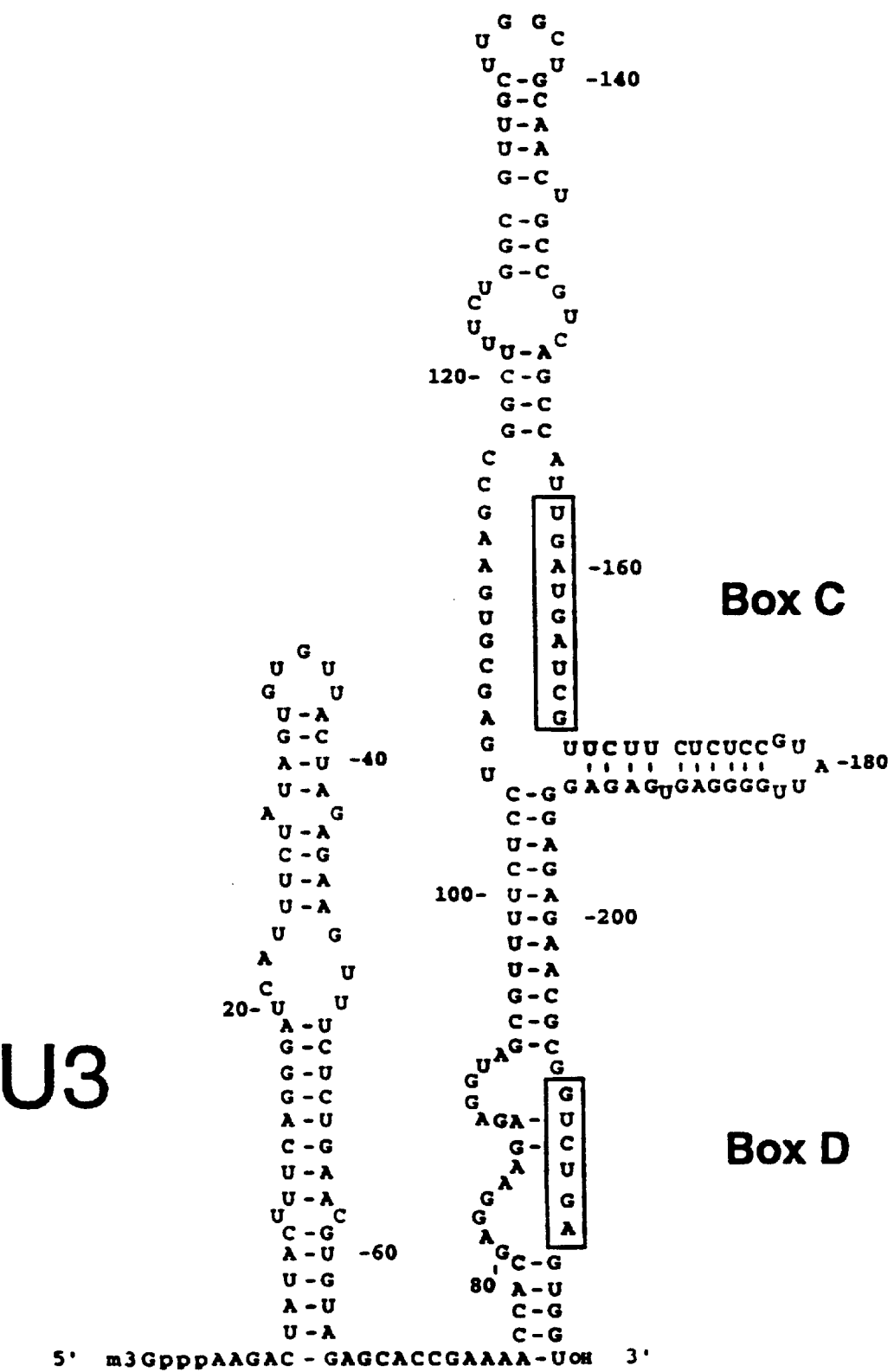
FIG. 13 is a schematic representation of U3 secondary structure.

370:659–662 (1994)). Protected residues were detected throughout the U3 molecule, including bases in the C/D boxes and within both stem loops (FIG. 13). The binding of ZPR1 therefore involves extensive contact with the U3 molecule. Furthermore, the interaction with ZPR1 caused increased chemical modification of U3 at certain sites, indicating that the interaction with ZPR1 causes a change in the conformation of U3.

The deletion analysis of ZPR1 and U3, together with the identification of an extensive ZPR1 foot-print on the U3 molecule, provide strong support for the conclusion that the nucleolar protein ZPR1 is an RNA binding protein.

These mehtods can be used, for example, in the identification and design of RNAs that bind ZPR1.

Gene Disruption Studies Demonstrate that zpr1 is an Essential Gene

Biochemical analysis of ZPR1 indicates that it may have an important function in the nucleolus in vivo. To examine the cellular role of ZPR1, the effect of disrupting the ZPR1 gene was examined. These studies were facilitated by the identification of ZPR1 in fission and budding yeast (FIGS. 3, 4, 5, and 6). As fission yeast have properties that are more similar to mammalian cells than do budding yeast, the analysis was focused on the zpr1$^+$ gene of the fission yeast S. pombe. Homologous recombination was used to disrupt the zpr1$^+$ gene by replacement with the ura4$^+$ gene. Genetic and biochemical manipulation of S. pombe was performed using standard techniques (Moreno et al., Methods in Enzymol. 194:795–826 (1991)). Disruption of the zpr1$^+$ gene was done by insertion of the ura4$^+$ gene (1.7-kb Bam H1-Hind III fragment) in the BstE2 and EcoRV sites of the zpr1$^+$ coding region (2.9-kb XbaI fragment). The disrupted zpr1$^+$ genomic clone (4.6-kb XbaI fragment) was transfected into diploid yeast (Moreno et al., supra). Disruption of the zpr1$^+$ gene was confirmed by Southern blot analysis of genomic DNA isolated from transformants. The heterozygous diploid strain was designated TE630 [zpr1::ura4$^+$/zpr1$^+$, ade6-M210/ade6-M216, ura4-d18/ura4-d18, leuI-32/leuI-32, h-/h$^+$]. Control haploid isogenic strains were designated TE331 and TE332 [ade6-M210, ura4-d18, leuI-32 h+ (or h–)]. The structure of the zpr1$^+$ genomic locus and the disrupted gene (zpr1::ura4$^+$) is presented schematically in FIG. 15.

Southern blot analysis was used to examine the ura4$^+$ diploid transformants heterozygous for the disrupted zpr1$^+$ allele. The genomic DNA from colonies of yeast transformants was restricted with BglII and probed with a [$^{32}$P]-labeled, random-primed fragment of the zpr1$^+$ genomic locus (the 2.9 kb XbaI fragment). The wild-type zpr1$^+$ allele was identified in wild-type yeast. A disrupted zpr1::ura4$^+$ allele (3 kb) was identified in some, but not all transformants. Yeast identified as heterozygous were sporulated and examined by tetrad analysis. The heterozygous diploid yeast strain TE630 (zpr1+/ZPR::ura4$^+$) was sporulated and the tetrads dissected. The viability of the spores was examined by growth on agar plates supplemented with uracil. Viability segregated 2:2 and none of the viable haploid colonies obtained were ura4$^+$. Thus, zpr1$^+$ is an essential gene in S. pombe. Similar studies demonstrated that the ZPR1 gene was also essential for viability in S. cerevisiae.

To demonstrate that the loss of viability was caused by the disruption of the zpr1$^+$ gene, complementation analysis was performed, using plasmid vectors that express zpr1$^+$. Complementation studies were performed using the promoterless vector pIRT2 and pREP41, which contains the regulated nmt promoter. The S. pombe zpr1$^+$ gene (2.9-kb XbaI fragment) was cloned into the SmaI site of pIRT2. Regulated expression vectors for S. pombe zpr1$^+$, S. cerevisiae ZPR1, and murine ZPR1 were constructed by cloning PCR fragments in the polylinker of pREP41. The yeast strain TE630 was transformed and haploid yeast were selected on plates supplemented with adenine. The growth of the haploid yeast was examined on agar plates and liquid minimal medium in the absence and presence of thiamine (10 mM). Cells grown to mid-log phase in liquid culture were employed for RNA isolation, [$^{35}$S]methionine labeling, and microscopy using standard procedures. The RNA was examined by Northern blot analysis by probing with a random-primed PCR fragment (base pairs 150–1120) corresponding to the 5' ETS region of S. pombe rRNA (GenBank Accession number Z19578). The heterozygous (zpr1$^+$/zpr1::ura4$^+$) diploid yeast strain TE630 was transformed with the plasmid pREP41 or the plasmid pREP41-zpr1, selected on minimal agar plates without leucine or uracil, sporulated, and haploid yeast were selected on minimal media supplemented with adenine. No viable haploid yeast (zpr1::ura4$^+$) were obtained from diploid yeast transformed with pREP41. However, the zpr1 expression vector pREP41-zpr1 complemented the lethal phenotype of the disrupted zpr1$^+$ gene. Complementation was observed in experiments using S. pombe zpr1$^+$, S. cerevisiae ZPR1, and murine ZPR1. Repression of the nmt promoter in the pREP plasmid with thiamine decreased the growth of the complemented ZPR::ura4$^+$ haploid strains, but not the wild-type zpr1$^+$ haploid strain transformed with pREP41-zpr1.

A 2.9 kb XbaI genomic fragment that contained the zpr1$^+$ gene complemented the loss of viability caused by the disrupted zpr1$^+$ allele. Furthermore, complementation was observed in experiments using a plasmid vector (pREP41-zpr1) in which the zpr1$^+$ coding sequence was expressed under the control of the nmt promoter. Repression of the nmt promoter with thiamine did not affect the growth of the control (zpr1$^+$) strain transformed with pREP41-zpr1. In contrast, thiamine caused a marked decrease in the growth of the zpr1-disrupted strain. Similar results were obtained in complementation studies using the S. cerevisiae and murine ZPR1 genes. Deletion analysis of zpr1$^+$ demonstrated that the full-length ZPR1 protein is required for complementation. For example, a mutant ZPR1 molecule with a deletion of the COOH terminus after the second zinc finger (residues 889–1380) failed to complement the zpr1-disrupted strain.

These data establish that the zpr1$^+$ gene is essential for viability. Furthermore, the observation that loss-of-function mutations can be complemented by both mammalian and yeast genes indicates that the biological function of the ZPR1 protein has been conserved during evolution. These experiments illustrate methods that can be used, for example, to establish the potential utility of ZPR1 constructs for gene therapy and aid in determining function of ZPR1 mutations.

Loss of zpr1$^+$ Function Causes Depletion of the rRNA Precursor and Decreased Protein Translation The function of the ZPR1 protein was examined by analyzing the effect of repression of zpr1$^+$ expression using the thiamine-regulated nmt promoter. These experiments were performed using haploid yeast (zpr1$^+$ and zpr1-disrupted strains) transformed with the zpr1$^+$ expression vector pREP41-zpr1. Wild-type haploid S. pombe (zpr1$^+$) and the zpr1::ura4$^+$ disrupted strain were transformed with the plasmid pREP41-zpr1 and grown in minimal liquid medium. The cultures were divided into two flasks in the absence and presence of thiamine, respectively. Thiamine is a repressor of the nmt promoter located in the pREP plasmid. The growth of the cultures was monitored by measurement of the optical density at 595 nm. Addition of thiamine to repress the nmt promoter caused no change in the growth of the zpr1⁺ strain in liquid cultures, but caused decreased growth of the zpr1-disrupted strain. The morphology of the yeast grown in the presence of thiamine was examined by phase contrast microscopy. DNA stained with DAPI was visualized by epifluorescence. Microscopic analysis demonstrated that the zpr1⁺ strain consisted of a population of yeast that were distributed throughout the cell cycle, including both large and small yeast. In contrast, cultures of the zpr1-disrupted strain contained a more uniform population of small yeast. The morphology of the zpr1-disrupted strain is consistent with a growth arrested phenotype.

Figure 15:
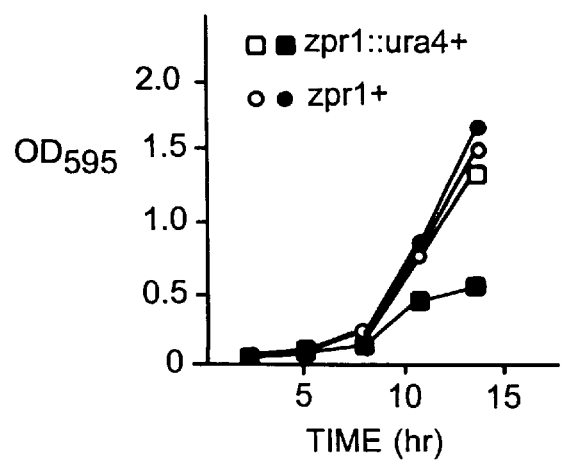
FIG. 15 is a graph showing the growth of wild type and zpr1::ura4+ yeast transformed with the plasmid pREP41-zpr1 and grown in the presence and absence of thiamine.

To further biochemically characterize the effect of zpr1⁺ repression, we examined protein synthesis in the zpr1⁺ and zpr1-disrupted strains. Wild-type and zpr1::ura4⁺ disrupted strains were grown in the absence and presence of the repressor thiamine. The cells were diluted to the same density (0.2 OD$_{595}$) and labeled with [$^{35}$S]methionine (150 µCi/ml) for 3 hours and harvested. The labeling with [$^{35}$S] methionine was performed in the absence and presence of thiamine. Extracts prepared from the yeast were examined by SDS-PAGE and autoradiography. Liquid cultures of these yeast were incubated with [$^{35}$S]methionine for 3 hours and the incorporation of radioactivity into protein was examined following SDS-PAGE by autoradiography. Addition of thiamine to the zpr1⁺ strain caused no change in the incorporation of [$^{35}$S]methionine. The extent of [$^{35}$S]methionine incorporation was similar to that observed in experiments using the zpr1-disrupted strain grown in the absence of thiamine. In contrast, addition of thiamine to the zpr1-disrupted strain caused a marked reduction in protein synthesis. A partial recovery of protein synthesis was observed if thiamine was omitted from the culture during the incubation with [$^{35}$S]methionine. Together, these data demonstrate that the loss of zpr1⁺ expression interferes with protein biosynthesis. The marked reduction in protein synthesis may account for the small size and reduced growth of the zpr1-disrupted strain (FIG. 15).

The nucleolus is the major site of assembly of the ribonucleoprotein complexes that form the ribosome, the cellular machine that is used for protein synthesis. The defect in protein synthesis caused by the loss of the nucleolar protein ZPR1 suggests that ZPR1 plays an important role in the assembly of ribosomes. To test this hypothesis, Northern blot analysis was performed to examine RNA isolated from the zpr1⁺ and the zpr1::ura4⁺ disrupted *S. pombe* strains transformed with the plasmid pREP41-zpr1. Yeast were grown in the absence and presence of the repressor thiamine. Ten micrograms of RNA isolated from these yeast was examined by use of denaturing agarose gel electrophoresis. The 25S and 18S mature rRNA were detected by staining with ethidium bromide. The 35S rRNA precursor was detected by Northern analysis using a 5' ETS probe. The dried blot was exposed for autoradiography. The yield of RNA from thiamine-treated zpr1-disrupted yeast was reduced compared with other yeast cultures. However, when the same amount of total RNA was examined by denaturing agarose gel electrophoresis, the mature 25S and 18S rRNA were found to be similar in zpr1⁺ and zpr1-disrupted strains. In contrast, Northern blot analysis demonstrated a marked reduction in the amount of the 35S rRNA precursor detected in the thiamine-treated zpr1-disrupted strain. These data demonstrate that zpr1⁺ is required for the accumulation of the rRNA precursor. The absence of the rRNA precursor may account for the markedly reduced protein synthesis caused by loss-of-function mutations in zpr1.

Diagnosis

The level of ZPR1 expression was examined by Western blot analysis using an antibody that was prepared using the synthetic peptide NDMKTEGYEAGLAPQ (SEQ ID NO:26) as an antigen. Compared with normal (non-transformed) cells, a higher level of ZPR1 expression was detected in tumor-derived cells, including epidermoid carcinoma (cervix), renal carcinoma, and lymphoma. These observations indicated that the expression (or activity) of ZPR1 is useful as a marker for (or were a contributing factor to) the growth and differentiation properties of cells (including malignant transformation). In addition to changes in the level of expression of ZPR1, changes in the activity of ZPR1 may result from mutations in the ZPR1 gene. The nucleotide sequence of ZPR1 enables the detection of mutations in the ZPR1 gene according to any standard method.

Isolation of Other ZPR1 cDNAs and Genomic DNAs

Based on the isolation described herein of the aforementioned ZPR1 genes and polypeptides, the isolation of additional preferable ZPR1 coding sequences (e.g., mammalian ZPRs such as human ZPR) is made possible using standard strategies and techniques that are well known in the art. For example, using all or a portion of the amino acid sequence of ZPR1 polypeptide of the invention, one can readily design Zpr-specific oligonucleotide probes, including ZPR1 degenerate oligonucleotide probes (i.e., a mixture of all possible coding sequences for a given amino acid sequence). These oligonucleotides can be based upon the sequence of either DNA strand and any appropriate portion of the ZPR1 sequence. General methods for designing and preparing such probes are provided, for example, in Ausubel et al., 1996, *Current Protocols in Molecular Biology*, Wiley Interscience, New York, and Berger and Kimmel, *Guide to Molecular Cloning Techniques*, 1987, Academic Press, New York. These oligonucleotides are useful for ZPR1 gene isolation, either through their use as probes capable of hybridizing to ZPR1 complementary sequences or as primers for various amplification techniques, for example, polymerase chain reaction (PCR) cloning strategies.

Hybridization techniques and screening procedures are well known to those skilled in the art and are described, for example, in Ausubel et al. (supra); Berger and Kimmel (supra); and Sambrook et al., *Molecular Cloning: A Laboratory Manual*, Cold Spring Harbor Laboratory Press, New York. If desired, a combination of different oligonucleotide probes can be used for the screening of a recombinant DNA library. The oligonucleotides can be detectably-labeled using methods known in the art and used to probe filter replicas from a recombinant DNA library. Recombinant DNA libraries are prepared according to methods well known in the art, for example, as described in Ausubel et al. (supra), or they can be obtained from commercial sources (e.g., a hamster cDNA library that is available from Stratagene).

For detection or isolation of closely related ZPR1 sequences, high stringency conditions are preferably used; such conditions include hybridization at about 42° C. and about 50% formamide, a first wash at about 65° C., about 2×SSC, and 1% SDS, followed by a second wash at about 65° C. and about 0.1% SDS, and 1×SSC. Lower stringency conditions for detecting ZPR1 genes having about 85% sequence identity to the ZPR1 genes described herein include, for example, hybridization at about 42° C. in the absence of formamide, a first wash at about 42° C., about 6×SSC, and about 1% SDS, and a second wash at about 50° C., about 6×SSC, and about 1% SDS. These stringency conditions are exemplary; other appropriate conditions can be determined by those skilled in the art.

As discussed above, ZPR1 oligonucleotides can also be used as primers in amplification cloning strategies, for example, using PCR. PCR methods are well known in the art and are described, for example, in *PCR Technology*, Erlich, ed., Stockton Press, London, 1989; *PCR Protocols: A Guide to Methods and Applications*, Innis et al., eds., Academic Press, Inc., New York, 1990; and Ausubel et al. (supra). Primers are optionally designed to allow cloning of the amplified product into a suitable vector, for example, by including appropriate restriction sites at the 5' and 3' ends of the amplified fragment (as described herein). If desired, a ZPR1 gene can be isolated using the PCR "RACE" technique, or Rapid Amplification of cDNA Ends (see, e.g., Innis et al. (supra)). By this method, oligonucleotide primers based on a ZPR1 sequence are oriented in the 3' and 5' directions and are used to generate overlapping PCR fragments. These overlapping 3'- and 5'-end RACE products are combined to produce an intact full-length cDNA. This method is described in Innis et al. (supra); and Frohman et al., *Proc. Natl. Acad. Sci. USA* 85:8998, 1988.

Useful ZPR1 sequences can be isolated from any appropriate organism. Confirmation of a sequence's relatedness to the ZPR1 polypeptide family is accomplished by DNA sequencing and comparison, for example, to any of the ZPR1 sequences described herein. In addition, the activity of any ZPR1 sequence can be evaluated according to any of the techniques described herein.

The invention is also useful for the identification of ZPR1 mutations, for example, those that are associated with disease. These may be analyzed by methods known to with skill in the art, for example, by single-strand conformation polymorphism (SSCP), denaturing gradient gel electrophoresis (DGGE), temperature gradient gel electrophoresis (TGGE), or heteroduplex analysis.

Zpr Polypeptide Expression

A ZPR1 polypeptide can be expressed following transformation of a suitable host cell with all or a part of an ZPR1 polypeptide-encoding cDNA fragment (e.g., the cDNA described herein) in a suitable expression vehicle. As is discussed below, if desired, any ZPR1 polypeptide or a fragment of a ZPR1 polypeptide can be expressed as part of a gene fusion (e.g., a hexa-histidine-Zpr polypeptide, a GST-zpr polypeptide, a GST-ZF1 polypeptide, a GST-ZF2 polypeptide, or protein A-Zpr polypeptide fusion) according to conventional methods.

Those skilled in the field of molecular biology will understand that any of a wide variety of expression systems can be used to provide the recombinant protein in either a fused or non-fused form. For example, a ZPR1 polypeptide can be produced in a prokaryotic host (e.g., *E. coli*) or in a eukaryotic host (e.g., COS-1, CHO, A431, *Saccharomyces cerevisiae* or mammalian cells). Such cells are available from a wide range of sources (e.g., the American Type Culture Collection, Rockland, Md.; see also Ausubel et al. (supra)). The method of transformation and the choice of expression vehicle will depend on the host system selected. Transformation methods are described, e.g., in Ausubel et al. (supra); expression vehicles can be chosen from those provided, e.g., in *Cloning Vectors: A Laboratory Manual* (P. H. Pouwels et al., 1985, Supp. 1987).

One bacterial expression system for ZPR1 polypeptide production is the *E. coli* pET expression system (Novagen). Use of the pET expression system generally involves inserting DNA encoding a ZPR1 polypeptide into a pET vector in an orientation designed to allow expression. Since the ZPR1 gene is under the control of the T7 regulatory signals, expression of ZPR1 is induced by inducing the expression of T7 RNA polymerase in the host cell. This is typically achieved using host strains which express T7 RNA polymerase in response to IPTG induction. Once produced, recombinant ZPR1 polypeptide is then isolated according to standard methods known in the art, e.g., those described herein.

Another bacterial expression system for ZPR1 polypeptide production is the pGEX expression system (Pharmacia). This system employs a GST gene fusion system which is designed for high-level expression of genes or gene fragments as fusion proteins with rapid purification and recovery of functional gene products. The protein of interest is fused to the carboxyl terminus of the glutathione S-transferase from *Schistosoma japonicum* and is readily purified from bacterial lysates by affinity chromatography using Glutathione Sepharose 4B. Fusion proteins can be recovered under mild conditions by elution with glutathione. Cleavage of the glutathione S-transferase domain from the fusion protein is facilitated by the presence of recognition sites for site-specific proteases upstream of this domain. For example, proteins expressed in pGEX-2T plasmids can be cleaved with thrombin; those expressed in pGEX-3X can be cleaved with factor Xa.

Alternatively, ZPR1 polypeptides can be produced in mammalian systems. Vectors suitable, for example, for stable transfection of mammalian cells are available to the public (see, for example, Pouwels et al. (supra)), and methods for constructing such cell lines are well known (see, e.g., Ausubel et al. (supra)). In one particular example, cDNA encoding an ZPR1 polypeptide is cloned into an expression vector that includes the dihydrofolate reductase (DHFR) gene. Integration of the plasmid and, therefore, the ZPR1 polypeptide-encoding gene into the host cell chromosome is selected for by inclusion of 0.01–300 $\mu$M methotrexate in the cell culture medium (as described in Ausubel et al., supra). This dominant selection technique can be accomplished in most cell types.

If desired, recombinant protein expression can be increased by DHFR-mediated amplification of the transfected gene. Methods for selecting cell lines bearing gene amplifications are described in Ausubel et al. (supra); such methods generally involve extended culture in medium containing gradually increasing levels of methotrexate. DHFR-containing expression vectors commonly used for this purpose include pCVSEII-DHRF and pAdD26SV(A) (described in Ausubel et al., supra). A DHFR-deficient CHO cell line (e.g., CHO DHFR$^-$ cells, ATCC Accession No. CRL 9096) is among the host cells preferred for DHFR selection of a stably-transfected cell line or DHFR-mediated gene amplification.

Once a recombinant ZPR1 polypeptide is expressed, it is isolated, e.g., using affinity chromatography. In one example, isolation is facilitated by inclusion in the ZPR1 polypeptide of a leader sequence or "tag" that allows ZPR1 polypeptide capture (for example, the GST sequence described herein). In another example, the ZPR1 polypeptide product is isolated using an anti-Zpr polypeptide antibody (e.g., produced as described herein). This antibody can be attached to a solid support (e.g., a column) or can be used in immunoprecipitation methods to bind and isolate the ZPR1 polypeptide of interest. Lysis and fractionation of ZPR1 polypeptide-harboring cells prior to affinity chromatography can be performed by any standard method (see, e.g., Ausubel et al., supra). Once isolated, the recombinant protein can, if desired, be further purified, e.g., by high performance liquid chromatography (see, e.g., Fisher, *Laboratory Techniques In Biochemistry And Molecular Biology*, eds., Work and Burdon, Elsevier, 1980). These general techniques of polypeptide expression and purification can also be used to produce and isolate useful ZPR1 polypeptide fragments or analogs (as described herein).

Anti-Zpr Antibodies

To generate Zpr-specific antibodies, a ZPR1 coding sequence (i.e., amino acids 292–416) was expressed as a C-terminal fusion with glutathione S-transferase (GST) (Smith et al., Gene 67:31–40, 1988). The fusion protein (which was shown to be of the predicted size) was purified on glutathione-Sepharose beads, eluted with glutathione, cleaved with thrombin (at the engineered cleavage site), and purified to the degree necessary for immunization of rabbits. Primary immunizations were carried out with Freund's complete adjuvant and subsequent immunizations with Freund's incomplete adjuvant. Antibody titres were monitored by immunoblot and immunoprecipitation analyses using the thrombin-cleaved ZPR1 protein fragment of the GST-Zpr fusion protein.

As an alternate or adjunct immunogen to GST fusion proteins, peptides corresponding to relatively unique hydrophilic regions of ZPR1 can be generated and coupled to keyhole limpet hemocyanin (KLH) through an introduced C-terminal lysine. Antiserum to each of these peptides is similarly affinity purified on peptides conjugated to BSA, and specificity tested in ELISA and immunoblots using peptide conjugates, and by immunoblot and immunoprecipitation using ZPR1 expressed as a GST fusion protein.

Alternatively, monoclonal antibodies can be prepared using any of the ZPR1 proteins described above and standard hybridoma technology (see, e.g., Kohler et al., Nature 256:495, 1975; Kohler et al., Eur. J. Immunol. 6:511, 1976; Kohler et al., Eur. J. Immunol. 6:292, 1976; Hammerling et al., In Monoclonal Antibodies and T Cell Hybridomas, Elsevier, N.Y., 1981; Ausubel et al., supra). Once produced, monoclonal antibodies are also tested for specific ZPR1 recognition by immunoblot or immunoprecipitation analysis (e.g., by the methods described in Ausubel et al., supra). Antibodies which specifically recognize ZPR1 are considered to be useful in the invention; such antibodies can be used, e.g., in an immunoassay to monitor the level of ZPR1 produced by a mammal (for example, to determine the amount or subcellular location of Zpr) or can be used to assay ZPR1 binding (as described herein).

Once produced, polyclonal or monoclonal antibodies are tested for specific ZPR1 polypeptide recognition, for example, by immunoblot or immunoprecipitation analysis (as described, for example, in Ausubel et al., supra). Antibodies that specifically recognize a ZPR1 polypeptide are considered to be useful in the invention; such antibodies can be used, e.g., to neutralize the biological activity of an activated EGF receptor.

Identification and Administration of Molecules that Modulate ZPR1 Protein Expression and Activity Isolation of the ZPR1 cDNA also facilitates the identification of molecules that increase or decrease ZPR1 expression. According to one approach, candidate molecules are added at varying concentrations to the culture medium of cells expressing ZPR1 mRNA. ZPR1 expression is then measured, for example, by standard Northern blot analysis (Ausubel et al., supra) using a ZPR1 cDNA (or cDNA fragment) as a hybridization probe. The level of ZPR1 expression in the presence of the candidate molecule is compared to the level measured for the same cells in the same culture medium but in the absence of the candidate molecule.

If desired, the effect of candidate modulators on expression can, in the alternative, be measured at the level of ZPR1 protein production using the same general approach and standard immunological detection techniques, such as immunoblotting or immunoprecipitation with a Zpr-specific antibody (for example, using the ZPR1 antibodies and methods described herein).

ZPR1 modulators may also be molecules that interfere with ZPR1 activity. This includes interfering with the normal binding of ZPR1 to receptors (e.g., EGF receptor) and to RNA (e.g., small nucleolar RNA). Candidate modulators may be assayed by known methods. For example, molecules may be added to assays described below demonstrating the binding of ZPR1 to non-activated EGF receptor. Molecules that prevent this binding or prevent dissociation of ZPR1 from the activated EGF receptor are useful for the invention. Similarly, molecules that, when added to the assays described below that show ZPR1 binding to RNA, prevent that binding are useful. Such molecules may be peptides or nucleic acids. Nucleic acids useful for this aspect of the invention may be introduced into cells by a number of methods described herein, e.g., transfection, lipofection, or direct application.

Candidate modulators can be purified (or substantially purified) molecules or can be one component of a mixture of compounds (e.g., an extract or supernatant obtained from cells; Ausubel et al., supra) . In a mixed compound assay, ZPR1 expression is tested against progressively smaller subsets of the candidate compound pool (e.g., produced by standard purification techniques, e.g., HPLC or FPLC) until a single compound or minimal compound mixture is demonstrated to modulate ZPR1 expression.

Candidate ZPR1 modulators include peptide as well as non-peptide molecules (e.g., peptide or non-peptide molecules found, e.g., in a cell extract, mammalian serum, or growth medium on which mammalian cells have been cultured).

A molecule that promotes an increase in ZPR1 expression or activity is considered useful in the invention; such a molecule can be used, for example, as a therapeutic to increase cellular levels of ZPR1 or to increase ZPR1 binding activity and thereby exploit ZPR1's protective anti-cancer effect.

Furthermore, a molecule that promotes an increase in ZPR1 expression or activity is useful for the inhibition of unwanted angiogenesis. Endothelial cells secrete a group of growth factors, e.g., EGF, that are mitogenic for endothelium and induce the formation of new blood vessels, i.e., angiogenesis. Abnormal angiogenesis is associated with a variety of diverse disease states, including tumor growth, diabetic retinopathy, rheumatoid arthritis, psoriasis, and coronary atheroma. For example, tumor growth depends on an adequate blood supply which in turn is dependent on the growth of new blood vessels and capillaries into the tumor, which is regulated by EGF activity.

A molecule that promotes a decrease in ZPR1 expression or activity is also considered useful in the invention; such a molecule can be used, for example, as a therapeutic to decrease cellular levels of ZPR1 or to decrease ZPR1 binding activity and thereby exploit ZPR1's ability to activate EGF receptors upon release from the receptor complex. Since a decrease in ZPR1 expression or activity results in activation of the EGF receptor and its cascade of biological activity, a molecule that promotes activation of the EGF receptor by modulating ZPR1 activity or binding is useful for regulating EGF receptor activity and concomitant cell growth. Thus, a molecule that promotes the decrease in ZPR1 activity is useful in a variety of situations for enhancing cell growth, including, but not limited to, tubular regeneration of kidney cells following acute renal failure, angiogenesis in the heart for protecting the myocardium from the consequences of coronary obstruction, and in in vitro cell culture (as described below). For example, rates of tubular regeneration and functional recovery afacute ute renal failure (e.g., due to acute tubular necrosis) can be accelerated by administration of modulators capable of decreasing ZPR1 activity.

Modulators found to be effective at the level of ZPR1 expression or activity can be confirmed as useful in animal models and, if successful, can be used as therapeutics in animals, e.g., mammals, and in humans.

Evaluation of whether a test compound confers protection against the development of a neoplasm generally involves using an animal known to develop a neoplasm (e.g, mammary carcinoma in mice that express mutated and activated HER2 (Bargmann et al., Nature 319:226, 1986). An appropriate animal is treated with the test compound according to standard methods, and a reduced incidence of neoplasm development, compared to untreated control animals, is detected as an indication of protection.

A ZPR1 modulator can be administered with a pharmaceutically-acceptable diluent, carrier, or excipient, in unit dosage form. For example, conventional pharmaceutical practice can be employed to provide suitable formulations or compositions to administer ZPR1 or a ZPR1 modulatory compound to patients suffering from or presymptomatic for a ZPR1-associated carcinoma (e.g., mammary tumor, melanoma, neuroblastoma, epidermoid carcinoma (e.g., cervix)). Any appropriate route of administration can be employed, for example, parenteral, intravenous, subcutaneous, intramuscular, intracranial, intraorbital, ophthalmic, intraventricular, intracapsular, intraspinal, intracisternal, intraperitoneal, intranasal, aerosol, or oral administration. Therapeutic formulations can be in the form of liquid solutions or suspensions; for oral administration, formulations can be in the form of tablets or capsules; and for intranasal formulations, in the form of powders, nasal drops, or aerosols.

Methods well known in the art for making formulations are found in, for example, "Remington's Pharmaceutical Sciences." Formulations for parenteral administration can, for example, contain excipients, sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers can be used to control the release of the compounds. Other potentially useful parenteral delivery systems for ZPR1 modulatory compounds include ethylene-vinyl acetate copolymer particles, osmotic pumps, implantable infusion systems, and liposomes. Formulations for inhalation can contain excipients, for example, lactose, or can be aqueous solutions containing, for example, polyoxyethylene-9-lauryl ether, glycocholate and deoxycholate, or can be oily solutions for administration in the form of nasal drops, or as a gel.

If desired, treatment with a ZPR1 modulatory compound can be combined with more traditional cancer therapies such as surgery, radiation, or chemotherapy.

ZPR1 Therapy

Because expression of ZPR1 correlates with EGF receptor activity, the ZPR1 gene finds use in anti-cancer gene therapy. For example, to cure a ZPR1-deficient carcinoma cell, a functional ZPR1 gene can be introduced into cells at the site of a tumor.

Retroviral vectors, adenoviral vectors, adeno-associated viral vectors, or other viral vectors with the appropriate tropism for ZPR1-expressing cells (for example, epithelial cells) can be used as a gene transfer delivery system for a therapeutic ZPR1 gene construct. Numerous vectors useful for this purpose are generally known [Miller, Human Gene Therapy 15–14, (1990); Friedman, Science 244:1275–1281, (1989); Eglitis and Anderson, BioTechniques 6:608–614, (1988); Tolstoshev and Anderson, Current Opinion in Biotechnology 1:55–61, (1990); Sharp, The Lancet 337:1277–1278, (1991); Cornetta et al., Nucleic Acid Research and Molecular Biology 36:311–322, (1987); Anderson, Science 226:401–409, (1984); Moen, Blood Cells 17:407–416, (1991); and Miller and Rosman, BioTechniques 7:980–990, (1989); Le Gal La Salle et al., Science 259:988–990, (1993); and Johnson, Chest 107:77S–83S, (1995)]. Retroviral vectors are particularly well developed and have been used in clinical settings [Rosenberg et al., N. Engl. J. Med 323:370, (1990); Anderson et al., U.S. Pat. No. 5,399,346].

Non-viral approaches can also be employed for the introduction of therapeutic DNA into malignant cells. For example, ZPR1 can be introduced into a carcinoma cell by the techniques of lipofection [Felgner et al., Proc. Natl. Acad. Sci. USA 84:7413, (1987); Ono et al., Neuroscience Lett. 117:259, (1990); Brigham et al., Am. J. Med. Sci. 298:278, (1989); Staubinger and Papahadjopoulos, Meth. Enz. 101:512, (1983)]; polylysine conjugation methods (Wu and Wu, J. Biol. Chem. 263:14621, 1988; Wu et al., J. Biol. Chem. 264:16985, (1989)]; or, by microinjection under surgical conditions [Wolff et al., Science 247:1465, (1990)].

For any of the above approaches, the therapeutic ZPR1 DNA construct is preferably applied to the site of the target area (e.g., a malignancy (for example, by injection)), but can also be applied to tissue in the vicinity of the target area or even to a blood vessel supplying the target area.

For gene therapy, ZPR1 cDNA expression is directed from any suitable promoter (e.g., the human cytomegalovirus, simian virus 40, or metallothionein promoters), and its production is regulated by any desired mammalian regulatory element. For example, if desired, enhancers known to direct preferential gene expression in epithelial cells can be used to direct ZPR1 expression.

Alternatively, if a ZPR1 genomic clone is utilized as a therapeutic construct (for example, following its isolation by hybridization with the ZPR1 cDNA described above), ZPR1 expression is regulated by its cognate regulatory sequences or, if desired, by regulatory sequences derived from a heterologous source, e.g., any of the promoters or regulatory elements described above.

ZPR1 gene therapy is also accomplished by direct administration of the ZPR1 mRNA to a target area (e.g., a malignancy). This mRNA can be produced and isolated by any standard technique, but is most readily produced by in vitro transcription using a ZPR1 cDNA under the control of a high efficiency promoter (e.g., the T7 promoter). Administration of ZPR1 mRNA to malignant cells is carried out by any of the methods for direct nucleic acid administration described above.

The production of ZPR1 protein by any gene therapeutic approach described above results in a cellular level of ZPR1 that is at least equivalent to the normal, cellular level of ZPR1 in an unaffected individual.

For the treatment of a malignancy, treatment by any ZPR1-mediated gene therapy approach can be combined with more traditional cancer therapies such as surgery, radiation, or chemotherapy.

Another therapeutic approach included within the invention involves direct administration of recombinant ZPR1 protein, either to the site of a target area (e.g., a malignancy (for example, by injection)) or systemically by any conventional recombinant protein administration technique. The actual dosage of ZPR1 depends on a number of factors, including the size and health of the individual patient, but, generally, between 0.1 and 10 mg inclusive are administered per day to an adult in any pharmaceutically-acceptable formulation.

In addition, the invention further encompasses the therapeutic use ZPR1 oligonucleotides, e.g., antisense ZPR1 oligonucleotides, which can specifically bind to a complementary nucleic acid sequence. By binding to the appropiate target sequence, e.g., an RNA-RNA, a DNA-DNA, or RNA-DNA duplex is formed. These nucleic acids are termed "antisense" because they are complementary to the sense or coding strand of the gene. Furthermore, ZPR1 oligonucleotides are useful for the formation of a triple helix, where the oligonucleotide is bound to a DNA duplex. By binding to the target nucleic acid, ZPR1 oligonucleotides can inhibit the function of the target nucleic acid. This results, for example, in the blocking of transcription, processing of poly A+ addition, replication, translation, or promoting inhibitory mechanisms of the cell, such as RNA degradation. The triple helix forming ZPR1 oligonucleotides and antisense ZPR1 oligonucleotides are useful for selectively suppressing certain cellular functions described herein. In addition, the ZPR1 oligonucleotides are useful for the production of ribozymes.

Cell Culture Media

The invention provides a media containing a ZPR1 polypeptide or a fragment or analog of a ZPR1 polypeptide or an antagonist or agonist of non-activated membrane-bound receptor activity (e.g., the EGF receptor) useful for the culturing of a variety of cells, including cells of epithelial origin (e.g., skin or kidney cells). While such media generally do not require the use of serum (e.g., fetal bovine serum, calf serum, horse serum, normal mouse serum, human serum, porcine serum, and rabbit serum) those skilled in the art will understand and recognize that serum can be added if desired. Media formulations are generally prepared according to methods known in the art. Accordingly, any standard medium, e.g., RMPI-1630 Medium, CMRL Medium, Dulbecco's Modified Eagle Medium (D-MEM), Fischer's Medium, Iscove's Modified Dulbecco's Medium, McCoy's Medium, Minimum Essential Medium, NCTC Medium, and the like can be formulated with any of the compounds according to the invention. Cytokines are used in amounts effective to increase the proportion of cultured cells present in the culture. If desired, media supplements, e.g., salt solutions (e.g., Hank's Balanced Salt Solution or Earle's Balanced Salt Solution), antibiotics, nucleic acids, amino acids, carbohydrates, and vitamins are added according to known methods. The media are useful in a variety of culture conditions and for a variety of biological applications, including, without limitation, in vitro organ culture. Examples of such culture conditions include, without limitation, bioreactors (e.g., continuous or hollow fiber bioreactors), cell-suspension cultures, semisolid cultures, and liquid cultures. In addition, the media are also useful for industrial applications.

OTHER EMBODIMENTS

It is to be understood that while the invention has been described in conjunction with the detailed description thereof, that the foregoing description is intended to illustrate and not limit the scope of the invention, which is defined by the scope of the appended claims. Other aspects, advantages, and modifications are within the scope of the following claims.

What is claimed is:

1. An isolated nucleic acid comprising a sequence encoding a ZPR1 polypeptide, wherein the ZPR1 polypeptide includes two zinc fingers each having the amino acid sequence Cys-$X_2$-Csy-$X_{25}$-Cys-$X_2$-Cys (SEQ ID NO:28), where $X_2$ represents a series of any two amino acids and $X_{25}$ represents a series of any 25 amino acids.

2. The nucleic acid of claim 1, wherein said nucleic acid is from a eukaryote.

3. The nucleic acid of claim 1, wherein said nucleic acid is from a mammal.

4. The nucleic acid of claim 1, comprising the nucleotide sequence of SEQ ID NO:5.

5. The nucleic acid of claim 1, wherein said nucleic acid is obtained from a human.

6. The nucleic acid of claim 1, comprising the nucleotide sequence of SEQ ID NO:8.

7. The nucleic acid of claim 1, comprising the nucleotide sequence of SEQ ID NO:6 or SEQ ID NO:7.

8. An isolated nucleic acid which comprises a nucleotide sequence that is the complement of a nucleic acid that hybridizes under stringent hybridization conditions at about 42° C., and a wash at about 42° C., with about 6×SSC and about 1% SDS, to the nucleotide sequence of SEQ ID NO:5, SEQ ID NO:6, SEQ ID NO:7, or SEQ ID NO:8, wherein the isolated nucleic acid encodes a polypeptide that exhibits binding to a non-activated EGF receptor.

9. A vector comprising the isolated nucleic acid of claim 1.

10. A method of producing a recombinant ZPR1 polypeptide, said method comprising:
 (a) providing a cell transformed with a nucleic acid of claim 1 positioned for expression in said cell;
 (b) culturing said transformed cell under conditions for expressing said nucleic acid; and
 (c) recovering said recombinant ZPR1 polypeptide.

11. The method of claim 10, wherein said recombinant ZPR1 polypeptide is a fusion protein.

12. A nucleic acid of claim 1, wherein the first zinc finger has the sequence CMXCXXNGXTXLLLTXIPXFREXXX-SFXCXHC (amino acids 55–87 of SEQ ID NO:33), wherein X is any amino acid.

13. A nucleic acid of claim 1, wherein the second zinc finger has the sequence CPXCXXXXXTXMKXXXIPH-FKEVIIMXTXCXXC (amino acids 299–331 of SEQ ID NO:33), wherein X is any amino acid.

14. A nucleic acid of claim 1, comprising a nucleic acid sequence encoding SEQ ID NO:33.

15. An isolated nucleic acid which comprises a nucleotide sequence that is the complement of a nucleic acid that hybridizes under stringent hybridization conditions at about 42° C., and a wash at about 42° C., with about 6×SSC and about 1% SDS, to a nucleotide sequence encoding a first zinc finger having the sequence CMXCXXNGXTXLLLTX-IPXFREXXXSFXCXHC (amino acids 55–87 of SEQ ID NO:33), wherein Z is any amino acid, and a second zinc finger having the sequence CPXCXXXXXTXMKXXX-IPHFKEVIIMXTXCXXC (amino acids 299–331 of SEQ ID NO:33), wherein X is any amino acid, and wherein said isolated nucleic acid encodes a polypeptide that exhibits binding to a non-activated EGF receptor.

16. The nucleic acid of claim 1, wherein the ZPR1 polypeptide encoded by the nucleic acid exhibits binding to a non-activated EGP receptor.

17. The nucleic acid of claim 16, wherein the ZPR1 polypeptide exhibits nucleolar localization.

18. A method of measuring the expression of a ZPR1 gene in a cell, the method comprising isolating a sample of nucleic acid from the cell and assaying the amount of a ZPR1 nucleic acid sequence present in the sample using a ZPR1 nucleic acid probe, thereby measuring the expression of a ZPR1 gene.

19. A method of determining the presence of a mutation in a sample ZPR1 nucleic acid, the method comprising isolating a sample of nucleic acid from the cell and comparing the sample ZPR1 nucleic acid sequence to a known ZPR1 nucleic acid sequence, and determining any differences between the sample ZPR1 nucleic acid and the known ZPR1 nucleic acid, wherein any differences indicate the presence of a mutation in the sample ZPR1 nucleic acid.

20. An isolated nucleic acid comprising a nucleotide sequence that is the complement of a nucleic acid that hybridizes under stringent hybridization conditions at about 42° C., and a wash at about 42° C., with about 6×SSC and about 1% SDS, to a nucleotide sequence encoding a ZPR1 polypeptide comprising two zinc fingers each having the amino acid sequence Cys-$X_2$-Cys-$X_{25}$-Cys-$X_2$-Cys (SEQ ID NO:28), wherein $X_2$ represents a series of any two amino acids, and $X_{25}$ represents a series of any 25 amino acids, and wherein the isolated nucleic acid encodes a polypeptide that exhibits binding to a non-activated EGF receptor.

21. The nucleic acid of claim 20, wherein the ZPR1 polypeptide exhibits nucleolar localization.

22. The nucleic acid of claim 8, wherein the polypeptide exhibits nucleolar localization.

23. The nucleic acid of claim 15, wherein the polypeptide exhibits nucleolar localization.

* * * * *